United States Patent
Atanasoska et al.

(10) Patent No.: US 8,808,726 B2
(45) Date of Patent: Aug. 19, 2014

(54) BIOERODIBLE ENDOPROSTHESES AND METHODS OF MAKING THE SAME

(75) Inventors: Liliana Atanasoska, Edina, MN (US); Jan Weber, Maastricht (NL); Robert W. Warner, Woodbury, MN (US); Amy Grovender, Madison, WI (US)

(73) Assignee: Boston Scientific SciMed. Inc., Maple Grove, MN (US)

( * ) Notice: Subject to any disclaimer, the term of this patent is extended or adjusted under 35 U.S.C. 154(b) by 1395 days.

(21) Appl. No.: 11/855,499

(22) Filed: Sep. 14, 2007

(65) Prior Publication Data

US 2008/0183277 A1    Jul. 31, 2008

Related U.S. Application Data

(60) Provisional application No. 60/844,898, filed on Sep. 15, 2006.

(51) Int. Cl.
| | | |
|---|---|---|
| *A61F 2/06* | (2013.01) | |
| *A61L 31/16* | (2006.01) | |
| *A61L 31/10* | (2006.01) | |
| *A61L 31/14* | (2006.01) | |
| *A61F 2/82* | (2013.01) | |

(52) U.S. Cl.
CPC ......... *A61L 31/148* (2013.01); *A61L 2300/802* (2013.01); *A61F 2210/0004* (2013.01); *A61L 31/16* (2013.01); *A61L 31/10* (2013.01); *A61F 2/82* (2013.01)
USPC .......................................... 424/426; 623/1.15

(58) Field of Classification Search
None
See application file for complete search history.

(56) References Cited

U.S. PATENT DOCUMENTS

| | | |
|---|---|---|
| 2,950,187 A | 8/1960 | Ototani |
| 3,560,362 A | 2/1971 | Kasamatsu et al. |
| 3,569,660 A | 3/1971 | Houldcroft |
| 3,687,135 A | 8/1972 | Stroganov et al. |
| 3,758,396 A | 9/1973 | W.R. Vieth et al. |
| 3,868,578 A | 2/1975 | Oldham |
| 3,910,819 A | 10/1975 | Rembaum et al. |
| 3,948,254 A | 4/1976 | Zaffaroni |
| 3,952,334 A | 4/1976 | Bokros et al. |
| 3,993,072 A | 11/1976 | Zaffaroni |
| 4,002,877 A | 1/1977 | Banas |
| 4,101,984 A | 7/1978 | MacGregor |
| 4,143,661 A | 3/1979 | LaForge et al. |
| 4,202,055 A | 5/1980 | Reiner et al. |
| 4,237,559 A | 12/1980 | Borom |
| 4,308,868 A | 1/1982 | Jhabvala |
| 4,334,327 A | 6/1982 | Lyman et al. |
| 4,401,546 A | 8/1983 | Nakamura et al. |
| 4,532,929 A | 8/1985 | Mattei et al. |
| 4,539,061 A | 9/1985 | Sagiv |
| 4,542,539 A | 9/1985 | Rowe et al. |
| 4,585,652 A | 4/1986 | Miller et al. |
| 4,634,502 A | 1/1987 | Callahan et al. |
| 4,655,771 A | 4/1987 | Wallsten |
| 4,657,544 A | 4/1987 | Pinchuk |
| 4,665,896 A | 5/1987 | LaForge et al. |
| 4,705,502 A | 11/1987 | Patel |
| 4,713,070 A | 12/1987 | Mano |
| 4,725,273 A | 2/1988 | Kira |
| 4,733,665 A | 3/1988 | Palmaz |
| 4,767,418 A | 8/1988 | Deininger et al. |
| 4,784,659 A | 11/1988 | Fleckenstein et al. |
| 4,800,882 A | 1/1989 | Gianturco |
| 4,804,382 A | 2/1989 | Turina et al. |
| 4,886,062 A | 12/1989 | Wiktor |
| 4,954,126 A | 9/1990 | Wallsten |
| 4,976,692 A | 12/1990 | Atad |
| 4,994,071 A | 2/1991 | MacGregor |
| 5,024,671 A | 6/1991 | Tu et al. |
| 5,059,211 A | 10/1991 | Stack et al. |
| 5,061,275 A | 10/1991 | Wallsten et al. |
| 5,061,914 A | 10/1991 | Busch et al. |
| 5,073,365 A | 12/1991 | Katz et al. |
| 5,079,203 A | 1/1992 | Pinnavaia |
| 5,091,024 A | 2/1992 | DeBold et al. |
| 5,091,205 A | 2/1992 | Fan |
| 5,102,403 A | 4/1992 | Alt |
| 5,120,322 A | 6/1992 | Davis et al. |
| 5,125,971 A | 6/1992 | Nonami et al. |
| 5,147,370 A | 9/1992 | McNamara et al. |
| 5,163,958 A | 11/1992 | Pinchuk |
| 5,195,969 A | 3/1993 | Wang |
| 5,205,921 A | 4/1993 | Shirkanzadeh |
| 5,234,457 A | 8/1993 | Andersen |

(Continued)

FOREIGN PATENT DOCUMENTS

| | | |
|---|---|---|
| AU | 739 507 | 11/1998 |
| AU | 2003 203 722 | 11/2003 |

(Continued)

OTHER PUBLICATIONS

International Preliminary Report on Patentability for Application No. PCT/US2007/078450, dated Mar. 26, 2009, 7 pages.

Andión et al., "Corrosion behaviour at the interface of steel bars embedded in cement slurries Effect of phenol polymer coatings," *Corrosion Science*, 2002, 44:2805-2816.

Grassi et al., "Short-term administration of dark chocolate is followed by a significant increase in insulin sensitivity and a decrease in blood pressure in healthy persons," *Am. J. Clin. Nutr.*, 2005, 81(3):611-614.

Ito et al., "Antioxidant action of eugenol compounds; role of metal ion in the inhibition of lipid peroxidation," *Food Chem. Toxicol.*, 2005, 43:461-466.

(Continued)

*Primary Examiner* — Bethany Barham
*Assistant Examiner* — Danah Al-Awadi
(74) *Attorney, Agent, or Firm* — Fish & Richardson P.C.

(57) ABSTRACT

Bioerodible endoprostheses and methods of making the endoprostheses are disclosed. In some embodiments, an endoprosthesis includes a member including a bioerodible material, and an antioxidant carried by the member. Examples of antioxidants include phenols.

17 Claims, 7 Drawing Sheets

(56) References Cited

U.S. PATENT DOCUMENTS

| | | |
|---|---|---|
| 5,236,413 A | 8/1993 | Feiring |
| 5,236,447 A | 8/1993 | Kubo et al. |
| 5,270,086 A | 12/1993 | Hamlin |
| 5,279,292 A | 1/1994 | Baumann et al. |
| 5,290,585 A | 3/1994 | Elton |
| 5,292,558 A | 3/1994 | Heller et al. |
| 5,302,414 A | 4/1994 | Alkhimov et al. |
| 5,304,121 A | 4/1994 | Sahatjian |
| 5,304,195 A | 4/1994 | Twyford, Jr. et al. |
| 5,306,286 A | 4/1994 | Stack et al. |
| 5,314,453 A | 5/1994 | Jeutter |
| 5,322,520 A | 6/1994 | Milder |
| 5,342,348 A | 8/1994 | Kaplan |
| 5,348,553 A | 9/1994 | Whitney |
| 5,356,433 A | 10/1994 | Rowland et al. |
| 5,360,440 A | 11/1994 | Andersen |
| 5,366,504 A | 11/1994 | Andersen et al. |
| 5,380,298 A | 1/1995 | Zabetakis et al. |
| 5,383,935 A | 1/1995 | Shirkhanzadeh |
| 5,385,776 A | 1/1995 | Maxfield et al. |
| 5,397,307 A | 3/1995 | Goodin |
| 5,405,367 A | 4/1995 | Schulman et al. |
| 5,421,955 A | 6/1995 | Lau et al. |
| 5,439,446 A | 8/1995 | Barry |
| 5,443,458 A | 8/1995 | Eury |
| 5,443,496 A | 8/1995 | Schwartz et al. |
| 5,443,500 A | 8/1995 | Sigwart |
| 5,449,373 A | 9/1995 | Pinchasik et al. |
| 5,449,382 A | 9/1995 | Dayton |
| 5,458,627 A | 10/1995 | Baranowski, Jr. et al. |
| 5,462,575 A | 10/1995 | Del Corso |
| 5,464,450 A | 11/1995 | Buscemi et al. |
| 5,464,650 A | 11/1995 | Berg et al. |
| 5,468,574 A | 11/1995 | Ehrenberg et al. |
| 5,474,797 A | 12/1995 | Sioshansi et al. |
| 5,492,763 A | 2/1996 | Barry et al. |
| 5,500,013 A | 3/1996 | Buscemi et al. |
| 5,514,154 A | 5/1996 | Lau et al. |
| 5,527,337 A | 6/1996 | Stack et al. |
| 5,536,573 A | 7/1996 | Rubner et al. |
| 5,545,208 A | 8/1996 | Wolff et al. |
| 5,549,664 A | 8/1996 | Hirata et al. |
| 5,551,954 A | 9/1996 | Buscemi et al. |
| 5,578,075 A | 11/1996 | Dayton |
| 5,587,200 A | 12/1996 | Lorenz et al. |
| 5,587,507 A | 12/1996 | Kohn et al. |
| 5,591,222 A | 1/1997 | Susawa et al. |
| 5,591,224 A | 1/1997 | Schwartz et al. |
| 5,599,352 A | 2/1997 | Dinh et al. |
| 5,603,556 A | 2/1997 | Klink |
| 5,605,696 A | 2/1997 | Eury et al. |
| 5,607,463 A | 3/1997 | Schwartz et al. |
| 5,609,629 A | 3/1997 | Fearnot et al. |
| 5,614,549 A | 3/1997 | Greenwald et al. |
| 5,624,411 A | 4/1997 | Tuch |
| 5,628,787 A | 5/1997 | Mayer |
| 5,629,077 A | 5/1997 | Turnland et al. |
| 5,632,771 A | 5/1997 | Boatman et al. |
| 5,632,840 A | 5/1997 | Campbell |
| 5,649,951 A | 7/1997 | Davidson |
| 5,658,327 A | 8/1997 | Altman et al. |
| 5,672,242 A | 9/1997 | Jen |
| 5,674,192 A | 10/1997 | Sahatjian et al. |
| 5,674,242 A | 10/1997 | Phan |
| 5,676,685 A | 10/1997 | Razavi |
| 5,679,440 A | 10/1997 | Kubota |
| 5,690,670 A | 11/1997 | Davidson |
| 5,693,085 A | 12/1997 | Buirge et al. |
| 5,693,928 A | 12/1997 | Egitto et al. |
| 5,697,967 A | 12/1997 | Dinh et al. |
| 5,700,286 A | 12/1997 | Tartaglia et al. |
| 5,716,981 A | 2/1998 | Hunter et al. |
| 5,721,049 A | 2/1998 | Marcolongo et al. |
| 5,725,570 A | 3/1998 | Heath |
| 5,733,925 A | 3/1998 | Kunz et al. |
| 5,741,331 A | 4/1998 | Pinchuk |
| 5,744,515 A | 4/1998 | Clapper |
| 5,749,809 A | 5/1998 | Lin |
| 5,749,880 A | 5/1998 | Banas et al. |
| 5,758,562 A | 6/1998 | Thompson |
| 5,759,192 A | 6/1998 | Saunders |
| 5,761,775 A | 6/1998 | Legome et al. |
| 5,769,883 A | 6/1998 | Buscemi et al. |
| 5,769,884 A | 6/1998 | Solovay |
| 5,773,925 A | 6/1998 | Kimura et al. |
| 5,776,184 A | 7/1998 | Tuch |
| 5,779,904 A | 7/1998 | Ruderman et al. |
| 5,780,807 A | 7/1998 | Saunders |
| 5,788,626 A | 8/1998 | Thompson |
| 5,788,687 A | 8/1998 | Batich et al. |
| 5,788,979 A | 8/1998 | Alt et al. |
| 5,797,898 A | 8/1998 | Santini, Jr. et al. |
| 5,800,511 A | 9/1998 | Mayer |
| 5,815,904 A | 10/1998 | Clubb et al. |
| 5,817,046 A | 10/1998 | Glickman |
| 5,824,045 A | 10/1998 | Alt |
| 5,824,048 A | 10/1998 | Tuch |
| 5,824,077 A | 10/1998 | Mayer |
| 5,830,217 A | 11/1998 | Ryan |
| 5,833,715 A | 11/1998 | Vachon et al. |
| 5,837,007 A | 11/1998 | Altman et al. |
| 5,837,275 A | 11/1998 | Burrell et al. |
| 5,840,387 A | 11/1998 | Berlowitz-Tarrant et al. |
| 5,843,089 A | 12/1998 | Sahatjian et al. |
| 5,843,172 A | 12/1998 | Yan |
| 5,852,277 A | 12/1998 | Gustafson |
| 5,854,382 A | 12/1998 | Loomis |
| 5,858,556 A | 1/1999 | Eckert et al. |
| 5,869,140 A | 2/1999 | Blohowiak et al. |
| 5,873,904 A | 2/1999 | Ragheb et al. |
| 5,876,756 A | 3/1999 | Takada et al. |
| 5,879,697 A | 3/1999 | Ding et al. |
| 5,880,661 A | 3/1999 | Davidson et al. |
| 5,882,335 A | 3/1999 | Leone et al. |
| 5,891,108 A | 4/1999 | Leone et al. |
| 5,891,191 A | 4/1999 | Stinson |
| 5,899,935 A | 5/1999 | Ding |
| 5,902,266 A | 5/1999 | Leone et al. |
| 5,906,759 A | 5/1999 | Richter |
| 5,907,893 A | 6/1999 | Zadno-Azizi et al. |
| 5,919,126 A | 7/1999 | Armini |
| 5,922,005 A | 7/1999 | Richter et al. |
| 5,922,021 A | 7/1999 | Jang |
| 5,928,247 A | 7/1999 | Barry et al. |
| 5,928,279 A | 7/1999 | Shannon et al. |
| 5,935,506 A | 8/1999 | Schmitz et al. |
| 5,938,903 A | 8/1999 | Broderick |
| 5,941,843 A | 8/1999 | Atanasoska et al. |
| 5,951,458 A | 9/1999 | Hastings et al. |
| 5,951,881 A | 9/1999 | Rogers et al. |
| 5,954,706 A | 9/1999 | Sahatjian |
| 5,957,975 A | 9/1999 | Lafont et al. |
| 5,958,440 A | 9/1999 | Burrell et al. |
| 5,961,547 A | 10/1999 | Razavi |
| 5,968,091 A | 10/1999 | Pinchuk et al. |
| 5,968,092 A | 10/1999 | Buscemi et al. |
| 5,972,027 A | 10/1999 | Johnson |
| 5,972,192 A | 10/1999 | Dubin et al. |
| 5,976,169 A | 11/1999 | Imran |
| 5,976,454 A | 11/1999 | Sterzel et al. |
| 5,977,204 A | 11/1999 | Boyan et al. |
| 5,980,554 A | 11/1999 | Lenker et al. |
| 5,980,564 A | 11/1999 | Stinson |
| 5,980,566 A | 11/1999 | Alt et al. |
| 6,001,125 A | 12/1999 | Golds et al. |
| 6,013,591 A | 1/2000 | Ying et al. |
| 6,017,553 A | 1/2000 | Burrell et al. |
| 6,017,577 A | 1/2000 | Hostettler et al. |
| 6,021,347 A | 2/2000 | Herbst et al. |
| 6,025,036 A | 2/2000 | McGill et al. |
| 6,027,742 A | 2/2000 | Lee et al. |
| 6,034,295 A | 3/2000 | Rehberg et al. |
| 6,042,597 A | 3/2000 | Kveen et al. |
| 6,056,776 A | 5/2000 | Lau et al. |

(56) References Cited

U.S. PATENT DOCUMENTS

| | | |
|---|---|---|
| 6,063,101 A | 5/2000 | Jacobsen et al. |
| 6,071,305 A | 6/2000 | Brown et al. |
| 6,080,190 A | 6/2000 | Schwartz |
| 6,086,773 A | 7/2000 | Dufresne et al. |
| 6,096,070 A | 8/2000 | Ragheb et al. |
| 6,096,175 A | 8/2000 | Roth |
| 6,099,561 A | 8/2000 | Alt |
| 6,099,562 A | 8/2000 | Ding et al. |
| 6,106,473 A | 8/2000 | Violante et al. |
| 6,107,004 A | 8/2000 | Donadio, III |
| 6,117,592 A | 9/2000 | Hoshino et al. |
| 6,120,260 A | 9/2000 | Jirele |
| 6,120,535 A | 9/2000 | McDonald et al. |
| 6,120,660 A | 9/2000 | Chu et al. |
| 6,123,861 A | 9/2000 | Santini, Jr. et al. |
| 6,132,463 A | 10/2000 | Lee et al. |
| 6,139,573 A | 10/2000 | Sogard et al. |
| 6,139,574 A | 10/2000 | Vacanti et al. |
| 6,139,913 A | 10/2000 | Van Steenkiste et al. |
| 6,140,740 A | 10/2000 | Porat et al. |
| 6,143,370 A | 11/2000 | Panagiotou et al. |
| 6,153,252 A | 11/2000 | Hossainy et al. |
| 6,159,142 A | 12/2000 | Alt |
| 6,162,238 A | 12/2000 | Kaplan et al. |
| 6,164,284 A | 12/2000 | Schulman et al. |
| 6,165,211 A | 12/2000 | Thompson |
| 6,167,307 A | 12/2000 | Hess |
| 6,168,602 B1 | 1/2001 | Ryan |
| 6,170,488 B1 | 1/2001 | Spillman, Jr. et al. |
| 6,174,329 B1 | 1/2001 | Callol et al. |
| 6,174,330 B1 | 1/2001 | Stinson |
| 6,180,222 B1 | 1/2001 | Schulz et al. |
| 6,185,455 B1 | 2/2001 | Loeb et al. |
| 6,185,457 B1 | 2/2001 | Kroll et al. |
| 6,190,404 B1 | 2/2001 | Palmaz et al. |
| 6,192,271 B1 | 2/2001 | Hayman |
| 6,201,991 B1 | 3/2001 | Chekanov |
| 6,203,536 B1 | 3/2001 | Berg et al. |
| 6,206,914 B1 | 3/2001 | Soykan et al. |
| 6,206,915 B1 | 3/2001 | Fagan et al. |
| 6,206,916 B1 | 3/2001 | Furst |
| 6,212,434 B1 | 4/2001 | Scheiner |
| 6,214,037 B1 | 4/2001 | Mitchell et al. |
| 6,214,042 B1 | 4/2001 | Jacobsen et al. |
| 6,217,607 B1 | 4/2001 | Alt |
| 6,228,445 B1 | 5/2001 | Tverberg |
| 6,231,597 B1 | 5/2001 | Deem et al. |
| 6,240,616 B1 | 6/2001 | Yan |
| 6,241,762 B1 | 6/2001 | Shanley |
| 6,245,103 B1 | 6/2001 | Stinson |
| 6,245,104 B1 | 6/2001 | Alt |
| 6,249,952 B1 | 6/2001 | Ding |
| 6,251,136 B1 | 6/2001 | Guruwaiya et al. |
| 6,251,980 B1 | 6/2001 | Lan et al. |
| 6,253,252 B1 | 6/2001 | Schofield |
| 6,253,443 B1 | 7/2001 | Johnson |
| 6,254,632 B1 | 7/2001 | Wu et al. |
| 6,258,117 B1 | 7/2001 | Camrud et al. |
| 6,264,687 B1 | 7/2001 | Tomonto |
| 6,270,831 B2 | 8/2001 | Kumar et al. |
| 6,273,908 B1 | 8/2001 | Ndondo-Lay |
| 6,273,913 B1 | 8/2001 | Wright et al. |
| 6,277,078 B1 | 8/2001 | Porat et al. |
| 6,280,385 B1 | 8/2001 | Melzer et al. |
| 6,280,411 B1 | 8/2001 | Lennox |
| 6,283,386 B1 | 9/2001 | Van Steenkiste et al. |
| 6,287,331 B1 | 9/2001 | Heath |
| 6,287,332 B1 | 9/2001 | Bolz |
| 6,287,335 B1 | 9/2001 | Drasler et al. |
| 6,287,628 B1 | 9/2001 | Hossainy et al. |
| 6,290,721 B1 | 9/2001 | Heath |
| 6,290,722 B1 | 9/2001 | Wang |
| 6,291,076 B1 | 9/2001 | Nakatsugawa |
| 6,299,604 B1 | 10/2001 | Ragheb et al. |
| 6,299,755 B1 | 10/2001 | Richter |
| 6,306,144 B1 | 10/2001 | Sydney et al. |
| 6,309,414 B1 | 10/2001 | Rolando et al. |
| 6,312,463 B1 | 11/2001 | Rourke et al. |
| 6,315,708 B1 | 11/2001 | Salmon et al. |
| 6,323,146 B1 | 11/2001 | Pugh et al. |
| 6,325,825 B1 | 12/2001 | Kula et al. |
| 6,327,504 B1 | 12/2001 | Dolgin et al. |
| 6,331,312 B1 | 12/2001 | Lee et al. |
| 6,335,029 B1 | 1/2002 | Kamath et al. |
| 6,337,076 B1 | 1/2002 | Studin |
| 6,338,739 B1 | 1/2002 | Datta et al. |
| 6,342,507 B1 | 1/2002 | Naicker et al. |
| 6,344,055 B1 | 2/2002 | Shukov |
| 6,348,960 B1 | 2/2002 | Etori et al. |
| 6,358,276 B1 | 3/2002 | Edwin |
| 6,364,823 B1 | 4/2002 | Garibaldi et al. |
| 6,364,856 B1 | 4/2002 | Ding et al. |
| 6,364,903 B2 | 4/2002 | Tseng et al. |
| 6,366,808 B1 | 4/2002 | Schroeppel et al. |
| 6,368,658 B1 | 4/2002 | Schwarz et al. |
| 6,369,355 B1 | 4/2002 | Saunders |
| 6,375,826 B1 | 4/2002 | Wang et al. |
| 6,379,379 B1 | 4/2002 | Wang |
| 6,379,382 B1 | 4/2002 | Yang et al. |
| 6,379,383 B1 | 4/2002 | Palmaz et al. |
| 6,379,392 B1 | 4/2002 | Walak |
| 6,383,214 B1 | 5/2002 | Banas et al. |
| 6,387,121 B1 | 5/2002 | Alt |
| 6,387,124 B1 | 5/2002 | Buscemi et al. |
| 6,390,967 B1 | 5/2002 | Forman et al. |
| 6,391,033 B2 | 5/2002 | Ryan |
| 6,391,052 B2 | 5/2002 | Bulrge et al. |
| 6,395,326 B1 | 5/2002 | Castro et al. |
| 6,398,806 B1 | 6/2002 | You |
| 6,409,754 B1 | 6/2002 | Smith et al. |
| 6,419,692 B1 | 7/2002 | Yang et al. |
| 6,423,092 B2 | 7/2002 | Datta et al. |
| 6,425,855 B2 | 7/2002 | Tomonto |
| 6,436,133 B1 | 8/2002 | Furst et al. |
| 6,440,166 B1 | 8/2002 | Kolluri |
| 6,440,487 B1 | 8/2002 | Delfino et al. |
| 6,440,503 B1 | 8/2002 | Merdan et al. |
| 6,447,540 B1 | 9/2002 | Fontaine et al. |
| 6,451,871 B1 | 9/2002 | Winterton et al. |
| 6,458,153 B1 | 10/2002 | Bailey et al. |
| 6,468,304 B1 | 10/2002 | Dubois-Rande et al. |
| 6,471,721 B1 | 10/2002 | Dang |
| 6,471,980 B2 | 10/2002 | Sirhan et al. |
| 6,475,477 B1 | 11/2002 | Kohn et al. |
| 6,478,815 B1 | 11/2002 | Alt |
| 6,479,146 B1 | 11/2002 | Caruso et al. |
| 6,486,588 B2 | 11/2002 | Doron |
| 6,488,702 B1 | 12/2002 | Besselink |
| 6,491,666 B1 | 12/2002 | Santini, Jr. et al. |
| 6,491,720 B1 | 12/2002 | Vallana et al. |
| 6,492,096 B1 | 12/2002 | Liu et al. |
| 6,503,556 B2 | 1/2003 | Harish et al. |
| 6,503,921 B2 | 1/2003 | Naicker et al. |
| 6,506,437 B1 | 1/2003 | Harish et al. |
| 6,506,972 B1 | 1/2003 | Wang |
| 6,508,832 B1 | 1/2003 | Jalisi et al. |
| 6,514,283 B2 | 2/2003 | DiMatteo et al. |
| 6,517,571 B1 | 2/2003 | Brauker et al. |
| 6,517,888 B1 | 2/2003 | Weber |
| 6,524,274 B1 | 2/2003 | Rosenthal et al. |
| 6,524,334 B1 | 2/2003 | Thompson |
| 6,527,801 B1 | 3/2003 | Dutta |
| 6,527,938 B2 | 3/2003 | Bales et al. |
| 6,529,774 B1 | 3/2003 | Greene |
| 6,530,949 B2 | 3/2003 | Konya et al. |
| 6,530,951 B1 | 3/2003 | Bates et al. |
| 6,533,905 B2 | 3/2003 | Johnson et al. |
| 6,537,310 B1 | 3/2003 | Palmaz et al. |
| 6,537,312 B2 | 3/2003 | Datta et al. |
| 6,544,582 B1 | 4/2003 | Yoe |
| 6,545,097 B2 | 4/2003 | Pinchuk et al. |
| 6,549,811 B2 | 4/2003 | Stewart et al. |
| 6,554,854 B1 | 4/2003 | Flanagan |
| 6,558,422 B1 | 5/2003 | Baker et al. |

(56) References Cited

U.S. PATENT DOCUMENTS

| | | |
|---|---|---|
| 6,558,733 B1 | 5/2003 | Hossainy et al. |
| 6,565,602 B2 | 5/2003 | Rolando et al. |
| 6,569,489 B1 | 5/2003 | Li |
| 6,584,349 B1 | 6/2003 | Sage et al. |
| 6,585,764 B2 | 7/2003 | Wright et al. |
| 6,585,765 B1 | 7/2003 | Hossainy et al. |
| 6,586,705 B1 | 7/2003 | Schell |
| 6,589,286 B1 | 7/2003 | Litner |
| 6,599,558 B1 | 7/2003 | Al-Lamee et al. |
| 6,602,287 B1 | 8/2003 | Millare et al. |
| 6,607,598 B2 | 8/2003 | Schwarz et al. |
| 6,613,077 B2 | 9/2003 | Gilligan et al. |
| 6,613,083 B2 | 9/2003 | Alt |
| 6,613,432 B2 | 9/2003 | Zamora et al. |
| 6,616,765 B1 | 9/2003 | Castro et al. |
| 6,626,933 B1 | 9/2003 | Lau et al. |
| 6,626,936 B1 | 9/2003 | Stinson |
| 6,626,939 B1 | 9/2003 | Burnside et al. |
| 6,627,321 B1 | 9/2003 | Ellingsen et al. |
| 6,628,989 B1 | 9/2003 | Penner |
| 6,629,992 B2 | 10/2003 | Bigus et al. |
| 6,635,082 B1 | 10/2003 | Hossainy et al. |
| 6,638,302 B1 | 10/2003 | Curcio et al. |
| 6,641,607 B1 | 11/2003 | Hossainy et al. |
| 6,652,575 B2 | 11/2003 | Wang |
| 6,652,578 B2 | 11/2003 | Bailey et al. |
| 6,652,581 B1 | 11/2003 | Ding |
| 6,652,582 B1 | 11/2003 | Stinson |
| 6,660,034 B1 | 12/2003 | Mandrusov et al. |
| 6,663,662 B2 | 12/2003 | Pacetti et al. |
| 6,663,664 B1 | 12/2003 | Pacetti |
| 6,669,980 B2 | 12/2003 | Hansen |
| 6,673,105 B1 | 1/2004 | Chen |
| 6,673,385 B1 | 1/2004 | Ding et al. |
| 6,673,999 B1 | 1/2004 | Wang et al. |
| 6,676,987 B2 | 1/2004 | Zhong |
| 6,676,989 B2 | 1/2004 | Kirkpatrick et al. |
| 6,689,160 B1 | 2/2004 | Okuda et al. |
| 6,689,803 B2 | 2/2004 | Hunter |
| 6,695,865 B2 | 2/2004 | Boyle et al. |
| 6,696,666 B2 | 2/2004 | Merdan et al. |
| 6,696,667 B1 | 2/2004 | Flanagan |
| 6,699,281 B2 | 3/2004 | Vallana et al. |
| 6,699,282 B1 | 3/2004 | Sceusa |
| 6,709,379 B1 | 3/2004 | Brandau et al. |
| 6,709,397 B2 | 3/2004 | Taylor |
| 6,709,451 B1 | 3/2004 | Noble et al. |
| 6,710,053 B2 | 3/2004 | Naicker et al. |
| 6,712,844 B2 | 3/2004 | Pacetti |
| 6,712,845 B2 | 3/2004 | Hossainy |
| 6,713,671 B1 | 3/2004 | Wang et al. |
| 6,716,444 B1 | 4/2004 | Castro et al. |
| 6,719,987 B2 | 4/2004 | Burrell et al. |
| 6,720,402 B2 | 4/2004 | Langer et al. |
| 6,723,120 B2 | 4/2004 | Yan |
| 6,723,350 B2 | 4/2004 | Burrell et al. |
| 6,725,901 B1 | 4/2004 | Kramer et al. |
| 6,726,712 B1 | 4/2004 | Raeder-Devens |
| 6,730,117 B1 | 5/2004 | Tseng et al. |
| 6,730,120 B2 | 5/2004 | Berg et al. |
| 6,730,699 B2 | 5/2004 | Li et al. |
| 6,733,513 B2 | 5/2004 | Boyle et al. |
| 6,740,077 B1 | 5/2004 | Brandau et al. |
| 6,743,388 B2 | 6/2004 | Sridharan et al. |
| 6,752,826 B2 | 6/2004 | Holloway et al. |
| 6,752,829 B2 | 6/2004 | Kocur et al. |
| 6,753,071 B1 | 6/2004 | Pacetti |
| 6,758,859 B1 | 7/2004 | Dang et al. |
| 6,764,505 B1 | 7/2004 | Hossainy et al. |
| 6,764,579 B2 | 7/2004 | Veerasamy et al. |
| 6,764,709 B2 | 7/2004 | Flanagan |
| 6,765,144 B1 | 7/2004 | Wang et al. |
| 6,767,360 B1 | 7/2004 | Alt et al. |
| 6,770,086 B1 | 8/2004 | Girton |
| 6,770,729 B2 | 8/2004 | Van Antwerp |
| 6,774,278 B1 | 8/2004 | Ragheb et al. |
| 6,776,022 B2 | 8/2004 | Kula et al. |
| 6,776,094 B1 | 8/2004 | Whitesides et al. |
| 6,776,793 B2 | 8/2004 | Brown et al. |
| 6,780,424 B2 | 8/2004 | Claude |
| 6,783,543 B2 | 8/2004 | Jang |
| 6,790,228 B2 | 9/2004 | Hossainy et al. |
| 6,793,877 B1 | 9/2004 | Pettersen et al. |
| 6,796,435 B2 | 9/2004 | Izumi |
| 6,803,070 B2 | 10/2004 | Weber |
| 6,805,709 B1 | 10/2004 | Schaldach et al. |
| 6,805,898 B1 | 10/2004 | Wu et al. |
| 6,807,440 B2 | 10/2004 | Weber |
| RE38,653 E | 11/2004 | Igaki et al. |
| 6,815,609 B1 | 11/2004 | Wang et al. |
| 6,820,676 B2 | 11/2004 | Palmaz et al. |
| 6,827,737 B2 | 12/2004 | Hill et al. |
| 6,827,966 B2 | 12/2004 | Qiu et al. |
| 6,833,004 B2 | 12/2004 | Ishii et al. |
| 6,846,323 B2 | 1/2005 | Yip et al. |
| 6,846,841 B2 | 1/2005 | Hunter et al. |
| 6,847,837 B1 | 1/2005 | Melzer et al. |
| 6,849,085 B2 | 2/2005 | Marton |
| 6,849,089 B2 | 2/2005 | Stoll |
| 6,852,122 B2 | 2/2005 | Rush |
| 6,854,172 B2 | 2/2005 | Kaese et al. |
| 6,861,088 B2 | 3/2005 | Weber et al. |
| 6,865,810 B2 | 3/2005 | Stinson |
| 6,866,805 B2 | 3/2005 | Hong et al. |
| 6,869,443 B2 | 3/2005 | Buscemi et al. |
| 6,869,701 B1 | 3/2005 | Aita et al. |
| 6,875,227 B2 | 4/2005 | Yoon |
| 6,878,249 B2 | 4/2005 | Kouyama et al. |
| 6,884,429 B2 | 4/2005 | Koziak et al. |
| 6,887,270 B2 | 5/2005 | Miller et al. |
| 6,887,857 B2 | 5/2005 | Naimark et al. |
| 6,896,697 B1 | 5/2005 | Yip et al. |
| 6,899,731 B2 | 5/2005 | Li et al. |
| 6,899,914 B2 | 5/2005 | Schaldach et al. |
| 6,904,658 B2 | 6/2005 | Hines |
| 6,908,506 B2 | 6/2005 | Zimmermann |
| 6,908,622 B2 | 6/2005 | Barry et al. |
| 6,908,624 B2 | 6/2005 | Hossainy et al. |
| 6,913,617 B1 | 7/2005 | Reiss |
| 6,913,765 B2 | 7/2005 | Li et al. |
| 6,918,869 B2 | 7/2005 | Shaw et al. |
| 6,918,927 B2 | 7/2005 | Bates et al. |
| 6,921,390 B2 | 7/2005 | Bucay-Couto et al. |
| 6,923,996 B2 | 8/2005 | Epstein et al. |
| 6,926,735 B2 | 8/2005 | Henderson |
| 6,932,930 B2 | 8/2005 | DeSimone et al. |
| 6,936,066 B2 | 8/2005 | Palmaz et al. |
| 6,938,668 B2 | 9/2005 | Whitcher et al. |
| 6,939,320 B2 | 9/2005 | Lennox |
| 6,945,993 B2 | 9/2005 | Kveen et al. |
| 6,951,053 B2 | 10/2005 | Padilla et al. |
| 6,953,560 B1 | 10/2005 | Castro et al. |
| 6,953,594 B2 | 10/2005 | Lee et al. |
| 6,954,977 B2 | 10/2005 | Maguire et al. |
| 6,955,661 B1 | 10/2005 | Herweck et al. |
| 6,955,685 B2 | 10/2005 | Escamilla et al. |
| 6,962,822 B2 | 11/2005 | Hart et al. |
| 6,964,817 B2 | 11/2005 | Date et al. |
| 6,971,813 B2 | 12/2005 | Shekalim et al. |
| 6,972,130 B1 | 12/2005 | Lee et al. |
| 6,973,718 B2 | 12/2005 | Sheppard, Jr. et al. |
| 6,979,346 B1 | 12/2005 | Hossainy et al. |
| 6,979,347 B1 | 12/2005 | Wu et al. |
| 6,979,348 B2 | 12/2005 | Sundar |
| 6,981,986 B1 | 1/2006 | Brown et al. |
| 6,984,404 B1 | 1/2006 | Talton et al. |
| 6,986,899 B2 | 1/2006 | Hossainy et al. |
| 6,989,156 B2 | 1/2006 | Gillis |
| 6,991,709 B2 | 1/2006 | Gopalraja et al. |
| 7,001,421 B2 | 2/2006 | Cheng et al. |
| 7,004,968 B2 | 2/2006 | Lootz et al. |
| 7,011,670 B2 | 3/2006 | Radisch, Jr. |
| 7,011,678 B2 | 3/2006 | Tenerz et al. |
| 7,011,680 B2 | 3/2006 | Alt |

(56) References Cited

U.S. PATENT DOCUMENTS

| | | |
|---|---|---|
| 7,018,408 B2 | 3/2006 | Bailey et al. |
| 7,022,334 B1 | 4/2006 | Ding |
| 7,041,130 B2 | 5/2006 | Santini, Jr. |
| 7,048,767 B2 | 5/2006 | Namavar |
| 7,048,939 B2 | 5/2006 | Elkins et al. |
| 7,052,488 B2 | 5/2006 | Uhland |
| 7,056,338 B2 | 6/2006 | Shanley et al. |
| 7,056,339 B2 | 6/2006 | Elkins et al. |
| 7,060,051 B2 | 6/2006 | Palasis |
| 7,060,240 B2 | 6/2006 | Costa et al. |
| 7,063,748 B2 | 6/2006 | Talton |
| 7,067,606 B2 | 6/2006 | Mather et al. |
| 7,070,576 B2 | 7/2006 | O'Brien et al. |
| 7,078,108 B2 | 7/2006 | Zhang et al. |
| 7,099,091 B2 | 8/2006 | Taniguchi et al. |
| 7,101,391 B2 | 9/2006 | Scheuermann et al. |
| 7,101,394 B2 | 9/2006 | Hamm et al. |
| 7,105,018 B1 | 9/2006 | Yip et al. |
| 7,105,199 B2 | 9/2006 | Blinn et al. |
| 7,108,716 B2 | 9/2006 | Burnside et al. |
| 7,157,096 B2 | 1/2007 | Zhang et al. |
| 7,160,592 B2 | 1/2007 | Rypacek et al. |
| 7,163,715 B1 | 1/2007 | Kramer |
| 7,169,173 B2 | 1/2007 | Hossainy et al. |
| 7,169,178 B1 | 1/2007 | Santos et al. |
| 7,195,640 B2 | 3/2007 | Falotico et al. |
| 7,195,641 B2 | 3/2007 | Palmaz et al. |
| 7,198,675 B2 | 4/2007 | Fox et al. |
| 7,208,011 B2 | 4/2007 | Shanley et al. |
| 7,208,172 B2 | 4/2007 | Birdsall et al. |
| 7,220,816 B2 | 5/2007 | Pacetti |
| 7,226,475 B2 | 6/2007 | Lenz et al. |
| 7,229,471 B2 | 6/2007 | Gale et al. |
| 7,235,096 B1 | 6/2007 | Van Tassel et al. |
| 7,235,098 B2 | 6/2007 | Palmaz |
| 7,238,199 B2 | 7/2007 | Feldman et al. |
| 7,241,295 B2 | 7/2007 | Maguire |
| 7,244,272 B2 | 7/2007 | Dubson et al. |
| 7,261,732 B2 | 8/2007 | Justino |
| 7,261,735 B2 | 8/2007 | Llanos et al. |
| 7,267,960 B2 | 9/2007 | Galibert et al. |
| 7,279,174 B2 | 10/2007 | Pacetti |
| 7,279,175 B2 | 10/2007 | Chen |
| 7,294,409 B2 | 11/2007 | Lye et al. |
| 7,311,727 B2 | 12/2007 | Mazumder et al. |
| 7,323,189 B2 | 1/2008 | Pathak |
| RE40,122 E | 2/2008 | Thompson |
| 7,331,993 B2 | 2/2008 | White |
| 7,335,375 B2 | 2/2008 | Li et al. |
| 7,344,560 B2 | 3/2008 | Gregorich et al. |
| 7,344,563 B2 | 3/2008 | Vallana et al. |
| 7,393,589 B2 | 7/2008 | Aharonov et al. |
| 7,402,173 B2 | 7/2008 | Scheuermann et al. |
| 7,416,558 B2 | 8/2008 | Yip et al. |
| 7,432,327 B2 | 10/2008 | Glasgow et al. |
| 7,462,366 B2 | 12/2008 | Lanphere |
| 7,498,385 B2 | 3/2009 | Swetlin et al. |
| 7,507,433 B2 | 3/2009 | Weber |
| 7,537,610 B2 | 5/2009 | Reiss |
| 7,547,445 B2 | 6/2009 | Chudzik et al. |
| 7,563,277 B2 | 7/2009 | Case et al. |
| 7,637,941 B1 | 12/2009 | Manicka et al. |
| 7,651,527 B2 | 1/2010 | Krivoruchko et al. |
| 7,671,095 B2 | 3/2010 | Colson et al. |
| 7,691,401 B2 | 4/2010 | Castro et al. |
| 7,713,297 B2 | 5/2010 | Alt |
| 7,713,573 B2 | 5/2010 | Owens et al. |
| 7,722,805 B2 | 5/2010 | Hao et al. |
| 7,727,273 B2 | 6/2010 | Stinson et al. |
| 7,749,264 B2 | 7/2010 | Gregorich et al. |
| 7,758,635 B2 | 7/2010 | Parsonage |
| 7,771,773 B2 | 8/2010 | Namavar |
| 7,776,926 B1 | 8/2010 | Claude et al. |
| 7,906,147 B2 | 3/2011 | Hainfeld |
| 7,955,382 B2 | 6/2011 | Flanagan et al. |
| 7,981,150 B2 | 7/2011 | Scheuermann et al. |
| 7,985,252 B2 | 7/2011 | Radhakrishnan et al. |
| 7,988,192 B2 | 8/2011 | Numoto et al. |
| 7,998,192 B2 | 8/2011 | Atanasoska et al. |
| 8,133,278 B2 | 3/2012 | Atanasoska et al. |
| 8,158,728 B2 | 4/2012 | DeSimone et al. |
| 8,277,833 B2 | 10/2012 | Atanasoska et al. |
| 2001/0001834 A1 | 5/2001 | Palmaz et al. |
| 2001/0002000 A1 | 5/2001 | Kumar et al. |
| 2001/0002435 A1 | 5/2001 | Berg et al. |
| 2001/0013166 A1* | 8/2001 | Yan ........................... 29/527.2 |
| 2001/0021871 A1 | 9/2001 | Stinson |
| 2001/0021873 A1 | 9/2001 | Stinson |
| 2001/0027299 A1 | 10/2001 | Yang et al. |
| 2001/0029398 A1 | 10/2001 | Jadhav |
| 2001/0029660 A1 | 10/2001 | Johnson |
| 2001/0032011 A1 | 10/2001 | Stanford |
| 2001/0032013 A1 | 10/2001 | Marton |
| 2001/0032014 A1 | 10/2001 | Yang et al. |
| 2001/0044650 A1 | 11/2001 | Simso et al. |
| 2002/0000175 A1 | 1/2002 | Hintermaier et al. |
| 2002/0000406 A1 | 1/2002 | Izumi |
| 2002/0004060 A1* | 1/2002 | Heublein et al. ............... 424/422 |
| 2002/0007102 A1 | 1/2002 | Salmon et al. |
| 2002/0007209 A1 | 1/2002 | Schearder et al. |
| 2002/0010505 A1 | 1/2002 | Richter |
| 2002/0016623 A1 | 2/2002 | Kula et al. |
| 2002/0016624 A1 | 2/2002 | Patterson et al. |
| 2002/0028827 A1 | 3/2002 | Naicker et al. |
| 2002/0032477 A1 | 3/2002 | Helmus et al. |
| 2002/0035394 A1 | 3/2002 | Fierens et al. |
| 2002/0038146 A1 | 3/2002 | Harry |
| 2002/0042039 A1 | 4/2002 | Kim et al. |
| 2002/0049495 A1 | 4/2002 | Kutryk et al. |
| 2002/0051730 A1 | 5/2002 | Bodnar et al. |
| 2002/0051846 A1 | 5/2002 | Kirkpatrick et al. |
| 2002/0065553 A1 | 5/2002 | Weber |
| 2002/0082679 A1 | 6/2002 | Sirhan et al. |
| 2002/0087123 A1 | 7/2002 | Hossainy et al. |
| 2002/0090313 A1 | 7/2002 | Wang et al. |
| 2002/0091375 A1 | 7/2002 | Sahatjian et al. |
| 2002/0098278 A1 | 7/2002 | Bates et al. |
| 2002/0099434 A1 | 7/2002 | Buscemi et al. |
| 2002/0099438 A1 | 7/2002 | Furst |
| 2002/0103527 A1 | 8/2002 | Kocur et al. |
| 2002/0103528 A1 | 8/2002 | Schaldach et al. |
| 2002/0111694 A1 | 8/2002 | Ellingsen et al. |
| 2002/0121497 A1 | 9/2002 | Tomonto |
| 2002/0123801 A1 | 9/2002 | Pacetti et al. |
| 2002/0133222 A1 | 9/2002 | Das |
| 2002/0133224 A1 | 9/2002 | Bajgar et al. |
| 2002/0138100 A1 | 9/2002 | Stoll et al. |
| 2002/0138131 A1 | 9/2002 | Solovay et al. |
| 2002/0138136 A1 | 9/2002 | Chandresekaran et al. |
| 2002/0138154 A1 | 9/2002 | Li et al. |
| 2002/0144757 A1 | 10/2002 | Craig et al. |
| 2002/0151964 A1 | 10/2002 | Smith et al. |
| 2002/0155212 A1 | 10/2002 | Hossainy |
| 2002/0165265 A1 | 11/2002 | Hunter et al. |
| 2002/0165578 A1 | 11/2002 | Sawitowski et al. |
| 2002/0165600 A1 | 11/2002 | Banas et al. |
| 2002/0165607 A1 | 11/2002 | Alt |
| 2002/0169493 A1 | 11/2002 | Widenhouse et al. |
| 2002/0177042 A1 | 11/2002 | Amendola |
| 2002/0178570 A1 | 12/2002 | Sogard et al. |
| 2002/0182241 A1 | 12/2002 | Borenstein et al. |
| 2002/0183581 A1 | 12/2002 | Yoe et al. |
| 2002/0187260 A1 | 12/2002 | Sheppard, Jr. et al. |
| 2002/0193336 A1 | 12/2002 | Elkins et al. |
| 2002/0193682 A1 | 12/2002 | Torchia et al. |
| 2002/0193869 A1 | 12/2002 | Dang |
| 2002/0197178 A1 | 12/2002 | Yan |
| 2002/0198601 A1 | 12/2002 | Bales et al. |
| 2003/0003127 A1 | 1/2003 | Brown et al. |
| 2003/0003220 A1 | 1/2003 | Zhong et al. |
| 2003/0004563 A1 | 1/2003 | Jackson et al. |
| 2003/0004564 A1 | 1/2003 | Elkins et al. |
| 2003/0009214 A1 | 1/2003 | Shanley |
| 2003/0018380 A1 | 1/2003 | Craig et al. |

(56) References Cited

U.S. PATENT DOCUMENTS

| | | |
|---|---|---|
| 2003/0018381 A1 | 1/2003 | Whitcher et al. |
| 2003/0023300 A1 | 1/2003 | Bailey et al. |
| 2003/0028242 A1 | 2/2003 | Vallana et al. |
| 2003/0028243 A1 | 2/2003 | Bates et al. |
| 2003/0032892 A1 | 2/2003 | Erlach et al. |
| 2003/0033007 A1 | 2/2003 | Sirhan et al. |
| 2003/0044446 A1 | 3/2003 | Moro et al. |
| 2003/0044596 A1 | 3/2003 | Lazarov et al. |
| 2003/0050687 A1 | 3/2003 | Schwade et al. |
| 2003/0050692 A1 | 3/2003 | Sirhan et al. |
| 2003/0059640 A1 | 3/2003 | Marton et al. |
| 2003/0060871 A1 | 3/2003 | Hill et al. |
| 2003/0060873 A1 | 3/2003 | Gertner et al. |
| 2003/0064095 A1 | 4/2003 | Martin et al. |
| 2003/0068355 A1 | 4/2003 | Shanley et al. |
| 2003/0069631 A1 | 4/2003 | Stoll |
| 2003/0074053 A1 | 4/2003 | Palmaz et al. |
| 2003/0077200 A1 | 4/2003 | Craig et al. |
| 2003/0077310 A1 | 4/2003 | Pathak et al. |
| 2003/0083614 A1 | 5/2003 | Eisert |
| 2003/0083646 A1 | 5/2003 | Sirhan et al. |
| 2003/0083731 A1 | 5/2003 | Kramer et al. |
| 2003/0087024 A1 | 5/2003 | Flanagan |
| 2003/0088307 A1 | 5/2003 | Shulze et al. |
| 2003/0088312 A1 | 5/2003 | Kopia et al. |
| 2003/0099684 A1 | 5/2003 | Domb |
| 2003/0100815 A1 | 5/2003 | Da Silva et al. |
| 2003/0100830 A1 | 5/2003 | Zhong et al. |
| 2003/0104030 A1 | 6/2003 | Igaki et al. |
| 2003/0105511 A1 | 6/2003 | Welsh et al. |
| 2003/0108659 A1 | 6/2003 | Bales et al. |
| 2003/0114917 A1 | 6/2003 | Holloway et al. |
| 2003/0114921 A1 | 6/2003 | Yoon |
| 2003/0118692 A1 | 6/2003 | Wang et al. |
| 2003/0120339 A1 | 6/2003 | Banik et al. |
| 2003/0124055 A1 | 7/2003 | Li et al. |
| 2003/0125803 A1 | 7/2003 | Vallana |
| 2003/0130718 A1 | 7/2003 | Palmas et al. |
| 2003/0139799 A1 | 7/2003 | Ley et al. |
| 2003/0143330 A1 | 7/2003 | Loomis et al. |
| 2003/0144728 A1 | 7/2003 | Scheuermann et al. |
| 2003/0150380 A1 | 8/2003 | Yoe |
| 2003/0153901 A1 | 8/2003 | Herweck et al. |
| 2003/0153971 A1 | 8/2003 | Chandrasekaran |
| 2003/0158598 A1 | 8/2003 | Ashton et al. |
| 2003/0170605 A1 | 9/2003 | Long et al. |
| 2003/0181973 A1 | 9/2003 | Sahota |
| 2003/0181975 A1 | 9/2003 | Ishii et al. |
| 2003/0185895 A1 | 10/2003 | Lanphere |
| 2003/0190406 A1 | 10/2003 | Hossainy et al. |
| 2003/0195613 A1 | 10/2003 | Curcio et al. |
| 2003/0199993 A1 | 10/2003 | Gellman et al. |
| 2003/0204239 A1* | 10/2003 | Carlyle et al. ............... 623/1.11 |
| 2003/0211135 A1 | 11/2003 | Greenhalgh et al. |
| 2003/0216803 A1 | 11/2003 | Ledergerber |
| 2003/0219562 A1 | 11/2003 | Rypacek et al. |
| 2003/0221307 A1 | 12/2003 | Kaese et al. |
| 2003/0228523 A1 | 12/2003 | DeLongchamp et al. |
| 2003/0236513 A1 | 12/2003 | Schwarz et al. |
| 2004/0000046 A1 | 1/2004 | Stinson |
| 2004/0000540 A1 | 1/2004 | Soboyejo et al. |
| 2004/0004063 A1 | 1/2004 | Merdan |
| 2004/0006382 A1 | 1/2004 | Sohier |
| 2004/0018296 A1 | 1/2004 | Castro et al. |
| 2004/0019376 A1 | 1/2004 | Alt |
| 2004/0022939 A1 | 2/2004 | Kim et al. |
| 2004/0024448 A1 | 2/2004 | Chang et al. |
| 2004/0029303 A1 | 2/2004 | Hart et al. |
| 2004/0030218 A1 | 2/2004 | Kocur et al. |
| 2004/0030377 A1 | 2/2004 | Dubson et al. |
| 2004/0034409 A1 | 2/2004 | Heublein et al. |
| 2004/0039438 A1 | 2/2004 | Alt |
| 2004/0039441 A1 | 2/2004 | Rowland et al. |
| 2004/0044397 A1 | 3/2004 | Stinson |
| 2004/0047980 A1 | 3/2004 | Pacetti et al. |
| 2004/0059407 A1 | 3/2004 | Escamilla et al. |
| 2004/0059409 A1 | 3/2004 | Stenzel |
| 2004/0067301 A1 | 4/2004 | Ding |
| 2004/0071861 A1 | 4/2004 | Mandrusov et al. |
| 2004/0073155 A1 | 4/2004 | Laufer et al. |
| 2004/0073284 A1 | 4/2004 | Bates et al. |
| 2004/0073293 A1 | 4/2004 | Thompson |
| 2004/0073297 A1 | 4/2004 | Rohde et al. |
| 2004/0073298 A1 | 4/2004 | Hossainy |
| 2004/0078071 A1 | 4/2004 | Escamilla et al. |
| 2004/0082682 A1 | 4/2004 | Loomis et al. |
| 2004/0088038 A1 | 5/2004 | Dehnad et al. |
| 2004/0088041 A1 | 5/2004 | Stanford |
| 2004/0093071 A1 | 5/2004 | Jang |
| 2004/0093075 A1 | 5/2004 | Kuehne |
| 2004/0093076 A1 | 5/2004 | White et al. |
| 2004/0098089 A1 | 5/2004 | Weber |
| 2004/0098108 A1 | 5/2004 | Harder et al. |
| 2004/0098119 A1 | 5/2004 | Wang |
| 2004/0106975 A1 | 6/2004 | Solovay et al. |
| 2004/0106984 A1 | 6/2004 | Stinson |
| 2004/0106985 A1 | 6/2004 | Jang |
| 2004/0111150 A1 | 6/2004 | Berg et al. |
| 2004/0116999 A1 | 6/2004 | Ledergerber |
| 2004/0117005 A1 | 6/2004 | Gadde et al. |
| 2004/0117008 A1 | 6/2004 | Wnendt et al. |
| 2004/0122504 A1 | 6/2004 | Hogendijk |
| 2004/0126566 A1 | 7/2004 | Axen et al. |
| 2004/0133270 A1 | 7/2004 | Grandt |
| 2004/0134886 A1 | 7/2004 | Wagner et al. |
| 2004/0137039 A1 | 7/2004 | Sukhishvili et al. |
| 2004/0138738 A1 | 7/2004 | Stinson |
| 2004/0142014 A1 | 7/2004 | Litvack et al. |
| 2004/0143317 A1 | 7/2004 | Stinson et al. |
| 2004/0143321 A1 | 7/2004 | Litvack et al. |
| 2004/0148010 A1 | 7/2004 | Rush |
| 2004/0148015 A1 | 7/2004 | Lye et al. |
| 2004/0153138 A1 | 8/2004 | Murphy |
| 2004/0157073 A1 | 8/2004 | Burrell et al. |
| 2004/0158308 A1 | 8/2004 | Hogendijk et al. |
| 2004/0158310 A1 | 8/2004 | Weber et al. |
| 2004/0167572 A1 | 8/2004 | Roth et al. |
| 2004/0167609 A1 | 8/2004 | Majercak |
| 2004/0167612 A1 | 8/2004 | Grignani et al. |
| 2004/0172124 A1 | 9/2004 | Vallana et al. |
| 2004/0181252 A1 | 9/2004 | Boyle et al. |
| 2004/0181275 A1 | 9/2004 | Noble et al. |
| 2004/0181276 A1 | 9/2004 | Brown et al. |
| 2004/0181278 A1 | 9/2004 | Tseng et al. |
| 2004/0182511 A1 | 9/2004 | Rakos et al. |
| 2004/0186553 A1 | 9/2004 | Yan |
| 2004/0191293 A1 | 9/2004 | Claude |
| 2004/0191404 A1 | 9/2004 | Hossainy et al. |
| 2004/0202692 A1 | 10/2004 | Shanley et al. |
| 2004/0204750 A1 | 10/2004 | Dinh |
| 2004/0211362 A1 | 10/2004 | Castro et al. |
| 2004/0219214 A1 | 11/2004 | Gravett et al. |
| 2004/0220510 A1 | 11/2004 | Koullick et al. |
| 2004/0220659 A1 | 11/2004 | Girton |
| 2004/0220660 A1 | 11/2004 | Shanley et al. |
| 2004/0220662 A1 | 11/2004 | Dang et al. |
| 2004/0224001 A1 | 11/2004 | Pacetti et al. |
| 2004/0225346 A1 | 11/2004 | Mazumder et al. |
| 2004/0228905 A1 | 11/2004 | Greenspan et al. |
| 2004/0230176 A1 | 11/2004 | Shanahan et al. |
| 2004/0230225 A1 | 11/2004 | Penner et al. |
| 2004/0230290 A1 | 11/2004 | Weber et al. |
| 2004/0230293 A1 | 11/2004 | Yip et al. |
| 2004/0234737 A1 | 11/2004 | Pacetti |
| 2004/0236415 A1 | 11/2004 | Thomas |
| 2004/0236416 A1 | 11/2004 | Falotico |
| 2004/0237282 A1 | 12/2004 | Hines |
| 2004/0242106 A1 | 12/2004 | Rabasco et al. |
| 2004/0243217 A1 | 12/2004 | Andersen |
| 2004/0243237 A1 | 12/2004 | Unwin et al. |
| 2004/0243241 A1 | 12/2004 | Istephanous et al. |
| 2004/0247671 A1 | 12/2004 | Prescott et al. |
| 2004/0249440 A1 | 12/2004 | Bucker et al. |
| 2004/0249443 A1 | 12/2004 | Shanley et al. |

(56) References Cited

U.S. PATENT DOCUMENTS

| | | |
|---|---|---|
| 2004/0249444 A1 | 12/2004 | Reiss |
| 2004/0249445 A1 | 12/2004 | Rosenthal et al. |
| 2004/0249449 A1 | 12/2004 | Shanley et al. |
| 2004/0254419 A1 | 12/2004 | Wang et al. |
| 2004/0254635 A1 | 12/2004 | Shanley et al. |
| 2005/0004661 A1 | 1/2005 | Lewis et al. |
| 2005/0010275 A1 | 1/2005 | Sahatjian |
| 2005/0010279 A1 | 1/2005 | Tenerz et al. |
| 2005/0015142 A1 | 1/2005 | Austin et al. |
| 2005/0019265 A1 | 1/2005 | Hammer et al. |
| 2005/0019371 A1 | 1/2005 | Anderson et al. |
| 2005/0021127 A1 | 1/2005 | Kawula |
| 2005/0021128 A1 | 1/2005 | Nakahama et al. |
| 2005/0022627 A1 | 2/2005 | Chen |
| 2005/0025804 A1 | 2/2005 | Heller |
| 2005/0027350 A1 | 2/2005 | Momma et al. |
| 2005/0033407 A1 | 2/2005 | Weber et al. |
| 2005/0033411 A1 | 2/2005 | Wu et al. |
| 2005/0033412 A1 | 2/2005 | Wu et al. |
| 2005/0033417 A1 | 2/2005 | Borges et al. |
| 2005/0037047 A1 | 2/2005 | Song |
| 2005/0037050 A1 | 2/2005 | Weber |
| 2005/0038134 A1 | 2/2005 | Loomis et al. |
| 2005/0038501 A1 | 2/2005 | Moore, Jr. et al. |
| 2005/0042288 A1 | 2/2005 | Koblish et al. |
| 2005/0042440 A1 | 2/2005 | Bach et al. |
| 2005/0055044 A1 | 3/2005 | Kangas |
| 2005/0055080 A1 | 3/2005 | Istephanous et al. |
| 2005/0055085 A1 | 3/2005 | Rivron et al. |
| 2005/0060020 A1 | 3/2005 | Jenson |
| 2005/0060021 A1 | 3/2005 | O'Brien et al. |
| 2005/0064088 A1 | 3/2005 | Fredrickson |
| 2005/0069630 A1 | 3/2005 | Fox et al. |
| 2005/0070989 A1 | 3/2005 | Lye et al. |
| 2005/0070990 A1 | 3/2005 | Stinson |
| 2005/0070996 A1 | 3/2005 | Dinh et al. |
| 2005/0071016 A1 | 3/2005 | Hausdorf et al. |
| 2005/0072544 A1 | 4/2005 | Palmaz et al. |
| 2005/0074479 A1 | 4/2005 | Weber et al. |
| 2005/0074545 A1 | 4/2005 | Thomas |
| 2005/0075714 A1 | 4/2005 | Cheng et al. |
| 2005/0077305 A1 | 4/2005 | Guevara |
| 2005/0079132 A1 | 4/2005 | Wang et al. |
| 2005/0079199 A1 | 4/2005 | Heruth et al. |
| 2005/0079356 A1 | 4/2005 | Rathenow et al. |
| 2005/0092615 A1 | 5/2005 | Birdsall et al. |
| 2005/0096731 A1 | 5/2005 | Looi et al. |
| 2005/0100577 A1 | 5/2005 | Parker et al. |
| 2005/0100609 A1 | 5/2005 | Claude |
| 2005/0102025 A1 | 5/2005 | Laroche et al. |
| 2005/0106212 A1 | 5/2005 | Gertner et al. |
| 2005/0107869 A1 | 5/2005 | Sirhan et al. |
| 2005/0107870 A1 | 5/2005 | Wang et al. |
| 2005/0113936 A1 | 5/2005 | Brustad et al. |
| 2005/0119723 A1 | 6/2005 | Peacock |
| 2005/0119725 A1 | 6/2005 | Wang et al. |
| 2005/0129727 A1 | 6/2005 | Weber et al. |
| 2005/0129731 A1 | 6/2005 | Horres et al. |
| 2005/0131509 A1 | 6/2005 | Atanassoska et al. |
| 2005/0131521 A1 | 6/2005 | Marton |
| 2005/0131522 A1 | 6/2005 | Stinson et al. |
| 2005/0131527 A1 | 6/2005 | Pathak |
| 2005/0131528 A1 | 6/2005 | Buscemi et al. |
| 2005/0136090 A1 | 6/2005 | Falotico et al. |
| 2005/0137677 A1 | 6/2005 | Rush |
| 2005/0137679 A1 | 6/2005 | Changelian et al. |
| 2005/0137684 A1 | 6/2005 | Changelian et al. |
| 2005/0149169 A1 | 7/2005 | Wang et al. |
| 2005/0149170 A1 | 7/2005 | Tassel et al. |
| 2005/0149175 A1 | 7/2005 | Hunter et al. |
| 2005/0149177 A1 | 7/2005 | Weber et al. |
| 2005/0159804 A1 | 7/2005 | Lad et al. |
| 2005/0159805 A1 | 7/2005 | Weber et al. |
| 2005/0159809 A1 | 7/2005 | Hezi-Yamit et al. |
| 2005/0160600 A1 | 7/2005 | Bien et al. |
| 2005/0163821 A1 | 7/2005 | Sung et al. |
| 2005/0163954 A1 | 7/2005 | Shaw |
| 2005/0165301 A1 | 7/2005 | Smith et al. |
| 2005/0165468 A1 | 7/2005 | Marton |
| 2005/0165470 A1 | 7/2005 | Weber |
| 2005/0169969 A1 | 8/2005 | Li et al. |
| 2005/0171595 A1 | 8/2005 | Feldman et al. |
| 2005/0177226 A1 | 8/2005 | Banik et al. |
| 2005/0180919 A1 | 8/2005 | Tedeschi |
| 2005/0182361 A1 | 8/2005 | Lennox |
| 2005/0182478 A1 | 8/2005 | Holman et al. |
| 2005/0186250 A1 | 8/2005 | Gertner et al. |
| 2005/0187605 A1 | 8/2005 | Greenhalgh et al. |
| 2005/0187611 A1 | 8/2005 | Ding et al. |
| 2005/0187615 A1 | 8/2005 | Williams et al. |
| 2005/0192657 A1 | 9/2005 | Colen et al. |
| 2005/0192662 A1 | 9/2005 | Ward |
| 2005/0192664 A1 | 9/2005 | Eisert |
| 2005/0196424 A1 | 9/2005 | Chappa |
| 2005/0208098 A1 | 9/2005 | Castro et al. |
| 2005/0208100 A1 | 9/2005 | Weber et al. |
| 2005/0209680 A1 | 9/2005 | Gale et al. |
| 2005/0209681 A1 | 9/2005 | Curcio et al. |
| 2005/0211680 A1 | 9/2005 | Li et al. |
| 2005/0214951 A1 | 9/2005 | Nahm et al. |
| 2005/0216074 A1 | 9/2005 | Sahatjian |
| 2005/0216075 A1 | 9/2005 | Wang et al. |
| 2005/0220836 A1* | 10/2005 | Falotico et al. .............. 424/423 |
| 2005/0220853 A1 | 10/2005 | Dao et al. |
| 2005/0221072 A1 | 10/2005 | Dubrow et al. |
| 2005/0222671 A1 | 10/2005 | Schaeffer et al. |
| 2005/0228477 A1 | 10/2005 | Grainger et al. |
| 2005/0228483 A1 | 10/2005 | Kaplan et al. |
| 2005/0228491 A1 | 10/2005 | Snyder et al. |
| 2005/0232968 A1 | 10/2005 | Palmaz et al. |
| 2005/0233965 A1 | 10/2005 | Schwartz et al. |
| 2005/0234538 A1 | 10/2005 | Litvack et al. |
| 2005/0240100 A1 | 10/2005 | Wang et al. |
| 2005/0240280 A1 | 10/2005 | Aliski et al. |
| 2005/0244459 A1 | 11/2005 | DeWitt et al. |
| 2005/0251245 A1 | 11/2005 | Sieradzki et al. |
| 2005/0251249 A1 | 11/2005 | Sahatjian |
| 2005/0252893 A1 | 11/2005 | Shapovalov et al. |
| 2005/0255707 A1 | 11/2005 | Hart et al. |
| 2005/0261760 A1 | 11/2005 | Weber |
| 2005/0266039 A1 | 12/2005 | Weber |
| 2005/0266040 A1 | 12/2005 | Gerberding |
| 2005/0266041 A1 | 12/2005 | Gerold et al. |
| 2005/0267560 A1 | 12/2005 | Bates |
| 2005/0267561 A1 | 12/2005 | Jones et al. |
| 2005/0271703 A1 | 12/2005 | Anderson et al. |
| 2005/0271706 A1 | 12/2005 | Anderson et al. |
| 2005/0276837 A1 | 12/2005 | Anderson et al. |
| 2005/0278016 A1 | 12/2005 | Welsh et al. |
| 2005/0278021 A1 | 12/2005 | Bates et al. |
| 2005/0281863 A1 | 12/2005 | Anderson et al. |
| 2005/0283224 A1 | 12/2005 | King |
| 2005/0283229 A1 | 12/2005 | Dugan et al. |
| 2005/0287188 A1 | 12/2005 | Anderson et al. |
| 2005/0288481 A1 | 12/2005 | OesNoyer et al. |
| 2006/0002979 A1 | 1/2006 | Ashammakhi et al. |
| 2006/0009839 A1 | 1/2006 | Tan |
| 2006/0013850 A1 | 1/2006 | Domb |
| 2006/0014039 A1 | 1/2006 | Zhang et al. |
| 2006/0015175 A1 | 1/2006 | Palmaz et al. |
| 2006/0015361 A1 | 1/2006 | Sattler et al. |
| 2006/0020742 A1 | 1/2006 | Au et al. |
| 2006/0025848 A1 | 2/2006 | Weber et al. |
| 2006/0035026 A1 | 2/2006 | Atanassoska et al. |
| 2006/0036281 A1 | 2/2006 | Patterson et al. |
| 2006/0036311 A1 | 2/2006 | Nakayama et al. |
| 2006/0038027 A1 | 2/2006 | O'Connor et al. |
| 2006/0040388 A1 | 2/2006 | Bromberg et al. |
| 2006/0041182 A1 | 2/2006 | Forbes et al. |
| 2006/0051397 A1 | 3/2006 | Maier et al. |
| 2006/0052744 A1 | 3/2006 | Weber |
| 2006/0052863 A1 | 3/2006 | Harder et al. |
| 2006/0052864 A1 | 3/2006 | Harder et al. |
| 2006/0058868 A1 | 3/2006 | Gale et al. |

(56) References Cited

U.S. PATENT DOCUMENTS

| | | |
|---|---|---|
| 2006/0062820 A1 | 3/2006 | Gertner et al. |
| 2006/0064160 A1 | 3/2006 | Gerold et al. |
| 2006/0067908 A1 | 3/2006 | Ding |
| 2006/0069427 A1 | 3/2006 | Savage et al. |
| 2006/0074480 A1 | 4/2006 | Bales et al. |
| 2006/0075092 A1 | 4/2006 | Kidokoro |
| 2006/0079958 A1 | 4/2006 | Stratford et al. |
| 2006/0085062 A1 | 4/2006 | Lee et al. |
| 2006/0085065 A1 | 4/2006 | Krause et al. |
| 2006/0088566 A1 | 4/2006 | Parsonage et al. |
| 2006/0088567 A1 | 4/2006 | Warner et al. |
| 2006/0088653 A1 | 4/2006 | Chappa et al. |
| 2006/0088666 A1 | 4/2006 | Kobrin et al. |
| 2006/0100696 A1 | 5/2006 | Atanasoska et al. |
| 2006/0115512 A1 | 6/2006 | Peacock et al. |
| 2006/0118236 A1 | 6/2006 | House et al. |
| 2006/0121080 A1 | 6/2006 | Lye et al. |
| 2006/0122694 A1 | 6/2006 | Stinson et al. |
| 2006/0122697 A1 | 6/2006 | Shanley et al. |
| 2006/0124472 A1 | 6/2006 | Rokicki |
| 2006/0127266 A1 | 6/2006 | Miura et al. |
| 2006/0129215 A1 | 6/2006 | Helmus et al. |
| 2006/0129222 A1 | 6/2006 | Stinson |
| 2006/0129225 A1 | 6/2006 | Kopia et al. |
| 2006/0136048 A1 | 6/2006 | Pacetti et al. |
| 2006/0136051 A1 | 6/2006 | Furst et al. |
| 2006/0141156 A1 | 6/2006 | Viel et al. |
| 2006/0149352 A1 | 7/2006 | Schlun |
| 2006/0153729 A1 | 7/2006 | Stinson et al. |
| 2006/0155361 A1 | 7/2006 | Schomig et al. |
| 2006/0167543 A1 | 7/2006 | Bailey et al. |
| 2006/0177480 A1 | 8/2006 | Sung et al. |
| 2006/0178727 A1 | 8/2006 | Richter |
| 2006/0184235 A1 | 8/2006 | Rivron et al. |
| 2006/0193886 A1 | 8/2006 | Owens et al. |
| 2006/0193887 A1 | 8/2006 | Owens et al. |
| 2006/0193888 A1 | 8/2006 | Lye et al. |
| 2006/0193889 A1 | 8/2006 | Spradlin et al. |
| 2006/0193890 A1 | 8/2006 | Owens et al. |
| 2006/0193892 A1 | 8/2006 | Furst et al. |
| 2006/0195142 A1 | 8/2006 | Shalaby |
| 2006/0198869 A1 | 9/2006 | Furst et al. |
| 2006/0199876 A1 | 9/2006 | Troczynski et al. |
| 2006/0200229 A1 | 9/2006 | Burgermeister et al. |
| 2006/0200231 A1 | 9/2006 | O'Brien et al. |
| 2006/0200232 A1 | 9/2006 | Phaneuf et al. |
| 2006/0200233 A1 | 9/2006 | Kujawski |
| 2006/0204441 A1 | 9/2006 | Atala et al. |
| 2006/0204445 A1 | 9/2006 | Atala et al. |
| 2006/0210595 A1 | 9/2006 | Singhvi et al. |
| 2006/0212108 A1 | 9/2006 | Tittelbach |
| 2006/0222679 A1 | 10/2006 | Shanley et al. |
| 2006/0222844 A1 | 10/2006 | Stinson |
| 2006/0224237 A1 | 10/2006 | Furst et al. |
| 2006/0229711 A1 | 10/2006 | Yan et al. |
| 2006/0229713 A1 | 10/2006 | Shanley et al. |
| 2006/0230476 A1 | 10/2006 | Atanasoska et al. |
| 2006/0233941 A1 | 10/2006 | Olson |
| 2006/0241739 A1 | 10/2006 | Besselink et al. |
| 2006/0251701 A1 | 11/2006 | Lynn et al. |
| 2006/0259133 A1 | 11/2006 | Sowinski et al. |
| 2006/0264138 A1 | 11/2006 | Sowinski et al. |
| 2006/0271156 A1 | 11/2006 | Ledergerber |
| 2006/0271168 A1 | 11/2006 | Kleine et al. |
| 2006/0271169 A1 | 11/2006 | Lye et al. |
| 2006/0271192 A1 | 11/2006 | Olsen et al. |
| 2006/0275554 A1 | 12/2006 | Zhao et al. |
| 2006/0276877 A1 | 12/2006 | Owens et al. |
| 2006/0276878 A1 | 12/2006 | Owens et al. |
| 2006/0276879 A1 | 12/2006 | Lye et al. |
| 2006/0276884 A1 | 12/2006 | Lye et al. |
| 2006/0276885 A1 | 12/2006 | Lye et al. |
| 2006/0280770 A1 | 12/2006 | Hossainy et al. |
| 2006/0287709 A1 | 12/2006 | Rao |
| 2006/0287710 A1 | 12/2006 | Lendlein et al. |
| 2006/0292388 A1 | 12/2006 | Palumbo et al. |
| 2007/0003589 A1 | 1/2007 | Astafieva et al. |
| 2007/0003596 A1 | 1/2007 | Tittelbach et al. |
| 2007/0020306 A1 | 1/2007 | Schultheiss |
| 2007/0027532 A1 | 2/2007 | Wang et al. |
| 2007/0032858 A1 | 2/2007 | Santos et al. |
| 2007/0032862 A1 | 2/2007 | Weber et al. |
| 2007/0032864 A1 | 2/2007 | Furst et al. |
| 2007/0034615 A1 | 2/2007 | Kleine |
| 2007/0036905 A1 | 2/2007 | Kramer |
| 2007/0038176 A1 | 2/2007 | Weber et al. |
| 2007/0038289 A1 | 2/2007 | Nishide et al. |
| 2007/0038290 A1 | 2/2007 | Huang et al. |
| 2007/0045252 A1 | 3/2007 | Kleine et al. |
| 2007/0048350 A1 | 3/2007 | Faltico et al. |
| 2007/0050007 A1 | 3/2007 | Kondyurin et al. |
| 2007/0050009 A1 | 3/2007 | Flanagan |
| 2007/0052497 A1 | 3/2007 | Tada |
| 2007/0055349 A1 | 3/2007 | Santos et al. |
| 2007/0055354 A1 | 3/2007 | Santos et al. |
| 2007/0055364 A1 | 3/2007 | Hossainy et al. |
| 2007/0059435 A1 | 3/2007 | Santos et al. |
| 2007/0065418 A1 | 3/2007 | Vallana et al. |
| 2007/0073385 A1 | 3/2007 | Schaeffer et al. |
| 2007/0073390 A1 | 3/2007 | Lee |
| 2007/0077163 A1 | 4/2007 | Furst et al. |
| 2007/0100385 A1 | 5/2007 | Rawat et al. |
| 2007/0104753 A1 | 5/2007 | Flanagan |
| 2007/0106347 A1 | 5/2007 | Lin |
| 2007/0106363 A1 | 5/2007 | Weber |
| 2007/0123131 A1 | 5/2007 | Nguyen et al. |
| 2007/0123973 A1 | 5/2007 | Roth et al. |
| 2007/0125247 A1 | 6/2007 | Kunstmann et al. |
| 2007/0129789 A1 | 6/2007 | Cottone, Jr. et al. |
| 2007/0129792 A1 | 6/2007 | Picart et al. |
| 2007/0134288 A1 | 6/2007 | Parsonage et al. |
| 2007/0135908 A1 | 6/2007 | Zhao |
| 2007/0141106 A1 | 6/2007 | Bonutti et al. |
| 2007/0142897 A1 | 6/2007 | Consigny et al. |
| 2007/0142899 A1 | 6/2007 | Lootz et al. |
| 2007/0148251 A1 | 6/2007 | Hossainy et al. |
| 2007/0151093 A1 | 7/2007 | Curcio et al. |
| 2007/0156231 A1 | 7/2007 | Weber |
| 2007/0156248 A1 | 7/2007 | Marco et al. |
| 2007/0160641 A1 | 7/2007 | Jang |
| 2007/0168016 A1 | 7/2007 | Gronemeyer et al. |
| 2007/0173923 A1 | 7/2007 | Savage et al. |
| 2007/0178129 A1 | 8/2007 | Flanagan |
| 2007/0181433 A1 | 8/2007 | Birdsall et al. |
| 2007/0184083 A1 | 8/2007 | Coughlin |
| 2007/0190104 A1 | 8/2007 | Kamath et al. |
| 2007/0191923 A1 | 8/2007 | Weber |
| 2007/0191928 A1 | 8/2007 | Rolando et al. |
| 2007/0191931 A1 | 8/2007 | Weber |
| 2007/0191943 A1 | 8/2007 | Shrivastava et al. |
| 2007/0197980 A1 | 8/2007 | Barry et al. |
| 2007/0202466 A1 | 8/2007 | Schwarz et al. |
| 2007/0207186 A1 | 9/2007 | Scanlon et al. |
| 2007/0208412 A1 | 9/2007 | Elmaleh |
| 2007/0212388 A1 | 9/2007 | Patravale et al. |
| 2007/0219626 A1 | 9/2007 | Rolando et al. |
| 2007/0224116 A1 | 9/2007 | Chandrasekaran et al. |
| 2007/0224244 A1 | 9/2007 | Weber et al. |
| 2007/0225799 A1 | 9/2007 | Doty |
| 2007/0244541 A1 | 10/2007 | Schulman |
| 2007/0244569 A1 | 10/2007 | Weber et al. |
| 2007/0250155 A1 | 10/2007 | Simpson |
| 2007/0250156 A1 | 10/2007 | Palmaz |
| 2007/0250158 A1 | 10/2007 | Krivoruchko et al. |
| 2007/0255388 A1 | 11/2007 | Rudakov et al. |
| 2007/0255392 A1 | 11/2007 | Johnson |
| 2007/0264199 A1 | 11/2007 | Labhasetwar et al. |
| 2007/0264303 A1 | 11/2007 | Atanasoska et al. |
| 2007/0270940 A1 | 11/2007 | Doty |
| 2007/0270942 A1 | 11/2007 | Thomas |
| 2007/0281073 A1 | 12/2007 | Gale et al. |
| 2007/0281117 A1 | 12/2007 | Kaplan et al. |
| 2007/0282247 A1 | 12/2007 | Desai et al. |
| 2007/0282426 A1 | 12/2007 | Wang et al. |

(56) References Cited

U.S. PATENT DOCUMENTS

| | | |
|---|---|---|
| 2007/0282432 A1 | 12/2007 | Stinson et al. |
| 2007/0299509 A1 | 12/2007 | Ding |
| 2007/0299512 A1 | 12/2007 | Korzuschnik et al. |
| 2008/0003251 A1 | 1/2008 | Zhou |
| 2008/0003256 A1 | 1/2008 | Martens et al. |
| 2008/0003431 A1 | 1/2008 | Fellinger et al. |
| 2008/0004691 A1 | 1/2008 | Weber et al. |
| 2008/0031765 A1 | 2/2008 | Gerold et al. |
| 2008/0033522 A1 | 2/2008 | Grewe et al. |
| 2008/0033530 A1 | 2/2008 | Zberg et al. |
| 2008/0033531 A1 | 2/2008 | Barthel et al. |
| 2008/0033533 A1 | 2/2008 | Borck |
| 2008/0033536 A1 | 2/2008 | Wittchow |
| 2008/0033537 A1 | 2/2008 | Tittelbach |
| 2008/0033538 A1 | 2/2008 | Borck et al. |
| 2008/0033539 A1 | 2/2008 | Sternberg et al. |
| 2008/0033576 A1 | 2/2008 | Gerold et al. |
| 2008/0038146 A1 | 2/2008 | Wachter et al. |
| 2008/0050413 A1 | 2/2008 | Horvers et al. |
| 2008/0051335 A1 | 2/2008 | Kleiner et al. |
| 2008/0051866 A1 | 2/2008 | Chen et al. |
| 2008/0051872 A1 | 2/2008 | Borck |
| 2008/0051881 A1 | 2/2008 | Feng et al. |
| 2008/0057105 A1 | 3/2008 | Atanasoska et al. |
| 2008/0058919 A1 | 3/2008 | Kramer-Brown et al. |
| 2008/0058921 A1 | 3/2008 | Lindquist |
| 2008/0058923 A1 | 3/2008 | Bertsch et al. |
| 2008/0069854 A1 | 3/2008 | Xiao et al. |
| 2008/0069858 A1 | 3/2008 | Weber |
| 2008/0071348 A1 | 3/2008 | Boismier et al. |
| 2008/0071349 A1 | 3/2008 | Atanasoska et al. |
| 2008/0071350 A1 | 3/2008 | Stinson |
| 2008/0071351 A1 | 3/2008 | Flanagan et al. |
| 2008/0071352 A1 | 3/2008 | Weber et al. |
| 2008/0071353 A1 | 3/2008 | Weber et al. |
| 2008/0071355 A1 | 3/2008 | Weber et al. |
| 2008/0071357 A1 | 3/2008 | Girton et al. |
| 2008/0071358 A1 | 3/2008 | Weber et al. |
| 2008/0082162 A1 | 4/2008 | Boismier et al. |
| 2008/0086199 A1 | 4/2008 | Dave et al. |
| 2008/0086201 A1 | 4/2008 | Weber et al. |
| 2008/0090097 A1 | 4/2008 | Shaw et al. |
| 2008/0097577 A1 | 4/2008 | Atanasoska et al. |
| 2008/0103589 A1 | 5/2008 | Cheng et al. |
| 2008/0103594 A1 | 5/2008 | Loffler et al. |
| 2008/0107890 A1 | 5/2008 | Bureau et al. |
| 2008/0109072 A1 | 5/2008 | Girton |
| 2008/0113083 A1 | 5/2008 | Sutermeister et al. |
| 2008/0124373 A1 | 5/2008 | Xiao et al. |
| 2008/0131479 A1 | 6/2008 | Weber et al. |
| 2008/0140172 A1 | 6/2008 | Carpenter et al. |
| 2008/0140186 A1 | 6/2008 | Grignani et al. |
| 2008/0145400 A1 | 6/2008 | Weber et al. |
| 2008/0147175 A1 | 6/2008 | Krivoruchko et al. |
| 2008/0147177 A1 | 6/2008 | Scheuermann et al. |
| 2008/0148002 A1 | 6/2008 | Fleming |
| 2008/0152929 A1 | 6/2008 | Zhao |
| 2008/0160166 A1 | 7/2008 | Rypacek et al. |
| 2008/0160259 A1 | 7/2008 | Nielson et al. |
| 2008/0161906 A1 | 7/2008 | Atanasoska et al. |
| 2008/0171929 A1 | 7/2008 | Katims |
| 2008/0175885 A1 | 7/2008 | Asgari |
| 2008/0177378 A1 | 7/2008 | Asgari |
| 2008/0183269 A2 | 7/2008 | Kaplan et al. |
| 2008/0183277 A1 | 7/2008 | Atanasoska et al. |
| 2008/0183278 A1 | 7/2008 | Atanasoska et al. |
| 2008/0188927 A1 | 8/2008 | Rohde et al. |
| 2008/0195170 A1 | 8/2008 | Asgari |
| 2008/0195189 A1 | 8/2008 | Asgari |
| 2008/0195198 A1 | 8/2008 | Asgari |
| 2008/0208308 A1 | 8/2008 | Allen et al. |
| 2008/0208313 A1 | 8/2008 | Yu et al. |
| 2008/0208352 A1 | 8/2008 | Krivoruchko et al. |
| 2008/0213377 A1 | 9/2008 | Bhatia et al. |
| 2008/0215129 A1 | 9/2008 | Venturelli et al. |
| 2008/0215139 A1 | 9/2008 | McMorrow et al. |
| 2008/0215140 A1 | 9/2008 | Borck et al. |
| 2008/0241218 A1 | 10/2008 | McMorrow et al. |
| 2008/0243113 A1 | 10/2008 | Shastri et al. |
| 2008/0243230 A1 | 10/2008 | Lootz et al. |
| 2008/0243231 A1 | 10/2008 | Flanagan et al. |
| 2008/0243234 A1 | 10/2008 | Wilcox |
| 2008/0243240 A1 | 10/2008 | Doty et al. |
| 2008/0243242 A1 | 10/2008 | Kappelt et al. |
| 2008/0249600 A1 | 10/2008 | Atanasoska et al. |
| 2008/0249615 A1 | 10/2008 | Weber |
| 2008/0255508 A1 | 10/2008 | Wang |
| 2008/0255509 A1 | 10/2008 | Wang |
| 2008/0262589 A1 | 10/2008 | Nagura |
| 2008/0268308 A1 | 10/2008 | Schilling et al. |
| 2008/0269872 A1 | 10/2008 | Lootz et al. |
| 2008/0288048 A1 | 11/2008 | Rolando et al. |
| 2008/0290467 A1 | 11/2008 | Shue |
| 2008/0294236 A1 | 11/2008 | Anand et al. |
| 2008/0294246 A1 | 11/2008 | Scheuermann |
| 2008/0306584 A1 | 12/2008 | Kramer-Brown |
| 2009/0005862 A1 | 1/2009 | Nakatani et al. |
| 2009/0012599 A1 | 1/2009 | Broome et al. |
| 2009/0018639 A1 | 1/2009 | Kuehling |
| 2009/0018647 A1 | 1/2009 | Benco et al. |
| 2009/0018648 A1 | 1/2009 | Wittchow |
| 2009/0022771 A1 | 1/2009 | Lynn et al. |
| 2009/0024199 A1 | 1/2009 | Birdsall et al. |
| 2009/0024209 A1 | 1/2009 | Ozdil et al. |
| 2009/0024210 A1 | 1/2009 | Klocke et al. |
| 2009/0024211 A1 | 1/2009 | Wittchow |
| 2009/0028785 A1 | 1/2009 | Clarke |
| 2009/0030494 A1 | 1/2009 | Stefanadis et al. |
| 2009/0030500 A1 | 1/2009 | Weber et al. |
| 2009/0030504 A1 | 1/2009 | Weber et al. |
| 2009/0030506 A1 | 1/2009 | Klocke et al. |
| 2009/0030507 A1 | 1/2009 | Klocke et al. |
| 2009/0035351 A1 | 2/2009 | Berglund et al. |
| 2009/0043330 A1 | 2/2009 | To |
| 2009/0043374 A1 | 2/2009 | Nakano |
| 2009/0043380 A1 | 2/2009 | Blaha et al. |
| 2009/0048660 A1 | 2/2009 | Adden |
| 2009/0062905 A1 | 3/2009 | Moore, Jr. et al. |
| 2009/0069884 A1 | 3/2009 | Mueller |
| 2009/0076588 A1 | 3/2009 | Weber |
| 2009/0076596 A1 | 3/2009 | Adden et al. |
| 2009/0081293 A1 | 3/2009 | Murase et al. |
| 2009/0081450 A1 | 3/2009 | Ascher et al. |
| 2009/0088831 A1 | 4/2009 | Goto |
| 2009/0088834 A1 | 4/2009 | Wang |
| 2009/0093871 A1 | 4/2009 | Rea et al. |
| 2009/0095715 A1 | 4/2009 | Sabaria |
| 2009/0118809 A1 | 5/2009 | Scheuermann et al. |
| 2009/0118812 A1 | 5/2009 | Kokate et al. |
| 2009/0118813 A1 | 5/2009 | Scheuermann et al. |
| 2009/0118814 A1 | 5/2009 | Schoenle et al. |
| 2009/0118815 A1 | 5/2009 | Arcand et al. |
| 2009/0118818 A1 | 5/2009 | Foss et al. |
| 2009/0118819 A1 | 5/2009 | Merz et al. |
| 2009/0118820 A1 | 5/2009 | Gregorich et al. |
| 2009/0118821 A1 | 5/2009 | Scheuermann et al. |
| 2009/0118822 A1 | 5/2009 | Holman et al. |
| 2009/0118823 A1 | 5/2009 | Atanasoska et al. |
| 2009/0123517 A1 | 5/2009 | Flanagan et al. |
| 2009/0123521 A1 | 5/2009 | Weber et al. |
| 2009/0124956 A1 | 5/2009 | Swetlin et al. |
| 2009/0131540 A1 | 5/2009 | Hiromoto et al. |
| 2009/0143855 A1 | 6/2009 | Weber et al. |
| 2009/0149942 A1 | 6/2009 | Edelman et al. |
| 2009/0157165 A1 | 6/2009 | Miller et al. |
| 2009/0157172 A1 | 6/2009 | Kokate et al. |
| 2009/0164002 A1 | 6/2009 | Becher et al. |
| 2009/0171452 A1 | 7/2009 | Yamamoto et al. |
| 2009/0177273 A1 | 7/2009 | Piveteau et al. |
| 2009/0182290 A1 | 7/2009 | Harder et al. |
| 2009/0182337 A1 | 7/2009 | Stopek et al. |
| 2009/0182425 A1 | 7/2009 | Duda et al. |
| 2009/0192571 A1 | 7/2009 | Stett et al. |
| 2009/0192594 A1 | 7/2009 | Borck |

(56) References Cited

U.S. PATENT DOCUMENTS

| | | |
|---|---|---|
| 2009/0192595 A1 | 7/2009 | Nagura et al. |
| 2009/0192596 A1 | 7/2009 | Adden |
| 2009/0196899 A1 | 8/2009 | Birdsall et al. |
| 2009/0198320 A1 | 8/2009 | Mueller et al. |
| 2009/0202610 A1 | 8/2009 | Wilson |
| 2009/0204203 A1 | 8/2009 | Allen et al. |
| 2009/0208428 A1 | 8/2009 | Hill et al. |
| 2009/0208555 A1 | 8/2009 | Kuttler et al. |
| 2009/0214373 A1 | 8/2009 | Stinson et al. |
| 2009/0220612 A1 | 9/2009 | Perera |
| 2009/0228037 A1 | 9/2009 | Rego |
| 2009/0240323 A1 | 9/2009 | Wilcox |
| 2009/0254171 A1 | 10/2009 | Heikkila |
| 2009/0259300 A1 | 10/2009 | Dorogy, Jr. et al. |
| 2009/0264979 A1 | 10/2009 | Kao et al. |
| 2009/0270979 A1 | 10/2009 | Adden |
| 2009/0274737 A1 | 11/2009 | Borck |
| 2009/0281613 A1 | 11/2009 | Atanasoska et al. |
| 2009/0287301 A1 | 11/2009 | Weber |
| 2009/0287302 A1 | 11/2009 | Thomas et al. |
| 2009/0306584 A1 | 12/2009 | Schmidtlein et al. |
| 2009/0306756 A1 | 12/2009 | Cho et al. |
| 2009/0306765 A1 | 12/2009 | Weber |
| 2009/0306766 A1 | 12/2009 | McDermott et al. |
| 2009/0311300 A1 | 12/2009 | Wittchow |
| 2009/0312807 A1 | 12/2009 | Boudreault et al. |
| 2009/0319035 A1 | 12/2009 | Terry |
| 2009/0324684 A1 | 12/2009 | Atanasoska et al. |
| 2009/0326638 A1 | 12/2009 | Atanasoska et al. |
| 2010/0008970 A1 | 1/2010 | O'Brien et al. |
| 2010/0010621 A1 | 1/2010 | Klocke |
| 2010/0010640 A1 | 1/2010 | Gerold et al. |
| 2010/0015206 A1 | 1/2010 | Flanagan et al. |
| 2010/0016940 A1 | 1/2010 | Shokoohi et al. |
| 2010/0021523 A1 | 1/2010 | Scheuermann et al. |
| 2010/0023112 A1 | 1/2010 | Borck et al. |
| 2010/0023116 A1 | 1/2010 | Borck et al. |
| 2010/0028436 A1 | 2/2010 | Ohrlander et al. |
| 2010/0030326 A1 | 2/2010 | Radhakrishnan et al. |
| 2010/0034899 A1 | 2/2010 | Harder et al. |
| 2010/0042205 A1 | 2/2010 | Atanasoska et al. |
| 2010/0042206 A1 | 2/2010 | Yadav et al. |
| 2010/0047312 A1 | 2/2010 | Wittchow |
| 2010/0047324 A1 | 2/2010 | Fritz et al. |
| 2010/0049146 A1 | 2/2010 | Nielsen et al. |
| 2010/0049296 A1 | 2/2010 | Sarasam et al. |
| 2010/0049299 A1 | 2/2010 | Popowski et al. |
| 2010/0049300 A1 | 2/2010 | Harder |
| 2010/0055151 A1 | 3/2010 | Flanagan |
| 2010/0057188 A1 | 3/2010 | Weber |
| 2010/0057197 A1 | 3/2010 | Weber et al. |
| 2010/0070024 A1 | 3/2010 | Venturelli et al. |
| 2010/0075162 A1 | 3/2010 | Yang et al. |
| 2010/0076544 A1 | 3/2010 | Hoffmann et al. |
| 2010/0076556 A1 | 3/2010 | Tomantschger et al. |
| 2010/0081735 A1 | 4/2010 | Mao et al. |
| 2010/0082092 A1 | 4/2010 | Gerold |
| 2010/0087910 A1 | 4/2010 | Weber |
| 2010/0087911 A1 | 4/2010 | Mueller |
| 2010/0087914 A1 | 4/2010 | Bayer et al. |
| 2010/0087915 A1 | 4/2010 | Bayer et al. |
| 2010/0087916 A1 | 4/2010 | Bayer et al. |
| 2010/0092535 A1 | 4/2010 | Cook et al. |
| 2010/0106243 A1 | 4/2010 | Wittchow |
| 2010/0119576 A1 | 5/2010 | Harder et al. |
| 2010/0119581 A1 | 5/2010 | Gratz et al. |
| 2010/0121432 A1 | 5/2010 | Klocke et al. |
| 2010/0125325 A1 | 5/2010 | Allen et al. |
| 2010/0125328 A1 | 5/2010 | Flanagan |
| 2010/0131050 A1 | 5/2010 | Zhao |
| 2010/0131052 A1 | 5/2010 | Kappelt et al. |
| 2010/0161031 A1 | 6/2010 | Papirov et al. |
| 2010/0217370 A1 | 8/2010 | Scheuermann et al. |
| 2011/0313510 A1 | 12/2011 | Gale et al. |
| 2012/0080189 A1 | 4/2012 | Marya et al. |

FOREIGN PATENT DOCUMENTS

| | | |
|---|---|---|
| CA | 2 235 031 | 10/1998 |
| CA | 2 346 857 | 5/2000 |
| CA | 2 371 800 | 8/2000 |
| DE | 198 11 033 | 8/1999 |
| DE | 198 56 983 | 12/1999 |
| DE | 103 57 281 | 7/2005 |
| DE | 103 61 941 | 7/2005 |
| DE | 10 2006 38236 | 2/2008 |
| EP | 0 006 544 | 6/1979 |
| EP | 0 337 035 | 10/1989 |
| EP | 0 337 035 | 11/1993 |
| EP | 0 615 769 | 9/1994 |
| EP | 0 923 389 | 7/1998 |
| EP | 0 923 912 | 6/1999 |
| EP | 0 966 979 | 12/1999 |
| EP | 0 972 563 | 1/2000 |
| EP | 1 054 644 | 11/2000 |
| EP | 1 071 490 | 1/2001 |
| EP | 1 222 901 | 7/2002 |
| EP | 1 260 214 | 11/2002 |
| EP | 1 270 023 | 1/2003 |
| EP | 1 273 314 | 1/2003 |
| EP | 1 370 306 | 12/2003 |
| EP | 0 923 912 | 2/2004 |
| EP | 1 389 471 | 2/2004 |
| EP | 1 393 766 | 3/2004 |
| EP | 1 419 793 | 5/2004 |
| EP | 0 951 877 | 6/2004 |
| EP | 1 260 214 | 6/2004 |
| EP | 0 875 218 | 2/2005 |
| EP | 1 389 471 | 8/2006 |
| EP | 1 733 746 | 12/2006 |
| EP | 1 752 167 | 2/2007 |
| EP | 1 465 552 | 5/2007 |
| EP | 1 835 042 | 9/2007 |
| EP | 1 750 780 | 10/2007 |
| EP | 1 562 565 | 3/2008 |
| EP | 1 642 551 | 12/2008 |
| EP | 1 653 885 | 4/2009 |
| EP | 1 632 256 | 9/2009 |
| EP | 1 703 858 | 10/2009 |
| EP | 2 139 535 | 1/2010 |
| EP | 1 883 380 | 3/2010 |
| EP | 2 189 169 | 5/2010 |
| JP | 06-306298 | 11/1992 |
| JP | 06-292716 | 10/1994 |
| JP | 10295824 | 11/1998 |
| JP | 2001511049 | 8/2001 |
| JP | 2003503157 | 1/2003 |
| JP | 2003-052834 | 2/2003 |
| JP | 2003-169846 | 6/2003 |
| JP | 2003-250880 | 9/2003 |
| JP | 2003-526386 | 9/2003 |
| JP | 2003275228 | 9/2003 |
| JP | 2004-121827 | 4/2004 |
| JP | 2005168937 | 6/2005 |
| JP | 2007307132 | 11/2007 |
| RU | 2 218 242 | 12/2003 |
| WO | WO 93/04118 | 3/1993 |
| WO | WO 97/11724 | 4/1997 |
| WO | WO 98/48851 | 11/1998 |
| WO | WO9902195 | 1/1999 |
| WO | WO 99/47077 | 9/1999 |
| WO | 99/64580 | 12/1999 |
| WO | WO 99/64580 | 12/1999 |
| WO | WO 00/25841 | 5/2000 |
| WO | WO 00/48660 | 8/2000 |
| WO | WO 00/51136 | 8/2000 |
| WO | WO 00/66190 | 11/2000 |
| WO | WO0101957 | 1/2001 |
| WO | 01/32072 | 5/2001 |
| WO | WO 01/49338 | 7/2001 |
| WO | WO 01/78906 | 10/2001 |
| WO | 02/39875 | 5/2002 |
| WO | WO 02/45764 | 6/2002 |
| WO | WO 02/47739 | 6/2002 |
| WO | WO 02/053202 | 7/2002 |

(56) References Cited

FOREIGN PATENT DOCUMENTS

| WO | 02/076523 | 10/2002 |
|---|---|---|
| WO | 03/002243 | 1/2003 |
| WO | WO 03/013396 | 2/2003 |
| WO | 03/035123 | 5/2003 |
| WO | WO 03/035131 | 5/2003 |
| WO | WO 03/035278 | 5/2003 |
| WO | 03/046062 | 6/2003 |
| WO | 03/068285 | 8/2003 |
| WO | WO 03/063733 | 8/2003 |
| WO | WO 03/094990 | 11/2003 |
| WO | 2004/025332 | 3/2004 |
| WO | 2004/026361 | 4/2004 |
| WO | WO 2004/093643 | 11/2004 |
| WO | WO2004110515 | 12/2004 |
| WO | WO2005042045 | 5/2005 |
| WO | WO 2005/065576 | 7/2005 |
| WO | WO2005065576 | 7/2005 |
| WO | 2005/079335 | 9/2005 |
| WO | WO2005084582 | 9/2005 |
| WO | WO 2005/110395 | 11/2005 |
| WO | WO 2005/118019 | 12/2005 |
| WO | WO2005117752 | 12/2005 |
| WO | WO 2006/008739 | 1/2006 |
| WO | WO 2006/060033 | 6/2006 |
| WO | WO 2006/060534 | 6/2006 |
| WO | WO 2006/065356 | 6/2006 |
| WO | 2006/077154 | 7/2006 |
| WO | WO 2006/108065 | 10/2006 |
| WO | WO 2007/005806 | 1/2007 |
| WO | 2007/013102 | 2/2007 |
| WO | WO 2007/018931 | 2/2007 |
| WO | 2007/035791 | 3/2007 |
| WO | WO 2007/024552 | 3/2007 |
| WO | 2007/079636 | 7/2007 |
| WO | WO 2007/082147 | 9/2007 |
| WO | 2008/036457 | 3/2008 |
| WO | 2008/036548 | 3/2008 |
| WO | 2008/036549 | 3/2008 |
| WO | 2008/036554 | 3/2008 |
| WO | WO 2008/062414 | 5/2008 |
| WO | WO 2008/117315 | 10/2008 |
| WO | 2009/045773 | 4/2009 |

OTHER PUBLICATIONS

Ivanova and Ivanov, "Mechanisms of the extracellular antioxidant defend," *Experimental Pathology and Parasitology*, 2000, 4:49-59.

Jiang, "A review of wet impregnation—An alternative method for the fabrication of high performance and nano-structured electrodes of solid oxide fuel cells," *Materials Science and Engineering A*, 2006, 418:199-210.

Lambert et al., "Inhibition of carcinogenesis by polyphenols: evidence from laboratory investigations," *Am. J. Clin. Nutr.*, 2005, 81:284S-291S.

Liao et al., "Fabrication of porous biodegradable polymer scaffolds using a solvent merging/particulate leaching method," *J. Biomed. Mater. Res.*, 2002, 59(4):676-681.

Mikos and Temenoff, "Formation of highly porous biodegradable scaffolds for tissue engineering," *Electronic Journal of Biotechnology*, 2000, 3(2):1-6.

Moskaug et al., "Polyphenols and glutathione synthesis regulation," *Am. J. Clin. Nutr.*, 2005, 81:277S-283S.

Park, "Microstructural change and precipitation hardening in melt-spun Mg-X-Ca alloys," *Science and Technology of Advanced Materials*, 2001, 2:73-78.

Wallerath et al., "A blend of polyphenols explains the stimulatory effect of red wine on human endothelial NO synthase," *Nitric Oxide*, 2005, 12(2):97-104.

Widmer et al., "Manufacture of porous biodegradable polymer conduits by an extrusion process for guided tissue regeneration," *Biomaterials*, 1998, 19:1945-1955.

Williamson et al., "Bioavailability and bioefficacy of polyphenols in humans. II. Review of 93 intervention studies," *Am. J. Clin. Nutr.*, 2005, 81:243S-255S.

U.S. Appl. No. 10/849,742, filed May 20, 2004, Chen et al.
U.S. Appl. No. 60/826,002, filed Sep. 18, 2006, Girton et al.
U.S. Appl. No. 60/862,318, filed Oct. 20, 2006, Atanasoska et al.
U.S. Appl. No. 60/845,136, filed Sep. 15, 2006, Weber et al.

"Galvanic cell" printout from wikipedia, 2 pgs, printed Oct. 28, 2005.

"Galvanic corrosion", http://www.corrosion-doctors.org/Aircraft/galvdefi.htm, 3 pgs., printed Oct. 28, 2005.

"Corrosion Theory and Corrosion Protection," *EM 1110-2-3400*, 1995, 8 pages.

Antipov et al., "Polyelectrolyte Multilayer Capsule Permeability Control," *Colloids and Surfaces A: Physiochem. Eng. Aspects*, 2002, 198-200, 535-541.

Antipov et al., "Polyelectrolyte Multilayer Capsules as Vehicles with Tunable Permeability," *Advances in Colloid and Interface Science*, 2004, 111:49-61.

Artyukhin et al., "Layer-by-Layer Electrostatic Self-Assembly of Polyelectrolyte Nanoshells on Individual Carbon Nanotube Templates," *Langmuir*, 2004, 20:1442-1448.

Bolz et al., "Effect of smooth, porous and fractal surface structure on the properties of an interface," *J. Materials Science: Materials in Medicine*, 1995, 6:844-848.

Changwen et al., "Polyoxometalate-based organic-inorganic hybrid materials"; http://www.solgel.com/articles/oct01/changwen.asp, Retrieved from the Internet on Nov. 1, 2004 (17 pages).

Authorized Officer Simin Baharlou, International Search Report/Written Opinion in PCT/US07/66568 mailed Oct. 8, 2007, 11 pages.

Authorized Officer Athina Nickitas-Etienne, International Search Report/Written Opinion in PCT/US07/78449, mailed Jan. 13, 2009, 24 pages.

Authorized Officer Simin Baharlou, International Search Report/Written Opinion in PCT/US07/75072 mailed Jan. 25, 2008, 21 pages.

International Search Report/Written Opinion in PCT/US07/78429 mailed Mar. 28, 2008, 13 pages.

International Preliminary Report on Patentability in PCT/US07/78429 mailed Apr. 2, 2009, 8 pages.

Authorized Officer Joëlle Gerber, International Search Report/Written Opinion in PCT/US07/78450 mailed Nov. 19, 2008, 17 pages.

International Search Report/Written Opinion in PCT/US07/73839 mailed Apr. 16, 2008, 17 pages.

International Preliminary Report on Patentability in PCT/US07/73839 mailed 2 Apr. 2, 2009, 10 pages.

Authorized Officer Cecilia Giel-Barragán Ramos, International Search Report/Written Opinion in PCT/US07/79841 mailed Feb. 4, 2009, 21 pages.

Di Mario et al., "MOONLIGHT: a controlled registry of an iridium-oxide coated stent with angiographic follow up," *Int. J. Cardiol.*, 2004, 95:329-331.

Eniola and Hammer, "Characterization of biodegradable drug delivery vehicles with the adhesive properties of leukocytes II: effect of degradation on targeting activity," *Biomaterials*, 2005, 26:661-670.

Fischer et al., "Hydrogen in magnesium alloys and magnesium interfaces: preparation, electronic properties and interdiffusion," *J. Less Common Metals*, 1991, 172:808-815.

Hau et al., "Surface-Chemistry Technology for Microfluidics," *J. Micromech. Microeng.*, 2003, 13:272-278.

Huang et al., "A Review on Polymer Nanofibers by Electro-spinning and their Applications in Nanocomposites," *Composites Science & Technology*, 2003, 63:2223-2253.

Kean and Davies, "Cathodic Protection," 7 pages, 1981; http://www.npl.co.uk/upload/pdf/cathodic_protection.pdf.

Mamedov et al., "Molecular Design of Strong Single-Wall Carbon Nanotube/Polyelectrolyte Multilayer Composites," *Nature Materials*, 2002, 1:190-194.

Matsuoka et al., "Hyperthermia Using Magnetite Cationic Liposomes for Hamster Osteosarcoma," *BioMagnetic Research and Technology*, 2004, 2:3-8.

Medical Device Daily, "Conor Cites Positive 12-month Results for Its CoStar Stent", May 2005 (1 page).

Middleton and Tipton, "Synthetic Biodegradable Polymers as Medical Devices," http://www.devicelink.com/mpb/archive/98/03/002.html, Mar. 1998, 9 pages.

(56) References Cited

OTHER PUBLICATIONS

Peuster et al., "Long-term biocompatibility of a corrodible peripheral iron stent in the porcine of descending aorta," *Biomaterials*, 2006, 27:4955-4962.
Peuster et al., "A novel approach to temporary stenting: degradable cardiovascular stents produced from corrodible metal-results 6-18 months after implantation into New Zealand white rabbits," *Heart*, 2001, 86(5):563.
Schetky, "Shape Memory Alloys," *Encyclopedia of Chemical Technology* (3rd ed.), 1962, John Wiley & Sons, 20:726.
Shaw, "Corrosion Resistance of Magnesium Alloys," *ASM Handbook vol. 13A: Corrosion: Fundamentals, Testing, and Protection*, 2003, 5 pages.
Suslick et al., "The Photochemistry of Chromium, Manganese, and Iron Porphyrin Complexes," *J. Chem.*, 1992, 16:633-642.
Wan et al., "Influence of Plasma Immersion Ion Implantation on Corrosion Properties of Magnesium," South Jiaotong University, Chengdu, 2005.
Wang et al., "Characterisation of Severely Deformed Austenitic Stainless Steel Wire," *Materials Science and Technology*, 2005, 21:1323-1328.
Weber et al., "Hardness and corrosion resistance of single-phase nitride and carbide on ion," *Materials Science and Engineering*, 1995, 99:205-210.
Weh et al., "Evolution of afractal-like surface structures in layers of polyacrylonitrile solutions by interfacial dynamic processes," *J. Colloid and Interface Science*, 2004, 271:407-415.
Wieneke et al., "Stent Coating: A New Approach in Interventional Cardiology," *Herz*, 2002, 27(6):518-526.
Witte et al., "In vitro and in vivo corrosion measurements of magnesium alloys," *Biomaterials*, 2006, 27:1013-1018.
Yamaguchi et al., "Mg2Si Coating Technology on Magnesium Alloys to Improve Corrosion and Wear Resistance", *JOM*, 2004, p. 343.
Yi et al., "Characterization of a bioactive nanotextured surface created by controlled chemical oxidation of titanium," *Surface Science*, 2006, 600:4613-4621.
You et al., "The Effect of Calcium Additions on the Oxidation Behavior in Magnesium Alloys," *Scripta Mat.*, 2000, 42:1089-1094.
Yu and Uan, "Sacrificial Mg film anode for cathodic protection of die cast Mg-9-wt.%-1 wt.%Zn alloy in NaCl aqueous solution," *Scripta Mat.*, 2006, 54:1253-1257.
Yue et al., "Improvement in the Corrosion Resistance of Magnesium ZK60/SiC Composite by Excimer Laser Surface Treatment," *Scripta Materialia*, 1998, 38(2):191-198.
Zeta Potential—An Introduction in 30 Minutes, Technical Note; http://www.nbtc.cornell.edu/facilities/downloads/Zeta%20potential%20-%20An%20introduction%20in%2030%20minutes.pdf, Retrieved from the Internet on May 9, 2005 (6 pages).
Zhang et al., "Natural Polyelectrolyte Films Based on Layer-by-Layer Deposition of Collagen and Hyaluronic Acid," *Biomaterials*, 2005, 26:3353-3361.
Zhang et al., "Improving multilayer films endurance by photoinduced interaction between Dawson-type polyoxometalate and diazo resin," *Materials Chemistry and Physics*, 2005, 90:57-52.
Zhang et al., "Ways for fabricating stable layer-by layer self-assemblies: combined ionic self-assembly and post chemical reaction," *Colloids and Surfaces A: physiochemical and Engineering Aspects*, 2002, pp. 198-200, 439-442.
Zhou et al., "Drug-loaded, Magnetic, hollow silica nanocomposites for nanomedicine," *Nanomedicine: Nanotechnology, Biology and Medicine*, 2005, 1:233-237.
Zucchi et al., "Influence of a silane treatment on the corrosion resistance of a WE43 magnesium alloy," *Surface Coatings Technol.*, 2006, 200:4136-4143.
"Galvanic cell" printout from Wikipedia, 5 pages, printed on Aug. 16, 2010.
"Galvanice corrosion," http://www.corrosion-doctors.org/aircraft/galvdefi.htm. 3 pgs., printed Oct. 28, 2005.

"Best of the ACC Scientific Session 2002," *Rev. Cardiovasc. Med.*, 2002, 3(2):85-104.
"Galvanic series" printout from Wikipedia, p. 1 of 2, printed Oct. 28, 2005.
Aaltonen, "Atomic Layer Deposition of Noble Metal Thin Films," *University of Helsinki*, Apr. 8, 2005, pp. 1-71.
Aghion et al., "Newly Developed Magnesium Alloys for Powertrain Applications," *JOM*, 2003, p. 30.
Albion Research Notes, Newsletter, Oct. 1994, 3(4): 1-4.
Anand et al., "Ion-exchange resins: carrying drug delivery forward," *DDT*, 2001, 6: 905-914.
Anderson et al., "A new conductive polymer as a replacement for chrome conversion coatings," *2003 Aerospace Coatings Removal and Coatings Conference*, May 20-22, 2003, Colorado Springs, CO, 7 pages.
Arts et al., "Polyphenols and disease risk in epidemiologic studies," *Am. J. Clin. Nutr.*, 2005, 81:317S-325S.
Ashtari et al. "An efficient method for recovery of target ssDNA based on amino-modified silica-coated magnetic nanoparticles" *Talanta 67*. (2005). 548-554.
Atta, "Electrochemical synthesis, characterization and some properties of a polymer derived from thioflavin S.," *European Polymer Journal*, 2005, 41: 3018-3025.
Australian Government, Department of Health and Aging, "Horizon Scanning Technology Prioritising Summary-Biodegradable stents for coronary artery disease," *Australia and New Zealand Horizon Scanning Network (ANZHSN)*, Aug. 2007, pp. 1-13.
Authorized Officer Antoine Laurent, International Preliminary Report on Patentability in PCT/US09/046750 mailed Dec. 23, 2010, 8 pages.
Authorized Officer Antonio Espuch, International Preliminary Report on Patentability in PCT/US09/49422 mailed Jan. 13, 2011, 7 pages.
Authorized Officer Athina Nickitas-Etienne, International Preliminary Report on Patentability in PCT/US07/78449 mailed Mar. 26, 2009, 9 pages.
Authorized Officer Athina Nickitas-Etienne, International Preliminary Report on Patentability in PCT/US07/79841 mailed Apr. 30, 2009, 7 pages.
Authorized officer Athina Nickitas-Etienne, International Preliminary Report on Patentability in PCT/US08/86639 mailed Jun. 24, 2010, 2 pages.
Authorized Officer Aurore Schneider, International Preliminary Report on Patentability from PCT/US2010/042772 mailed Feb. 4, 2011, 9 pages.
Authorized Officer Cecilia Giel-Barragan Ramos, International Search Report/Written in PCT/US07/79841 mailed Feb. 4, 2009, 11 pages.
Authorized Officer Elisabeth Reinecke, International Search Report/Written Opinion in PCT/US07/60137 mailed Jul. 27, 2007, 20 pages.
Authorized Officer Henrique Amaro, International Preliminary Report on Patentability from PCT/US09/043326 mailed Nov. 18, 2010, 7 pages.
Authorized Officer Henrique Amaro, International Preliminary Report on Patentability in PCT/US2009/43326 mailed Nov. 18, 2010, 7 pages.
Authorized Officer Jasmine Messemanne, International Preliminary Report on Patentability from PCT/US09/051965 mailed Feb. 10, 2011, 8 pages.
Authorized Officer Jasmine Messemanne, International Search Report from PCT/US09/051965 mailed Aug. 20, 2010, 13 pages.
Authorized Officer Joelle Gerber, International Search Report/Written Opinion in PCT/US07/78450 mailed Nov. 19, 2008, 17 pages.
Authorized Officer Joëlle Gerber, International Search Report/Written Opinion in PCT/US07/88888 mailed Jul. 13, 2009, 24 pages.
Authorized Officer Mary Celine, International Search Report from PCT/US2010/060412 mailed Feb. 21, 2011, 10 pages.
Authorized Officer Nora Lindner, International Preliminary Report on Patentability in PCT/US07/88888 mailed Jul. 30, 2009, 11 pages.
Authorized Officer Razik Menidjel, International Preliminary Report on Patentability from PCT/US09/059424, mailed May 5, 2011, 8 pages.

(56) References Cited

OTHER PUBLICATIONS

Authorized Officer Simin Baharlou, International Preliminary Report on Patentability in PCT/US07/66568 mailed Oct. 23, 2008, 10 pages.
Authorized Officer Simin Baharlou, International Preliminary Report on Patentability in PCT/US07/75072 mailed Feb. 12, 2009, 9 pages.
Authorized Officer Trudy Hinterwimmer, International Search Report/Written Opinion in PCT/US07/78412 mailed Mar. 3, 2008, 10 pages.
Authorized Officer Trudy Hinterwimmer, International Search Report/Written Opinion in PCT/US09/49422 mailed Aug. 24, 2009, 10 pages.
Authorized Officer Véronique van Loon-Mégard, International Search Report/Written Opinion in PCT/US08/75976 mailed Nov. 25, 2008, 20 pages.
Babapulle and Eisenberg, "Coated stents for their prevention of restenosis: Part II," *Circulation*, 2002, 106:2849-2866.
Bach et al., "Corrosion, Protection and Repassivation After the Deformation of Magnesium Alloys Coated With a Protective Magnesium Fluoride Layer," *JOM*, 2004, p. 343.
Bakkar et al., "Improving corrosion resistance of magnesium-based alloys by surface modification with hydrogen by electrochemical ion reduction (EIR) and by plasma immersion ion implantation (PIII)," *Corrosion Science*, 2005, 47:1211-1225.
Balasubramanian et al. "Dispersion and Stability Studies of Resorcinarene-Encapsulated Gold Nanoparticles." *Langmuir*, 2002, 1676-3681.
Bao, Y. et al. "Preparation of functionalized and gold-coated cobalt nanocrystals for biomedical applications." *Journal of Magnetism and Magnetic Materials*, 2005, 293:15-19.
Baurschmidt et al., "The Electrochemical Aspects of the Thrombogenicity of a Material," *J. Bioengineering*, 1977, 1:261-278.
Bekesi et al., "Efficient submicron processing of metals with femtosecond UV pulses," *Appl. Phys. A.*, Published Oct. 25, 2002, pp. 355-357.
Ben-Hamu et al., "Influence of Si, Ca and Ag addition on corrosion behaviour of new wrought Mg-Zn alloys," *Materials Science and Technology*, 2006, vol. 22, No. 10, pp. 1213-1218.
Bereket et al., "Electrochemical synthesis and anti-corrosive properties of polyaniline, poly(2-anisidine), and poly(aniline-co-2-anisidine) films on stainless steel," *Progress in Organic Coatings*, 2005, 54: 63-72.
Berkland et al., "Controlling Surface Nano-structure Using Flow-Limited Field-Injection Electrostatic Spraying (FFESS) of poly(D,L-lactide-co-glycolide)," *Biomaterials*, 2004, 25:5649-5658.
Bernkop-Schnurch, "Chitosan and its derivatives: potential excipients for peroral peptide delivery systems," *International J. of Pharmaceutics*, 2000, 194: 1-13.
Berry et al., "Functionalisation of magnetic nanoparticles for applications in biomedicine," *J. Phys. D: Appl. Phys.*, 2003, 36:R198-R206.
Biercuk et al., "Low-temperature atomic-layer-deposition lift-off method for microelectronic and nanoelectronic applications," *Applied Physics Letters*, vol. 83, No. 12, Sep. 22, 2003, pp. 2405-2407.
Blanusa et al., "Chelators as Antidotes of Metal Toxicity Therapeutic and Experimental Aspects," *Current Medicinal Chemistry*, 2005, vol. 12, pp. 2771-2794.
Bolz et al., "Effect of smooth, porous and fractal surface structure on the properties of an interface," *J. Materials Science: Materials in Medicine*, 1995, 844-848.
Bosiers et al., "Absorbable Metal stent for CLI in Infrapopliteal lesions: 1 year results," *CX 2005 Global Endovascular Forum*, Apr. 2005, pp. 1-23.
Brandau et al., "Nanoporous Ceramic Coatings for Synthesis of Radioactive Implants," *Journal of Nuclear Medicine Abstract Book*, Jun. 7, 2000, p. 244P, Abstract No. 1076.

Brückner et al., "Metal plasma immersion ion implantation and deposition (MPIIID): chromium on magnesium," *Surface and Coatings Technology*, 1998, 103-104, pp. 227-230.
Brunatto and Muzart, "Influence of the gas mixture flow on the processing parameters of hollow cathode discharge ion sintering," *J. Phys. D.: Appl. Phys.*, 2007, 40: 3937-3944.
Brunner et al., "Porosity Tailored Growth of Black Anodic Layers on Magnesium in an Organic Electrolyte," *Journal of the Electrochemical Society*, vol. 156 (2), Dec. 12, 2008, pp. C62-C66.
Buescher et al., "Characterization of Wet-Chemically Nanostructured Stainless Steel Surfaces," *Mat. Res. Soc. Symp. Proc.*, 2001, 676:1-6.
Caruso et al., "Ultrathin Molybdenum Polyoxometalate-Polyelectrolyte Multilayer Films," *Langmuir*, 1998, 14:3462-3465.
Casan-Pastor et al., "Polyoxometalates: From Inorganic Chemistry to Materials Science," *Frontiers in Bioscience*, 2004, 9:1759-1770.
Chaieb et al , "Inhibition of the corrosion of steel in 1 M HC1 by eugenol derivatives," *Applied Surface Science*, 2005, 246:199-206.
Chang et al., "Effect of Heat Treatment on Corrosion and Electrochemical behavior of Mg-3Nd-0.2Zn-0.4Zr (wt. %) alloy," *Science Direct, Electrochimica Acta 52*, 2007, 3160-3167.
Chang et al., "Templated synthesis of Gold-iron Alloy nanoparticles using pulsed laser deposition," *Nanotechnology*, vol. 17, 2006, pp. 5131-5135.
Changwen et al., "Polyoxometalate-based organic-inorganic hybrid materials," 2004, *Sol-Gel*, p. 1.
Chen et al., "Laser Cladding of Mg20Al8o Powder on ZM5 Magnesium Alloy," *Corrosion Engineering, Science and Technology*, 2007, vol. 42, No. 2, pp. 130-136.
Cheng et al., "Electrogeneration and electrochemical properties of hybrid materials: polypyrrole doped with polyoxometalates $PW_{12-x}Mo_xO_{40}^{3-}$(x=0,3,6,12)," *Synthetic Metals*, 2002, 129: 53-59.
Cho et al., "Gold-coated iron nanoparticles: a novel magnetic resonance agent for $T_1$ and $T_2$ weighted imaging," *Nanotechnology*, vol. 17, 2006, pp. 640-644.
Chou et al., "Electrochemical treatment of mouse and rat fibrosarcomas with direct current," *Bioelectromagnetics*, 1997, 18:14-24.
Clemente-Leon et al., "Hybrid Langmuir-Blodgett Films Formed by Alternating Layers of Magnetic Polyoxometalate Clusters and Organic Donor Molecules—Towards the Preparation of Multifunctional Molecular Materials," *Adv. Mater.*, 2001, 13:574-577.
Cogger et al. "An Introduction to Electrochemical Impedance Measurement," *Solartron Analytical*, 1999, 2-14.
Conolly et al., "X-Ray microtomography studies of localized corrosion and transitions to stress corrosion cracking," *Materials Science and Technology*, 2006, vol. 22, No. 9, pp. 1076-1085.
Costa et al., "The effect of the magnetic field on the corrosion behavior of Nd-Fe-B permanent magnets." *Journal of Magnetism and Magnetic Materials*, 278, 2004, pp. 348-358.
Damen et al., "Paclitaxel esters of malic acid as prodrugs with improved water solubility," *Bioorganic & Medicinal Chemistry*, 2000, 8: 427-432.
Damiani et al., "Vasorelaxant effects on eugenol on rat thoracic aorta," *Vascular Pharmacol.*, 2003, 40:59-66.
Davies, "Changing the salt, changing the drug," *The Pharmaceutical Journal*, 2001, 266: 322-323.
De Geest et al., "Self-rupturing Microcapsules," *Adv. Mater.*, 2005, vol. 17, pp. 2357-2361.
de Witte, "Analysis of the principal component of external casing corrosion in deep well," *J. Appl. Electrochem.*, 1985, 15: 325-334.
Dexter, "Galvanic Corrosion," MAS Note, University of Delaware Sea Grant Marine Advisory Service, 2003.
Di Mario et al., "Drug-eluting bioabsorbable magnesium stent," *J. Interventional Cardiol.*, 2004, 17(6): 391-395
Dowling et al., "Anti-bacterial silver coatings exhibiting enhanced activity through the addition of Platinum," *Surf. & Coatings Tech.*, 2003, 163-164:637-640.
Dumas et al., "Characterization of magnesium fluoride thin films produced by argon ion beam-assisted deposition," *Thin Solid Films*, 2001, pp. 61-68.

(56) References Cited

OTHER PUBLICATIONS

Duncan et al., "Polymer-drug conjugates, PDEPY and PELT: basic principles for design and transfer from the laboratory to clinic," *Journal of Controlled Release*, 2001, 74: 135-146.

Duncan, "The dawning era of polymer therapeutics," *Nature Reviews/Drug Discovery*, 2003, 2: 347-360.

Duygu, "Controlled Release Systems," http://www.biomed.metu.edu.tr/courses/term_papers/contr-rel-sys_duygu.htm (Dec. 30, 2005).

Eggebrecht et al., "Novel Magnetic Resonance-Compatible Coronary Stent: The Absorbable Magnesium-Alloy Stent," *Circulation*, 2005, 112: 303-304.

Eniola et al., "Characterization of Biodegradable Drug Delivery Vehicles with the Adhesive Properties of Leukocytes II: Effect of Degradation on Targeting Activity," *Biomaterials*, 2005, 26:661-670.

Erbel et al., "Absorbierbare Stents-Eine Vielversprechende Neuerung?" *Urban & Vogel*, No. 4, 2007, pp. 308-319.

Erbel et al., "Temporary scaffolding of coronary arteries with bioabsorbable magnesium stents: a prospective, non-randomised multicentre trial," *Lancet*, 2007, vol. 369, pp. 1869-1875.

Erne et al., "The Road to Bioabsorbable Stents: Reaching Clinical Reality?" *Cardio Vascular and Interventional Radiology*, Sep. 26, 2005, pp. 11-16.

European Examiner Marie-France Weiss, International Preliminary report on Patentability received in PCT/US2007/078417, mailed Mar. 26, 2009, 8 pages.

European Examiner Melanie Geuer, International Preliminary Report on Patentability, received in PCT/US2007/078407, mailed Mar. 26, 2009, 6 pages.

European Search Report from EP 10159664.1, mailed Jun. 4, 2010, 3 pages.

International Preliminary Report on Patentability in PCT/US05/16600 mailed Nov. 30, 2006, 7 pages.

International Search Report/Written Opinion in PCT/US05/16600 mailed May 4, 2006, 15 pages.

International Preliminary Report on Patentability in PCT/US07/78476 mailed Mar. 26, 2009, 7 pages.

International Preliminary Report on Patentability in PCT/US07/78411 mailed Feb. 4, 2009, 8 pages.

International Preliminary Report on Patentability in PCT/US07/78412 mailed Apr. 2, 2009, 7 pages.

International Preliminary Report on Patentability in PCT/US07/78505 mailed Mar. 26, 2009, 7 pages.

International Preliminary Report on Patentability in PCT/US07/78450 mailed Mar. 26, 2009, 7 pages.

Falotico, "Cordis Fully Bioabsorbable Stent Program," *Euro PCR09*, May 22, 2009, pp. 1-21.

Fan et al., "Influence of Lanthanum on the microstructure, mechanical property and corrosion resistance of magnesium alloy," *J. Mater Sci*, 2006, vol. 41, pp. 5409-5416.

Farhat et al., "Corrosion Control Using Polyelectrolyte Multilayers," *Electrochemical and Solid State Letters*, 2002, 5(4):B13-B15.

Feng et al., "Sonochemical preparation of photochromic nanocomposite thin film based on polyoxometalates well dispersed in polyacrylamide," *Journal of Solid State Chemistry*, 2002, 169: 1-5.

Feng et al., "Superplasticity and texture of SiC whiskers in a magnesium-based composite," *Scripta Materialia*, 2005, 53: 361-365.

Ferguson et al., "Corrosion—Fatigue Performance of Magnesium Alloys," *International Journal of Modern Physics B*, vol. 17, Nos. 8 & 9, 2003, pp. 1601-1607.

Ferrando, "Review of Corrosion and Corrosion Control of Magnesium Alloys and Composites," *J. Mater. Eng.*, 1989, 11:299-313.

Fischer et al., "Determination of in-vivo corrosion rates of degradable implants by SR-microtomography," date unknown, pp. 1-2.

Fischer et al., "Hydrogen in magnesium alloys and magnesium interfaces: preparation, electronic properties and interdiffusion," *J. Less-Common Metals*, 1991, 172:808-815.

Fontenier et al., "Study of a 'Platinum-Magnesium' Cell to Supply Current to a Pacemaker," *Bioelectrochemistry and Bioenergetics*, 1975, 2(2):106-123.

Franhofer Institut Fertigungstechnik Material forschung, Evaluation of metal injection moulding (MIM) and extrusion as processing technology for biodegradable stents (A 208143), 8 pages.

Franhofer Institut Fertigungstechnik Material forschung, "Phase 2: Evaluation of mictoextrusion," 4 pages.

Fraunhofer EZRT, "Quantitative material analysis by dual energy computed tomography for industrial NDT applications," 2009, 1 pg.

Fraunhofer HS—Poster (German), "Prinzip der hochauflösenden Comptuertomographie," 2009, 1 page.

Frei, "On the Role of Vitamin C and Other Antioxidants in Atherogenesis and Vascular Dysfunction," *Proceedings—Society for Experimental Biology and Medicine*, 1999, 222:196-204.

Gabrielli, Claude. "Use and Applications of Electrochemical Impedance Techniques," *Solartron Analytical*, 1997, 1-102.

Garner et al., "Polypyrrole-heparin composites as stimulus-responsive substrates for endothelial cell growth," *J. Biomed. Mater. Res.*, 1999, 44: 121-129.

Gettleman et al., "Measurement of in vivo corrosion rates in baboons, and correlation with in vitro tests," Journal of Dental Research, 1980, 59: 689-707.

Gettleman et al., "Materials Science: Measurement of in vivo Corrosion Rates in Baboons, and Correlation with in vitro Tests," *Journal of Dental Research*, 1980, vol. 59, pp. 689-707.

Gomes et al., "Alternative tissue engineering scaffolds based on starch: processing methodologies, morphology, degradation and mechanical properties," *Materials Science and Engineering C*, 2002, 20:19-26.

Grassi et al., "Short-term administration of dark chocolate is followed by a significant increase in insulin sensitivity and a decrease in blood pressure in healthy persons," *Am. J. Clin. Nutr.*, 2005,81(3):611-614.

Gray and Luan, "Protective coatings on magnesium and its alloys—a critical review," *J. Alloys Compounds*, 2002, 336:88-113.

Griffiths et al., "Future devices: bioabsorbable stents," *Br. J. Cardiol. (Acute & Interventional Cardiology)*, 2004, 11: AIC80-AIC84.

Grube, "Bioabsorbable Stents-The Boston Scientific & REVA Technology," *EuroPCR 2009*, 2009, pp. 1-27.

Guo et al., "Manipulation of single-wall carbon nanotubes into aligned molecular layers," *Chem. Phys. Lett.*, 2002, 362:314-318.

Guo et al., "Multi-layer LB films of single-wall carbon nanotubes," *Physica B*, 2002, 323:235-236.

Gurib-Fakim, "Medicinal plants: Traditions of yesterday and drugs of tomorrow," *Molecular Aspects of Medicine*, 2006, 27:1-93.

Haferkamp et al., "Magnesium-Base-Alloys as Implant-Material Steps to the Production of Thin Components," *Magnesium*, 2000, 159-164.

Hau et al., "Surface-Chemistry Technology for Microfluidics," *J. Micromech. Microeng.*, 2003.13:272-278.

Heublein et al., "Biocorrosion of magnesium alloys: a new principle in cardiovascular implant technology?" *Heart*, 2003, 89:651-656.

Heublein et al., "Degradation of Metallic Alloys—A New Principle in Stent Technology?" *The American Journal of Cardiology, Eleventh Annual Symposium Transcatheter Cardiovascular Therapeutics Abstracts*, Sep. 22, 1999.

Heublein et al., "Bio-corrosion—a new principle for temporary cardiovascular implants?" *European Heart Journal, Journal of the European Society of Cardiology*, 2000, vol. 21, p. 286, Abstract No. P1605.

Heublein et al., "Local Tissue Engineering by Biocorrosion Vision or Reality?" *The American Journal of Cardiology, TCT Abstracts/Poster*, Oct. 16, 2000.

Huang et al., "A Review on Polymer Nanofibers by Electro-spinning and their Applications in Nanocomposites," 2003, 63:2223-2253.

International Preliminary Report on Patentability in PCT/US07/73839 mailed Apr. 2, 2009.

International Preliminary Report on Patentability in PCT/US07/78429 mailed Apr. 2, 2009.

International Search Report and Written Opinion in PCT/US07/78449, mailed Jan. 13, 2009, 15 pages.

International Search Report and Written Opinion mailed Jan. 25, 2008 in PCT/US07/75072, 14 pages.

International Search Report for PCT/US07/66568 dated Oct. 8, 2007, 15 pages.

(56) References Cited

OTHER PUBLICATIONS

International Search Report from PCT/US 03/20215, mailed Nov. 11, 2003, 4 pages.
International Search Report/Written Opinion in PCT/US07/73839 mailed Apr. 16, 2008, 16 pages.
International Search Report/Written Opinion in PCT/US07/78411 mailed Mar. 6, 2008, 12 pages.
International Search Report/Written Opinion in PCT/US07/78429 mailed Mar. 28, 2008, 14 pages.
International Search Report/Written Opinion in PCT/US07/78505 mailed Mar. 4, 2008, 10 pages.
International Search Report/Written Opinion in PCT/US2009/43326 mailed Aug. 6, 2009, 9 pages.
Jiang, "A review of wet impregnation—An alternative method for the fabrication of high performance and nano-structured electrodes of solid oxide fuel cells," *Materials Science and Engineering A*, 2006, 418:199-210
Kean and Davies, "Cathodic Protection," 7 pages, 1981; http://www.npl.co.uk/upload/pdf/cathodic_protection.
Kim et al., "Comprehensive study on vitamin C equivalent antioxidant capacity (VCEAC) of various polyphenols in scavenging a free radical and its structural relationship," *Crit. Rev. Food Sci. Nutr.*, 2004, 44(4):253-273.
Kim et al., "Effect of Anti-Oxidant (Carvedilol and Probucol) Loaded Stents in a Porcine Coronary Restenosis Model," *Circ. J.*, 2005, 69:101-106.
Kong et al., "Polyelectrolyte-functionalized multiwalled carbon nanotubes: preparation, characterization and layer-by-layer self assembly," *Polymer*, 2005, 46:2472-2485.
Kumar et al., "Polyanhydrides: an overview," *Advanced Drug Delivery Reviews*, 2002, 54:889-910.
Kurth et al., "Multilayer on Solid Planar Substrates: From Structure to Function", *Multi-layer Thin Films Sequential Assembly of Nanocomposite Materials*, 2003, Chapter 14, pp. 393-426.
Kurth et al., "Ultrathin Composite Films Incorporating the Nanoporous Isopolyoxomolybdate 'Keplerate' $(NH_4)_{42}[Mo_{132}O_{372}(CH_3COO)_{30}(H_2O)_{72}]$," *Chem. Mater.*, 2000, 12:2829-2831.
Kutsenko et al., "Structural Changes in Mg Alloy induced by plasma immersion ion implantation of Ag," *Acta Materialia*, 2004, 52:4329-4335.
Lambert et al., "Inhibition of carcinogenesis by polyphenols: evidence from laboratory investigations," *Am. J. Clin. Nutr.*, 2005, 81(suppl):284S-291S.
Lee et al., "Retentive and compressive strengths of modified zinc oxide-eugenol cements," *J. Dentistry*, 2000, 28:69-75.
Li et al., "The corrosion inhibition of the self assembled Au, and Ag nanoparticles films on the surface of copper," *Colloids and Surfaces A: Physiochem. Eng. Aspects*, 2006, 273: 16-23.
Liao et al., "Fabrication of porous biodegradable polymer scaffolds using a solvent merging/particulate leaching method," *J. Biomed. Mater. Res.*, 2002, 59:676-681.
Lin et al., "Micropatterning proteins and cells on polylactic acid and poly(lactide-*co*-glycolide)," *Biomaterials*, 2005, 26:3655-3662.
Liu et al., "Characterizations of polypyrrole (PPy) nano-tubules made by templated ac electropolymerization," *European Polymer Journal*, 2005, 41: 2117-2121.
Liu et al., "Layer-By-Layer Ionic Self-Assembly of Au Colloids Into Multilayer Thin-Films with Bulk Metal Conductivity," *Chemical Physics Letters*, 1998, 298:315-319.
Liu et al., "Functional Polyoxometalate Thin Films via Electrostatic Layer-by-Layer Self-Assembly," *Journal of Cluster Science*, 2003, 14:405-419.
Liu et al., "Sol-gel deposited TiO2 film on NiTi surgical alloy for biocompatibility improvement," *Thin Solid Films*, 2003, 429:225-230.
Liu, *Introduction to Corrosion and Protection*, Corrosion and Protection Centre, School of Materials, The University of Manchester, 2006, 36 pages.
Lu et al., "Theoretical analysis of calcium phosphate precipitation in simulated body fluid," *Biomaterials*, 2005, 26:1097-1108.
Maier et al., "High concentrations of magnesium modulate vascular endothelial cell behaviour in vitro," *Biochim. Biophys. Acta*, 2004, 1689:6-12.
Mansfeld, Florian. "Analysis and Interpretation of EIS Data for Metals and Alloys," *Solartron Analytical*, 1999, 1-77.
Matsuoka et al., "Hyperthermia Using Magnetite Cationic Liposomes for Hamster Osteosarcoma," *Biomagnetic Research and Technology*, Mar. 25, 2004, pp. 1-6.
Medical Device Daily, "Conor Cites Positive 12-month Results for Its CoStar Stent," May 2005 (1 page).
Meng Han, "Laser nitriding of metals: Influences of the ambient pressure and the pulse duration," 2001, Dissertation, Georg-August-Universität Göttingen, 134 pages.
Middleton and Tipton, "Synthetic Biodegradable Polymers as Medical Devices, " http://www.devicelink.com/mpb/archive/98/03/002.html, Mar. 1998, 9 pages.
Mihailovic et al., "Unusual Magnetic State in Lithium-Doped $MoS_2$ Nanotubes," *Phys. Rev. Lett.*, 2003, 90 146401-1-4.
Mikos and Temenoff, "Formation of highly porous biodegradable scaffolds for tissue engineering," *Electronic Journal of Biotechnology*, 2000, 3(2):114-119.
Mohanty et al. "Evaluation of soft tissue response to a poly[urethane urea]," *Biomaterials*, 1992, 13(10):651-656.
Mohanty et al., "Effect of *Curcuma longa* and *Ocimum sanctum* on myocardial apoptosis in experimentally induced myocardial ischemic-reperfusion injury," *BMC Complementary and Alternative Medicine*, 2006, 6:3-14.
Molnar and Garai, "Plant-derived anti-inflammatory compounds affect MIF tautomerase activity," *International Immunopharmacology*, 2005, 5:849-856.
Moskaug et al., "Polyphenols and glutathione synthesis regulation," *Am. J. Clin. Nutr.*, 2005, 81(suppl):277S-283S.
Naderi et al., "Effect of some volatile oils on the affinity of intact and oxidized low-density lipoproteins for adrenal cell surface receptors," *Mol. Cell. Biochem.*, 2004, 267:59-66.
Niemeyer et al., "Magnesium alloys as biodegradable metallic implant materials for cardiovascularic and orthopaedic surgery," *Euromat 2001, 7th European Conference on Advanced Materials and Processes*, Jun. 10-14, 2001 (Abstract).
Niinisto, "Atomic Layer deposition: A key technology for the controlled growth of oxide thin films for advanced applications," *Proc. Estonian Acad. Sci. Phys. Math.*, 2003, 52(3):266-276.
Nilsson et al., "Development of a dosage method for electrochemical treatment of tumours: a simplified mathematical model," *Bioelectrochemistry and Bioenergetics*, 1998, 47:11-18.
Ormiston et al., "Bioabsorbable Coronary Stents," *Circulation Cardiovasc Intervent*, vol. 2, 2009, pp. 255-260.
Ou et al., "Protective effects of eugenol against oxidized LDL-induced cytotoxicity and adhesion molecule expression in endothelial cells," *Food Chem. Toxicol.*, 2006, 44:1485-1495.
Park et al., "Microstructural change and precipitation hardening in melt-spun Mg-X-Ca alloys," *Science and Technology of Advanced Materials*, 2001, 2:73-78.
Peuster et al. "Long-term biocompatibility of a corrodible peripheral iron stent in the porcine of descending aorta," *Biomaterials*, 2006, 4955-4962.
Peuster et al., "A novel approach to temporary stenting: degradable cardiovascular stents produced from corrodible metal-results 6-18 months after implantation into New Zealand white rabbits," *Heart*, 2001, 86(5):563-569.
Peuster et al., "Are resorbable implants about to become a reality," *Cardiol Young*, 2006, 16:107-116.
Pinto Slattow et al., "Optical coherence tomography and intravascular ultrasound imaging of bioabsorbable magnesium stent degradation in porcine coronary arteries," *Cardiovascular Revascularization Medicine 9*, (2008) pp. 248-254.
Prasse et al., "Electric Anisotropy of Carbon Nanofibre/Epoxy Resin Composites Due to Electric Field Induced Alignment," *Composites Science and Technology*, 2003, 63:1835-1841.

(56) References Cited

OTHER PUBLICATIONS

Purushothaman et al. "Reducing Mass-Transport Limitations by Application of Special Pulsed Current Modes" *Journal of the Electrochemical Society*. 152 (4), 2005, J33-J39.
Qasem et al., "Kinetics of paclitaxel 2'-N-methylpyridinium mesylate decomposition," *APPS PharmSciTech*, 2003, 4(2), Article 21, 8 pages.
Quinard et al., "Development of metal/polymer mixtures for micro powder injection moulding," *10th ESAFORM Conference on Material Forming*, 2007, pp. 933-939.
Ratnam et al., "Role of antioxidants in prophylaxis and therapy: A pharmaceutical perspective," *J. Controlled Release*, 2006, 113:189-207.
Remskar et al., "Self-Assembly of Subnanometer-Diameter Single-Wall $MoS_2$ Nanotubes," *Science*, 2001, 292:479-481.
Rezwan et al., "Biodegradable and bio active porous polymer/inorganic composite scaffolds for bone tissue engineering," *Biomaterials*, 2006, 27:3413-3431.
Rhule et al., "Polyoxometalates in Medicine," *Chem. Rev.*, 1998, 98:327-357.
Russell-Stevens et al., "The effect of thermal cycling on the properties of a carbon fibre reinforced magnesium composite," *Materials Science and Engineering A*, 2005, 397: 249-256.
Rutledge et al., "Electrostatic Spinning and Properties of Ultrafine Fibers," *National Textile Center Annual Report*, Nov. 2001, M01-D22, pp. 1-10.
Ryan et al., "Fabrication methods of porous metals for use in orthopaedic applications," *Biomaterials*, 2006, 27:2651-2670.
Sastry et al., "DNA-Mediated Electrostatic Assembly of Gold Nanoparticles into Linear Arrays by a Simple Drop-Coating Procedure," *Appl. Phys. Lett.*, 2001, 78:2943-2945.
Satoh et al., "Effect of Antioxidants on Radical Intensity and Cytotoxic Activity of Eugenol," *Anticancer Res.*, 1998, 18:1549-1552.
Sawitowski et al., "Nanoporous Alumina Coatings for Medical Implants and Stents—Radiotherapy, Drug Delivery, Biological Compatibility," *Materials Research Society Symposium Proceedings*, 1999, 581:523-528.
Sawitowski, "New Drug Delivery Systems—Examples of Applied Nanotechnology," *VDE World Microtechnologies Congress*, Sep. 25-27, 2000, Expo 2000, Hannover, Germany, Proveeds vol. 1, p. 343-346.
Sawyer et al., "Electrochemical Criteria in the Choice of Materials used in Vascular Prostheses," *Biophysical Mechanisms in Vascular Homeostasis and Intravascular Thrombosis*, 1965, pp. 337-348.
Shaw, "Corrosion Resistance of Magnesium Alloys," *ASM Handbook Volume 13A: Corrosion: Fundamentals, Testing, and Protection*. 2003, 5 pages.
Shenoy et al., "Role of Chain Entanglements on Fiber Formation During Electrospinning of Polymer Solutions: Good Solvent, Non-Specific Polymer-polymer Interaction Limit," *Polymer*, 2005, 46:3372-3384.
Shi et al., "A novel electrically conductive and biodegradable composite made of polypyrrole nanoparticles and polylactide," *Biomaterials*, 2004, 25:2477-2488.
Shin, "Experimental Characterization of Electrospinning: the Electrically Forced Jet and Instabilities," *Polymer*, 2001, 42:9955-9967.
Singh et al., "Electrocatalytic Activity of Electrodeposited Composite Films of Polypyrrole and $CoFe_2O_4$ Nanoparticles Towards Oxygen Reduction Reaction," *Electrochimica Acta*, 2004, 49:4605-4612.
Song et al., "Galvanic corrosion of magnesium alloy AZ91D in contact with an aluminium alloy, steel and zinc," *Corrosion Science*, 2004, 46:955-977.
Stoclet et al., "Vascular protection by dietary polyphenols," *Eur. J. Pharmacol.*, 2004, 500:299-313.
Straumal et al., "Vacuum arc deposition of protective layers on glass and polymer," *Thin Solid Films*, 2001, 383:224-226.
Suhaj, "Spice antioxidants isolation and their antiradical activity: a review," *J. Food Composition and Analysis*, 2006, 19:531-537.
Sukhorukov et al., "Comparative Analysis of Hollow and Filled Polyelectrolyte Microcapsules Templated on Melamine Formaldehyde and Carbonate Cores," *Macromol. Chem. Phys.*, 2004, 205:530-535.
Suslick et al., "The photochemistry of chromium, manganese, and iron porphytin complexes," *J. Chem.*, 1992, 16:633-642.
Tada et al., "Distribution of pH during galvanic corrosion of a Zn/steel couple," *Electrochimica Acta*, 2004, 49:1019-1026.
Tan et al., "Systematic Parameter Study for Ultra-Fine Fiber Fabrication Via Electrospinning Process," *Polymer*, 2005, 46:6128-6134.
Tian et al., "Corrosion resistance improvement of magnesium alloy using nitrogen plasma ion implantation," *Surface & Coatings Technology*, 2005, 198:454-458.
Vermette et al., "Immobilized Liposome Layers for Drug Delivery Applications," *J. Controlled Release*, 2002, 80:179-195.
Virtanen, "Corrosion of Biomedical Implant Materials," *Corrosion of Biomedical Implant Materials*, vol. 26, Nos. 2-3, 2008, pp. 147-171.
Viswanathamurthi et al., "Preparation and morphology of niobium oxide fibres by electrospinning," *Chemical Physics Letters*, 2003, 374: 79-84.
von Euler et al., "Cell proliferation and apoptosis in rat mammary cancer after electrochemical treatment (EChT)," *Bioelectrochemistry*, 2004, 62:57-65.
Vrbanic et al., "Air-Stable Monodispersed $Mo_6S_3I_6$ Nanowires," *Nanotechnology*, 2004, 15:635-638.
Waksman et al., "Early-and Long-Term Intravascular Ultrasound and Angiographic Findings After Bioabsorbable Magnesium Stent Implantation in Human Coronary Arteries," *JACC: Cardiovascular Interventions*, vol. 2, No. 4, 2009, pp. 1-9
Wallerath et al., "A blend of polyphenolic compounds explains the stimulatory effect of red wine on human endothelial NO synthase," *Nitric Oxide*, 2005, 12:97-104.
Wan et al., "Preparation and characterization of porous conducting poly(DL-lactide) composite membranes," *Journal of Membrane Science*, 2005, 246: 193-201.
Wan et al., "Influence of Plasma Immersion Ion Implantation on Corrosion Properties of Magnesium," *Southwest Jiaotong University*, 2005, Chengu, 11 pages.
Wang et al., "Nonlinear optical properties of thin iron films grown on MgO (100) by pulsed laser deposition," *Thin Solid Films*, 2005, 471:86-90.
Wang et al., "Characterisation of Severely Deformed Austenitic Stainless Steel Wire," *Materials Science and Technology*, 2005, 21(11):1323-1328.
Wang, "Recent development of non-platinum catalysts for oxygen reduction reaction," *J. Power Sources*, 2005, 152:1-15.
Weber et al., "Hardness and corrosion resistance of single-phase nitride and carbide on iron," *Materials Science and Engineering*, 1995, 99:205-210.
Weh et al., "Evolution of fractal-like surface structures in layers of polyacrylonitrile solutions by interfacial dynamic processes," *J. Colloid and Interface Science*, 2004, 271: 407-415.
Wikipedia, the Free Encyclopedia, "Galvanic Corrosion." <http://en.wikipedia.org/wiki/Galvanic_corrosion> on Mar. 11, 2011, 7 pages.
Witte, "The history of biodegradable magnesium implants: A review," *Acta Biomaterialia*, 2010, 6: 1680-1692
Xu et al., "In vivo corrosion behavior of Mg-Mn-Zn alloy for bone implant application," *Journal of Biomedical Materials Research Part A*, Jun. 4, 2007, pp. 703-711.
Yun et al., "Revolutionizing Biodegradable Materials," *Materials Today*, Oct. 2009, vol. 12, No. 10, pp. 1-11.
Zarras et al., "Progress in using conductive polymers as corrosion-inhibiting coatings," *Radiation Physics and Chemistry*, 2003, 68: 387-394.
Zberg et al., "MgZnCa glasses without clinically observable hydrogen evolution for biodegradable implants," *Nature materials*, Sep. 27, 2009, vol. 8, pp. 887-891.
Zheng, "Symposium on Biodegradable/Biocorroded metallic materials," Nov. 24, 2009, pp. 1-74.
US 6,533,715, 03/2003, Hossainy et al. (withdrawn)

\* cited by examiner

BIOERODIBLE ENDOPROSTHESES AND METHODS OF MAKING THE SAME

CROSS-REFERENCE TO RELATED APPLICATIONS

This application claims priority under 35 USC §119(e) to U.S. Provisional Patent Application Ser. No. 60/844,898, filed on Sep. 15, 2006, the entire contents of which are hereby incorporated by reference.

TECHNICAL FIELD

The invention relates to bioerodible endoprostheses, and to methods of making the same.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced with a medical endoprosthesis. An endoprosthesis is typically a tubular member that is placed in a lumen in the body. Examples of endoprostheses include stents, covered stents, and stent-grafts.

Endoprostheses can be delivered inside the body by a catheter that supports the endoprosthesis in a compacted or reduced-size form as the endoprosthesis is transported to a desired site. Upon reaching the site, the endoprosthesis is expanded, e.g., so that it can contact the walls of the lumen.

The expansion mechanism may include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn from the lumen.

It is sometimes desirable for an implanted endoprosthesis to erode over time within the passageway. For example, a fully erodible endoprosthesis does not remain as a permanent object in the body, which may help the passageway recover to its natural condition. Erodible endoprostheses can be formed from, e.g., a polymeric material, such as polylactic acid, or from a metallic material, such as magnesium, iron or an alloy thereof.

SUMMARY

The invention relates to bioerodible endoprostheses and methods of making the endoprostheses.

In one aspect, the invention features an endoprosthesis including a member. The member includes a bioerodible material and an antioxidant carried by the member.

In another aspect, the invention features a method of making an endoprosthesis. The method includes incorporating a bioerodible material with an antioxidant to form at least a portion of the endoprosthesis.

Embodiments can include one or more of the following features.

The endoprosthesis can include a carrier layer carrying the antioxidant. The antioxidant can be on a surface of the member. The antioxidant can be within a matrix or a carrier material. The carrier can include pores. The carrier can be bioerodible or non-bioerodible. The carrier can be a metal and/or a polymer.

In some embodiments, the antioxidant is encapsulated by the bioerodible material. The bioerodible material can be iron or magnesium. The antioxidant can be in a layer having a thickness of from about 0.5 micrometer to about 10 micrometers. The antioxidant can include a phenol. The antioxidant can include an eugenol, an isoeugenol, and/or an acetyl-eugenol.

The endoprosthesis can further include a drug carried by the member. In some embodiments, the member includes a tubular member constructed to maintain patency of a body vessel. The endoprosthesis can be in the form of a stent.

In some embodiments, the method includes adsorbing the antioxidant on the surface. In some embodiments, the bioerodible material is in the form of a tubular member, and the antioxidant is incorporated on a surface of the tubular member. The bioerodible material can be iron, magnesium, and/or an alloy of iron or magnesium. In some embodiments, the bioerodible material is in the form of a tubular member, and the antioxidant is incorporated in a select portion of the tubular member. In certain embodiments, the antioxidant is in a particle encapsulated by a bioerodible material. The particle can include zinc oxide. In some embodiments, at least a portion of the endoprosthesis can further include a drug. The method can further include incorporating a drug with the portion.

Embodiments may have one or more of the following advantages. Embodiments feature an endoprosthesis, e.g. a coronary stent, that includes a bioerodible portion, such as the body of the stent capable of initially maintaining lumen patency, and an antioxidant. In embodiments, an endoprosthesis is coated with an antioxidant. The antioxidant can reduce (e.g., inhibit) erosion (e.g., corrosion) and can allow for control of biodegradation of metallic endoprosthesis materials. As an example, the antioxidant can allow an endoprosthesis to maintain structural integrity for a longer duration, which can decrease elastic recoil after endoprosthesis expansion. The antioxidant can reduce (e.g., inhibit) lipid peroxidation and can allow for a decrease in restenosis after coronary angioplasty.

The endoprostheses may not need to be removed from a lumen after implantation. The endoprostheses can have a low thrombogenecity and high initial strength. The endoprostheses can exhibit reduced spring back (recoil) after expansion. Lumens implanted with the endoprostheses can exhibit reduced restenosis. The rate of erosion of different portions of the endoprostheses can be controlled, allowing the endoprostheses to erode in a predetermined manner and reducing, e.g., the likelihood of uncontrolled fragmentation. For example, the predetermined manner of erosion can be from an inside of the endoprosthesis to an outside of the endoprosthesis, or from a first end of the endoprosthesis to a second end of the endoprosthesis.

An erodible or bioerodible endoprosthesis, e.g., a stent, refers to an endoprosthesis, or a portion thereof, that exhibits substantial mass or density reduction or chemical transformation, after it is introduced into a patient, e.g., a human patient. Mass reduction can occur by, e.g., dissolution of the material that forms the endoprosthesis and/or fragmenting of the endoprosthesis. Chemical transformation can include oxidation/reduction, hydrolysis, substitution, and/or addition reactions, or other chemical reactions of the material from which the endoprosthesis, or a portion thereof, is made. The erosion can be the result of a chemical and/or biological interaction of the endoprosthesis with the body environment, e.g., the body itself or body fluids, into which it is implanted and/or erosion can be triggered by applying a triggering influence, such as a chemical reactant or energy to the endoprosthesis, e.g., to increase a reaction rate. For example, an endoprosthesis, or a portion thereof, can be formed from an active metal, e.g., Mg or Ca or an alloy thereof, and which can erode by reaction with water, producing the corresponding metal oxide and hydrogen gas (a redox reaction). For example, an endoprosthesis, or a portion thereof, can be formed from an erodible or bioerodible polymer, or an alloy or blend erodible or bioerodible polymers which can erode by hydrolysis with water. The erosion occurs to a desirable extent in a time frame that can provide a therapeutic benefit. For example, in embodiments, the endoprosthesis exhibits substantial mass reduction after a period of time which a function of the endoprosthesis, such as support of the lumen wall or drug delivery is no longer needed or desirable. In particular embodiments, the endoprosthesis exhibits a mass reduction of about 10 percent or more, e.g. about 50 percent or more, after a period of implantation of one day or more, e.g. about 60 days or more, about 180 days or more, about 600 days or more, or 1000 days or less. In embodiments, the endoprosthesis exhibits fragmentation by erosion processes. The fragmentation occurs as, e.g., some regions of the endoprosthesis erode more rapidly than other regions. The faster eroding regions become weakened by more quickly eroding through the body of the endoprosthesis and fragment from the slower eroding regions. The faster eroding and slower eroding regions may be random or predefined. For example, faster eroding regions may be predefined by treating the regions to enhance chemical reactivity of the regions. Alternatively, regions may be treated to reduce erosion rates, e.g., by using coatings. In embodiments, only portions of the endoprosthesis exhibits erodibility. For example, an exterior layer or coating may be erodible, while an interior layer or body is non-erodible. In embodiments, the endoprosthesis is formed from an erodible material dispersed within a non-erodible material such that after erosion, the endoprosthesis has increased porosity by erosion of the erodible material.

Erosion rates can be measured with a test endoprosthesis suspended in a stream of Ringer's solution flowing at a rate of 0.2 mL/second. During testing, all surfaces of the test endoprosthesis can be exposed to the stream. For the purposes of this disclosure, Ringer's solution is a solution of recently boiled distilled water containing 8.6 gram sodium chloride, 0.3 gram potassium chloride, and 0.33 gram calcium chloride per liter.

In some embodiments, an endoprosthesis with an antioxidant layer is relatively easy to make. An antioxidant and a polymer can be dissolved in a solvent and applied to an endoprosthesis. An antioxidant and a polymer can be blended together, and/or can be formed into a composite, and applied to an endoprosthesis. An antioxidant can be applied directly to an endoprosthesis, which can have open or closed pores. An antioxidant can be incorporated with particles and applied to an endoprosthesis.

All publications, patent applications, patents, and other references mentioned herein are incorporated by reference herein in their entirety.

Other aspects, features and advantages will be apparent from the description of the preferred embodiments thereof and from the claims.

DETAILED DESCRIPTION

Figure 1A:
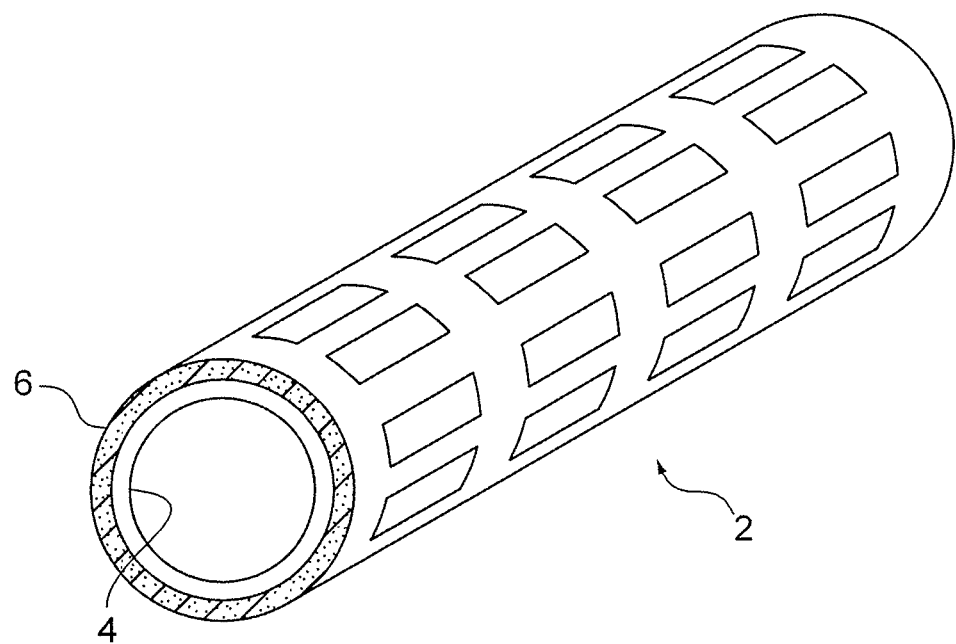
FIG. 1A is a perspective view of an embodiment of an endoprosthesis.
Figure 1B:
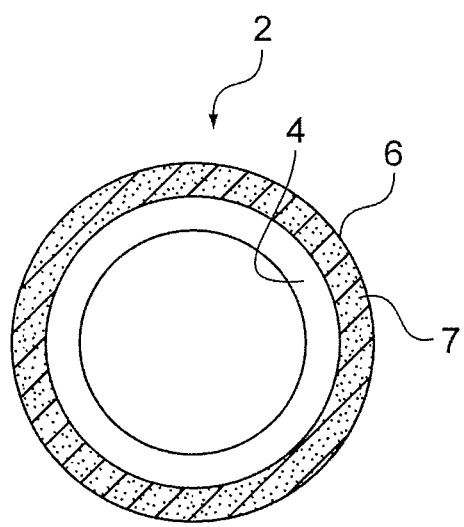
FIG. 1B is a cross-sectional view of an embodiment of an endoprosthesis.

Referring to FIGS. 1A and 1B endoprosthesis 2 (as shown, a stent) includes a bioerodible layer 4 and an antioxidant-containing layer 6 ("antioxidant layer 6") disposed radially outward and on a surface of the bioerodible layer. Bioerodible layer 4, which can include a bioerodible material (e.g., a metal) such as a magnesium alloy, is a tubular body capable of maintaining the patency of a bodily lumen after implantation and is capable of eroding within the bodily lumen. Antioxidant layer 6 provides therapeutic benefits, such as inhibiting restenosis as well as affecting (e.g., reducing or inhibiting) the erosion of bioerodible layer 4 to allow the endoprosthesis to maintain structural integrity (e.g., patency) for a longer duration. Examples of antioxidants in antioxidant layer 6 include phenolic compounds (e.g., isoeugenol, eugenol, and acetyl eugenol), polyphenols, phenols, and any mixtures thereof. As shown, antioxidant layer 6 is disposed radially outward of bioerodible layer 4, but alternatively or additionally, the antioxidant layer can be disposed radially inward of the bioerodible layer.

Antioxidants can inhibit or reduce oxidative processes caused by oxygen or free radicals. The use of an antioxidant in an erodible endoprosthesis can provide a number of advantages. The antioxidant can inhibit restenosis by inhibiting lipid peroxidation. Antioxidants such as eugenol compounds can have an inhibitory effect on LDL suppression of free radical cascade of lipid peroxidation and reduction of LDL to its receptor, as well as provide anti-inflammatory effects. In addition, the antioxidant presence on its own as a coating or in a carrier with another material acts as a barrier that modifies the exposure of the bioerodible endoprosthesis to body fluids and thus the degradation processes which occur upon exposure to body fluids. Moreover, the presence of an antioxidant can chemically inhibit corrosive degradation, particularly of metals. Without being bound by theory, it is believed that in a biological fluid, an antioxidant can reduce (e.g., inhibit) free radical reactions by decreasing the level of active products from oxygen reduction and/or sequestering (e.g., binding to a protein) a transition metal group such as Fe and Cu to reduce the formation of oxidants. Further discussion of antioxidants is provided in Chaieb et al., *Applied Surface Science*, 2005, 246, 199; Lee et al., *Journal of Dentistry*, 2000, 28, 69; Satoh et al., *Anticancer Res.*, 1998, 18, 1549; Damiani et al., *Vascular Pharmal.* 2003, 40, 59; Stoclet et al., *European Journal of Pharmacology*, 2005, 500, 461; Ito et al., *Food and Chemical Toxicology*, 2005, 43, 461; Naderi et al., *Molecular and Cellular Biochemistry*, 2004, 267, 59; Molnar et al., *International Immunopharmacology*, 2005, 5, 849; Kim et al., *Circ. J.*, 2005, 69, 101; Andión et al., *Corrosion Science*, 2002, 44, 2805-2816; and Ou et al., *Food and Chemical Toxicology*, 2006, 44, 1485-1495, the entire contents of each of which is hereby incorporated by reference.

As an example, an antioxidant can be low-molecular weight compounds (e.g., isoeugenol, eugenol, acetyl eugenol, polyphenols, phenols (including antioxidants of the phenolic class of compounds such as phenols, polyphenols, and phenolic compounds), tocopherols, anethol, geraniol, limonene, linalool, p-cymol, pulegone, thymol, ubiquitol-10, ascorbic acid, β-carotene, lycopene, glutathione, uric acid, bilirubin, carvediol, *Curcuma longa*, and *Ocimum sanctum*. Classes of antioxidants can include phenols, phenolic acids, flavonoids, anthocyanins, catechins, flavones, flavonols, flavanones, isoflavones, lignins, proanthocyanidins, procyanidins, stilbenes, tannins, spice antioxidants, and plant-derived antioxidants. In some embodiments, an antioxidant is a high-molecular weight compound such as a protein (e.g., albumin, transferrin, haptoglobin, haemopexin, caeruloplasmin, ferritin, superoxide dismutase, catalase, glutation reductase, glutathione peroxidase, etc.) and/or a polymer (e.g., polymeric phenols). In some embodiments, the antioxidant is polymeric. The polymeric antioxidant can be provided as a layer directly on the bioerodible layer. In embodiments, the polymeric antioxidant layer is directly deposited onto an endoprosthesis by electropolymerization, and/or the polymeric antioxidant layer is dissolved in a solvent and applied to the endoprosthesis. A plurality of different antioxidants can be used.

The antioxidant compound can be provided as a layer directly on the bioerodible layer or incorporated into the bioerodible layer, or incorporated into a bioerodible or non-bioerodible carrier layer on the bioerodible material. The antioxidant can be released from the carrier by diffusion through the carrier and/or erosion of the carrier in the case where a bioerodible carrier is used. The antioxidant can be noncovalently bonded, e.g. adsorbed, or covalently bonded to the carrier or the bioerodible material, e.g. by copolymerization with the carrier. Further examples of antioxidants are described, for example, in Ivanova et al., *Experimental Pathology and Parasitology*, 2000, 4, 49; Frei, B., *Proceedings—Society for Experimental Biology and Medicine*, 1999, 222, 196; Mohanty et al., *BMC Complementary and Alternative Medicine*, 2006, 6:3; Suhaj, M., *Journal of Food Composition and Analysis*, 2006, 19, 531-537; Ratnam et al., *Journal of Controlled Release*, 2006, 113, 189-207; Gurib-Fakim, A., *Molecular Aspects of Medicine*, 2006, 27, 1-93; Arts et al., *Am. J. Clin. Nutr.*, 2005, 81(1), 317S-325S; Wallerath er al., *Nitric Oxide*, 2005, 12(2), 97-104; Grassi et arla *Am. J. Clin. Nutr.*, 2005, 81(3), 611-614; Kim et al., *Crit. Rev. Food Sci. Nutr.*, 2004, 44(4), 253-273; Lambert et al., *Am. J. Clin. Nutr.*, 2005, 81(1), 284S-291S; Moskaug et al., *Am. J. Clin. Nutr.*, 2005, 81(1), 277S-283S; and Williamson et al., *Am. J. Clin. Nutr.*, 2005, 81(1), 243S-255S.

In FIGS. 1A and 1B, antioxidant layer 6 has an antioxidant (shading) distributed uniformly within a matrix of a biocompatible carrier 7. Suitable carriers include, for example, bioerodible or non bioerodible polymers or metals. A bioerodible carrier (e.g., a bioerodible polymer) can erode over time and expose the incorporated antioxidant for gradual release. A bioerodible carrier can inhibit direct contact of body fluids with bioerodible layer 4 and reduce the bioerosion rate of the endoprosthesis. Suitable bioerodible polymer carriers include polylactic acid (PLA), polylactic glycolic acid (PLGA), polyanhydrides (e.g., poly(ester anhydride)s, fatty acid-based polyanhydrides, amino acid-based polyanhydrides), polyesters, polyester-polyanhydride blends, polycarbonate-polyanhydride blends, and/or combinations thereof. Bioerodible polymers such as polyanhydrides are described, for example, in Kumar et al., *Advanced Drug Delivery Reviews*, 2002, 54, 889. Bioerodible polymers are also described in U.S. Ser. No. 10/958,435 (U.S. Patent Application Publication No. 2005/0216074), filed Oct. 5, 2004. The antioxidant and the polymer can be dissolved in a solvent and applied to bioerodible layer 4, the antioxidant and the polymer can be blended together and applied to the bioerodible layer, and/or the antioxidant and the polymer can be formed into a composite in a solvent and applied to the bioerodible layer. The antioxidant can be applied (e.g., adsorbed) to antioxidant layer using, for example, vapor phase adsorption and solution phase adsorption methods (such as solution impregnation). Varying amounts of the antioxidant can be dispersed (uniformly or non-uniformly) within antioxidant layer 6. For example, the antioxidant can be present from about 0.5 percent by weight of the antioxidant layer 6 (e.g., from about 1 percent by weight, from about 2 percent by weight, from about 5 percent by weight, from about 10 percent by weight, from about 15 percent by weight, from about 20 percent by weight, from about 25 percent by weight) to about 30 percent by weight of the antioxidant layer (e.g., to about 25 percent by weight, to about 20 percent by weight, to about 15 percent by weight, to about 10 percent by weight, to about 5 percent by weight, to about 2 percent by weight). The carrier can include one or more bioerodible materials and/or one or more non-bioerodible materials that has a different chemical composition than a composition of material in bioerodible layer 4.

Figure 2A:
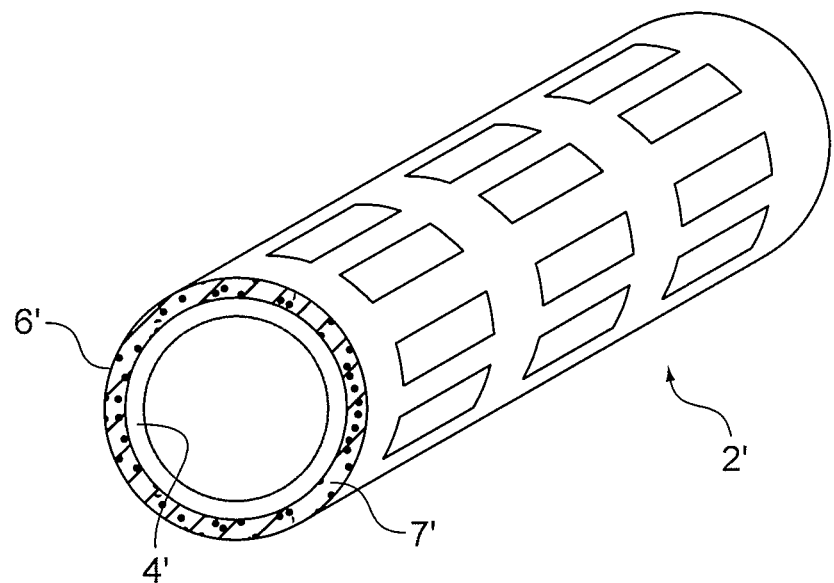
FIG. 2A is a perspective view of an embodiment of an endoprosthesis.
Figure 2B:
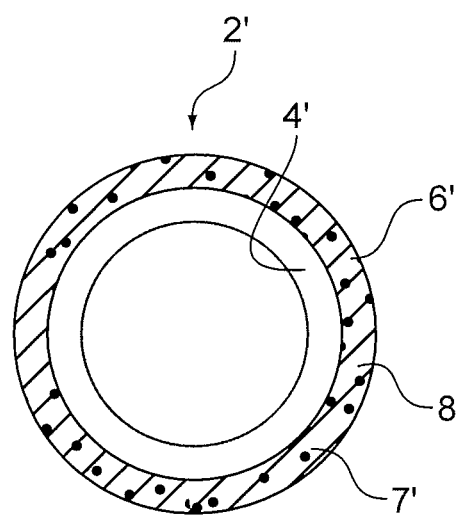
FIG. 2B is a cross-sectional view of an embodiment of an endoprosthesis.

Referring to FIGS. 2A and 2B, endoprosthesis 2' includes a bioerodible layer 4' and an antioxidant layer 6' radially outward of the bioerodible layer 4'. The antioxidant layer 6' includes (e.g., is formed of) a bioerodible or non-bioerodible carrier 7' having a plurality of pores 8. The antioxidant is dispersed (e.g., sorbed) in the pores in antioxidant layer 6'. Pores 8 increase the total free volume and surface area of antioxidant layer 6', and allow more antioxidant to be loaded in and delivered from antioxidant layer 6'. The antioxidant layer can be formed of a bioerodible or non-bioerodible metal, polymer or ceramic in which pores are created. For example, the carrier can be formed of the same material or a different material as the bioerodible layer 4'. For example, carrier and the bioerodible layer can be formed of the same metal. Antioxidant layer 6' can be made by forming pores 8 and applying the antioxidant to the porous outer surface. In some embodiments, a first layer of carrier material is formed on the surface of the bioerodible layer and pores are formed by creating a number of holes (e.g., by laser ablation) and the holes are filled or partially filled with an antioxidant 6. A second layer of a same or different polymer can be coated (e.g., by spraying) onto the endoprosthesis. Pores can also be formed during the coating process by techniques discussed below. The pores can be formed directly into the surface of the bioerodible layer 4' without the use of a carrier. Pores 8 can have an average diameter of from about 10 nm (e.g., from about 20 nm, from about 50 nm, from about 100 nm, from about 200 nm, from about 500 nm, from about 700 nm, from about 1 μm, from about 1.5 μm, from about 2 μm, from about 2.5 μm, from about 3 μm, from about 3.5 μm, from about 4 μm, from about 4.5 μm) to about 10 μm (e.g., to about 9 μm, to about 8 μm, to about 7 μm, to about 6 μm, to about 5 μm, to about 4.5 μm, to about 4 μm, to about 3 μm, to about 2.5 μm, to about 2 μm, to about 1.5 μm, to about 1 μm, to about 750 nm, to about 500 nm, to about 250 nm, to about 100 nm, to about 75 nm, to about 50 nm, to about 25 nm). Pores 8 can have an average surface area of from about 300 $nm^2$ (e.g. from about 1,000 $nm^2$, from about 5,000 $nm^2$, from about 30,000 nm from about 0.5 $\mu m^2$, from about 6 $\mu m^2$, from about 10 $\mu m^2$, from about 20 $\mu m^2$, from about 30 $\mu m^2$, from about 40 $\mu m^2$, from about 50 $\mu m^2$, from about 65 $\mu m^2$) to about 350 $\mu m^2$ (e.g., to about 300 $\mu m^2$, to about 250 $\mu m^2$, to about 200 $\mu m^2$, to about 150 $\mu m^2$, to about 100 $\mu m^2$, to about 70 $\mu m^2$, to about 65 $\mu m^2$, to about 50 $\mu m^2$, to about 40 $\mu m^2$, to about 30 $\mu m^2$, to about 20 $\mu m^2$, to about 10 $\mu m^2$, to about 6 $\mu m^2$, to about 0.5 $\mu m^2$, to about 30,000 $nm^2$, to about 5,000 $nm^2$, to about 1000 $nm^2$). Pores 8 can also be expressed by average volume. In some embodiments, pores 8 can be from about 500 $nm^3$ (e.g., from about 0.00005 $\mu m^3$, from about 0.0005 $\mu m^3$, from about 0.005 $\mu m^3$, from about 0.05 $\mu m^3$, from about 0.5 $\mu m^3$, from about 1 $\mu m^3$, from about 5 $\mu m^3$, from about 35 $\mu m^3$, from about 50 $\mu m^3$) to about 550 $\mu m^3$ (e.g., to about 450 $\mu m^3$, to about 300 $\mu dm^3$, to about 200 $\mu m^3$, to about 100 $\mu m^3$, to about 75 $\mu m^3$, to about 40 $\mu m^3$, to about 10 $\mu m^3$, to about 5 $\mu m^3$, to about 1 $\mu m^3$, to about 0.5 $\mu m^3$, to about 0.05 $\mu m^3$, to about 0.005 $\mu m^3$, to about 0.00005 $\mu m^3$). Pores can occupy a portion of antioxidant layer 6'. In some embodiments, pores range from about 1% by volume of the antioxidant layer (e.g., from about 5% by volume, from about 10% by volume, from about 25% by volume, from about 50% by volume) to about 75% by volume of the antioxidant layer (e.g., to about 60% by volume, to about 50% by volume, to about 40% by volume, to about 30% by volume, to about 25% by volume, to about 20% by volume, to about 10% by volume, to about 5% by volume. The antioxidant can be applied (e.g., adsorbed) to antioxidant layer 6' using, for example, vapor phase adsorption and solution phase adsorption methods (such as solution impregnation). The antioxidant can be sorbed (uniformly or non-uniformly) within antioxidant layer 6' from about 0.5% by weight of the antioxidant layer (e.g., from about 1% by weight, from about 5% by weight, from about 10% by weight, from about 20% by weight, from about 30% by weight, from about 40% by weight) to about 50% by weight of the antioxidant layer (e.g., to about 45% by weight, to about 40% by weight, to about 30% by weight, to about 25% by weight, to about 15% by weight, to about 10% by weight, to about 5% by weight, to about 2% by weight, to about 1% by weight).

Figure 3A:
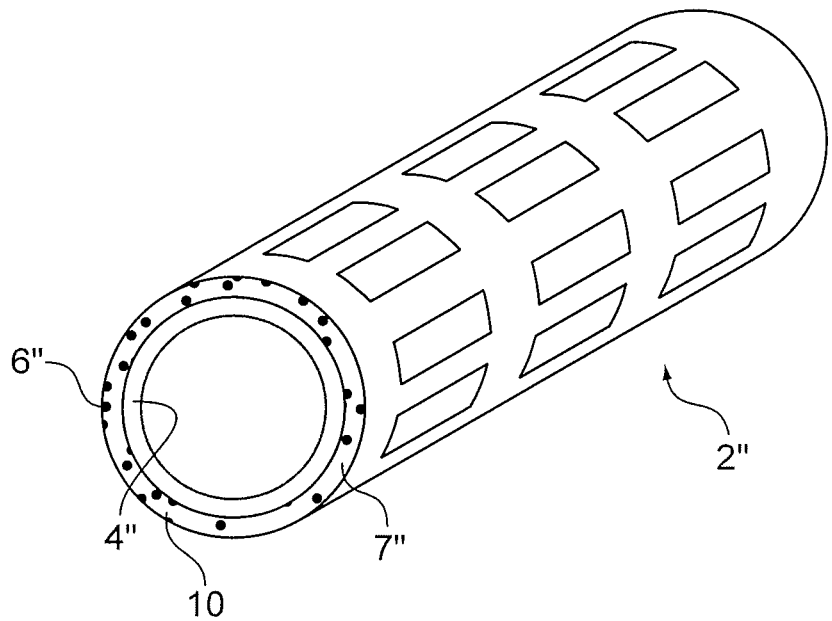
FIG. 3A is a perspective view of an embodiment of an endoprosthesis.
Figure 3B:
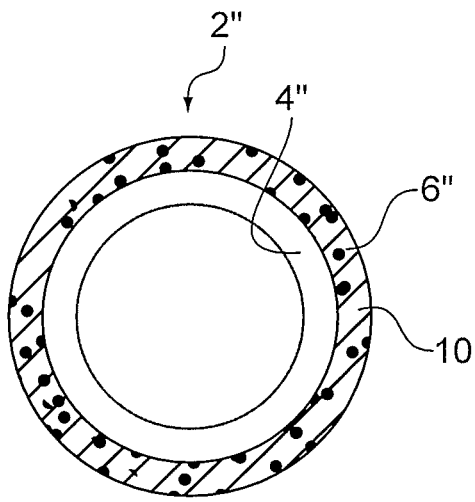
FIG. 3B is a cross-sectional view of an embodiment of an endoprosthesis.
Figure 3C:
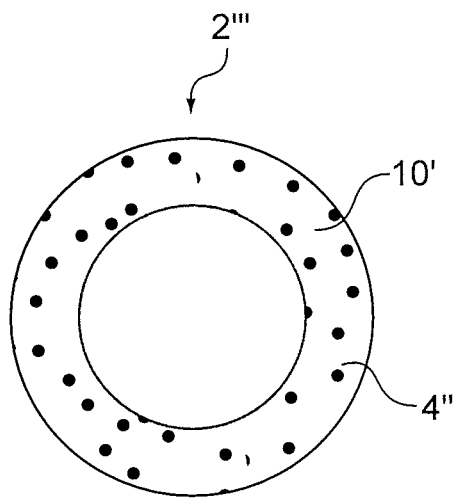
FIG. 3C is a cross-sectional view of another embodiment of an endoprosthesis.

Referring to FIGS. 3A, 3B, and 3C, endoprosthesis 2" and 2''' include particles 10, 10', which carry one or more antioxidants. Particles 10, 10' can be dispersed throughout an endoprosthesis, or can be dispersed in an antioxidant layer including a carrier of the types discussed above on an endoprosthesis. Referring to FIGS. 3A and 3B, endoprosthesis 2" includes a bioerodible layer 4", and an antioxidant layer 6" including particles 10 dispersed in a carrier 7" of the types described above. Referring to FIG. 3C, endoprosthesis 2''' includes particles 10' dispersed throughout the erodible layer 4' of the endoprosthesis. In other embodiments, the particles are absorbed or bonded to the surface of the erodible layer. The particles can include (e.g., is formed of) a bioerodible material, such as zinc oxide, poly(γ-benzyl-L-glutamate) (PBLG), poly(β-benzyl-L-aspartate) (PBLA), poly-D,L-lactide-co-glycolide (PLGA), and polylactic acid (PLA), that encapsulates the antioxidant and allows the antioxidant to be delivered to the body. Particles 10 (e.g., nanoparticles) can have an average diameter of from about 100 nm (from about 200 nm, from about 400 nm, from about 600 nm, from about 1 μm, from about 2 μm, from about 3 μm, from about 4 μm) to about 5 μm (to about 4.5 μm, to about 4 μm, to about 3.5 μm, to about 3 μm, to about 2 μm, to about 1 μm, to about 800 nm, to about 500 nm, to about 300 nm, to about 200 nm). Particles 10 (e.g., nanoparticles) can also be expressed by volume. In some embodiments, particles 10 can have a volume of from about 0.0005 $\mu m^3$ (e.g., from about from about 0.005 $\mu m^3$, from about 0.05 $\mu m^3$, from about 0.5 $\mu m^3$, from about 5 $\mu m^3$, from about 50 $\mu M^3$) to about 70 $\mu m^3$ (e.g., to about 60 $\mu m^3$, to about 50 $\mu m^3$, to about 5 $\mu m^3$, to about 0.5 $\mu m^3$, to about 0.05 $\mu m^3$, to about 0.005 $\mu m^3$, to about 0.0025 $\mu m^3$). The antioxidant can be present in varying amounts within the particles. For example, the antioxidant can be present from about 5 weight percent of particles 10 (e.g., from about 10 weight percent, from about 15 weight percent, from about 20 weight percent, from about 25 weight percent) to about 30 weight percent of particles 10 (e.g., to about 25 weight percent, to about 20 weight percent, to about 15 weight percent, to about 10 weight percent, to about 7 weight percent). Prior to implantation, particles 10 can be present from about 0.5 weight percent of antioxidant layer 6" (e.g., from about 1 weight percent, from about 2 weight percent, from about 5 weight percent, from about 10 weight percent, from about 15 weight percent) to about 20 weight percent of antioxidant layer 6" (e.g., to about 17 weight percent, to about 15 weight percent, to about 10 weight percent, to about 5 weight percent, to about 3 weight percent, to about 2 weight percent). Particles 10 can be substantially spherical or any other shape. Suitable processes for making particles include spraying (e.g., electrospraying), emulsion processes, and dispersion polymerization. Further processes for making particles are described, for example, in Jiang, S. B., *Materials Science and Engineering*, 2006, 418, 199.

Figure 4:
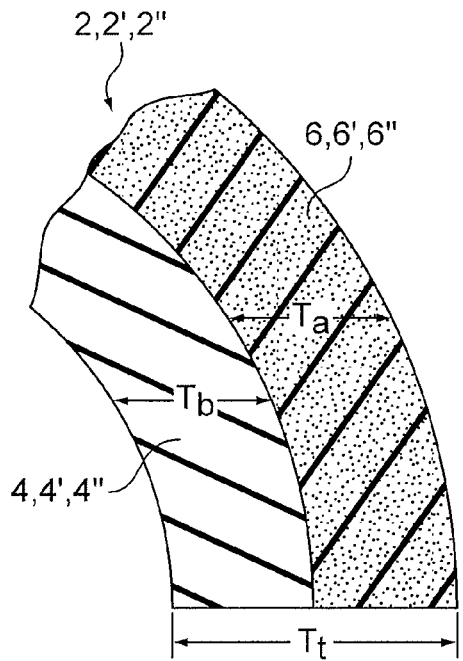
FIG. 4 is an enlarged cross-sectional view of a region of an endoprosthesis.

Referring now to FIG. 4, the thicknesses for bioerodible layer 4, 4', 4" and antioxidant layer 6, 6', 6" is illustrated. In some embodiments, bioerodible layer 4, 4', 4" has a total thickness ($T_b$) that is from about 5 μm (e.g., from about 10 μm, from about 20 μm, from about 30 μm, from about 40 μm, from about 50 μm, from about 60 μm from about 80 μm, from about 100 μm) to about 200 μm (e.g., to about 175 μm, to about 150 μm, to about 100 μm, to about 85 μm, to about 75 μm, to about 50 μm, to about 35 μm, to about 20 μm, to about 15 μm). In some embodiments, antioxidant layer 6, 6', 6" has a total thickness ($T_a$) that is from about 0.5 μm (e.g., from about 1 μm, from about 2 μm, from about 3 μm, from about 4 μm, from about 5 μm, from about 6 μm, from about 7 μm, from about 8 μm) to about 10 μm (e.g., to about 9 Mm, to about 8 μm, to about 7 μm, to about 6 μm, to about 5 μm, to about 4 μm, to about 3 μm, to about 2 μm, to about 1 μm). Total $T_1$ can be from about 10 μm (e.g., from about 20 μm, from about 30 μm, from about 40 μm, from about 50 μm, from about 60 μm from about 80 μm, from about 100 μm) to about 200 μm (e.g., to about 150 μm, to about 100 μm, to about 85 μm, to about 75 μm, to about 50 μm, to about 35 μm, to about 20 μm, to about 15 μm).

The thicknesses for bioerodible layer 4, 4', 4" and antioxidant layer 6, 6', 6" can also be expressed relative to the total thickness ($T_t$) of endoprosthesis 2, 2', 2". In some embodiments, bioerodible layer 4, 4', 4" has a total thickness $T_b$ that is from about 10 percent of $T_t$ (e.g., from about 35 percent, from about 60 percent, from about 70%, from about 80 percent) to about 90% of $T_t$ (e.g., to about 80%, to about 70%, to about 50%, to about 35%, to about 15%, to about 10%). In some embodiments, antioxidant layer 6, 6', 6" has a total thickness $T_a$ that is from about 10 percent of $T_t$ (e.g., from about 35 percent, from about 60 percent, from about 80 percent) to about 90 percent of $T_t$ (e.g., to about 80%, to about 75 percent, to about 50 percent, to about 45%, to about 35%, to about 25 percent, to about 15%, to about 10%, to about 5%).

Figure 5:
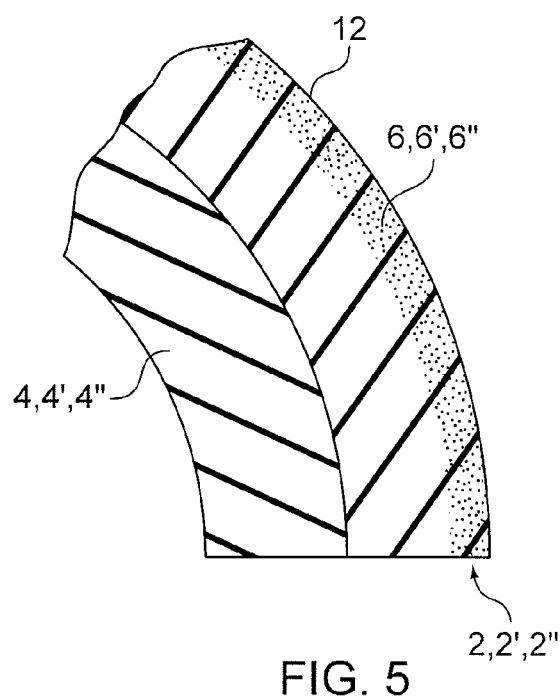
FIG. 5 is an enlarged cross-sectional view of a region of an embodiment of an endoprosthesis.
Figure 6:
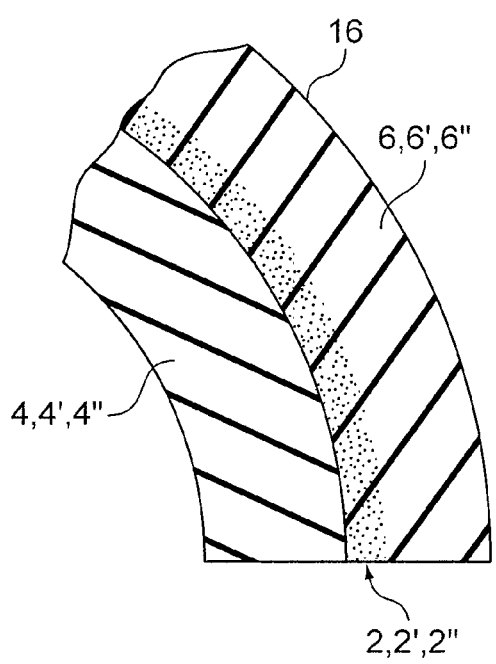
FIG. 6 is an enlarged cross-sectional view of a region of an embodiment of an endoprosthesis.

Referring to FIGS. 5 and 6, within an antioxidant layer, the antioxidant can be equally distributed throughout or unequally distributed. For example, the antioxidant, such as that located near the outer peripheral region of an endoprosthesis, can be distributed in a gradient manner along the radial direction of the endoprosthesis. Referring to FIG. 5, the antioxidant (shading) can increase in concentration toward an outer periphery 12 of an endoprosthesis 2, 2', 2". Greater release of the antioxidant can be achieved during the early stages of the endoprosthesis lifetime following implantation. Referring to FIG. 6, the antioxidant (shading) can decrease in concentration toward an outer periphery 14 of an endoprosthesis 2, 2', 2". The antioxidant release can increase during the endoprosthesis lifetime within a vessel. A decrease or increase in concentration of an antioxidant within an endoprosthesis can occur linearly, non-linearly (e.g., exponentially), and/or in a stepwise manner in order to tailor the release of the antioxidant. In some embodiments, an antioxidant layer includes one or more zones having an equal distribution of antioxidant throughout, and one or more zones having an unequal distribution of antioxidant, in any combination.

Figure 7:
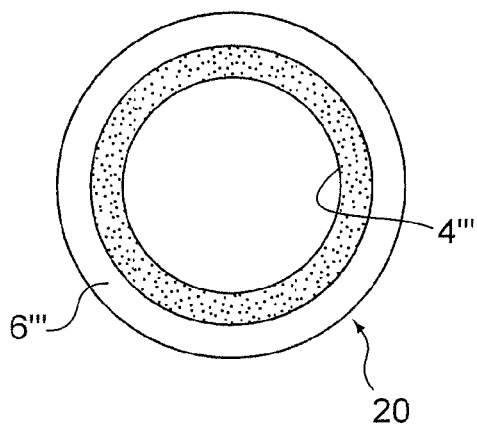
FIG. 7 is a cross-sectional view of an embodiment of an endoprosthesis.
Figure 8:
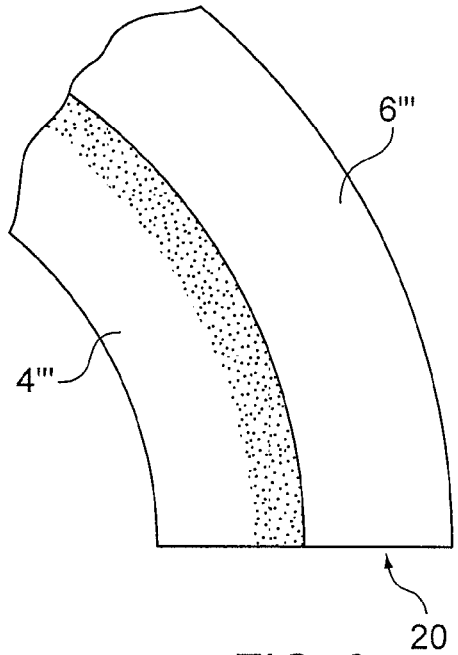
FIG. 8 is an enlarged cross-sectional view of a region of an embodiment of an endoprosthesis.
Figure 9:
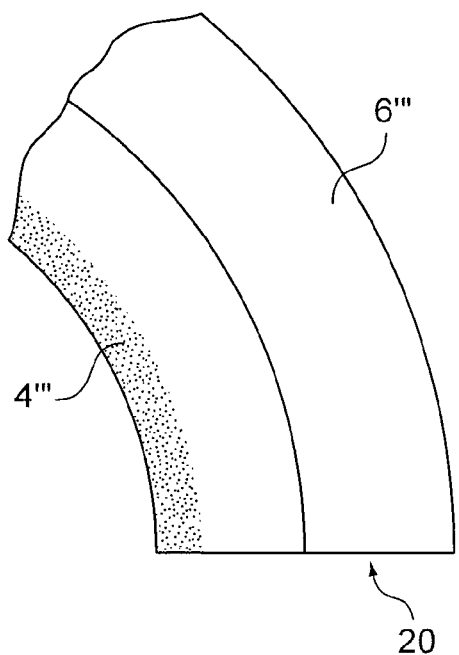
FIG. 9 is an enlarged cross-sectional view of a region of an embodiment of an endoprosthesis.

Referring to FIGS. 7-9, similarly, in embodiments in which the antioxidant layer is radially inward of the bioerodible layer, the antioxidant can be equally distributed throughout or unequally distributed. FIG. 7 shows an endoprosthesis 20 including an antioxidant layer 4''' located radially inwardly of a bioerodible layer 6''', for example, to avoid direct contact of the antioxidant with a vessel. The antioxidant can be uniformly dispersed within antioxidant layer 4''', which defines an inner circumferential region of endoprosthesis 20. In some embodiments, the antioxidant in antioxidant layer 4''' can be dispersed in a gradient manner along a radius of endoprosthesis 20 to tune the release of the antioxidant within a vessel. For example, as shown in FIG. 8, the antioxidant can increase in concentration radially outward, or as shown in FIG. 9, the antioxidant can decrease in concentration radially outward. A decrease or increase in concentration of the antioxidant within an endoprosthesis can occur linearly, exponentially, or in a stepwise manner in order to tailor the release of the antioxidant. In some embodiments, an antioxidant layer includes one or more zones having an equal distribution of antioxidant throughout, and one or more zones having an unequal distribution of antioxidant, in any combination.

Figure 10:
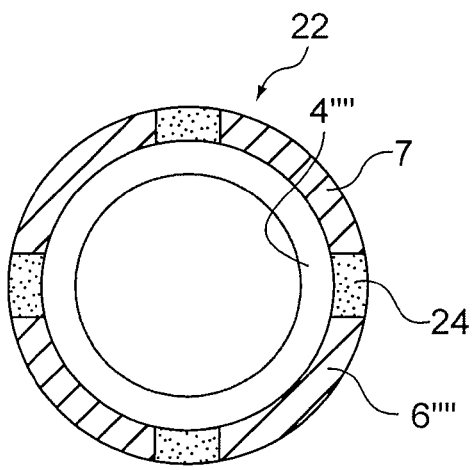
FIG. 10 is an enlarged cross-sectional view of an embodiment of an endoprosthesis FIG. 11a perspective view of an embodiment of an endoprosthesis.
Figure 11:
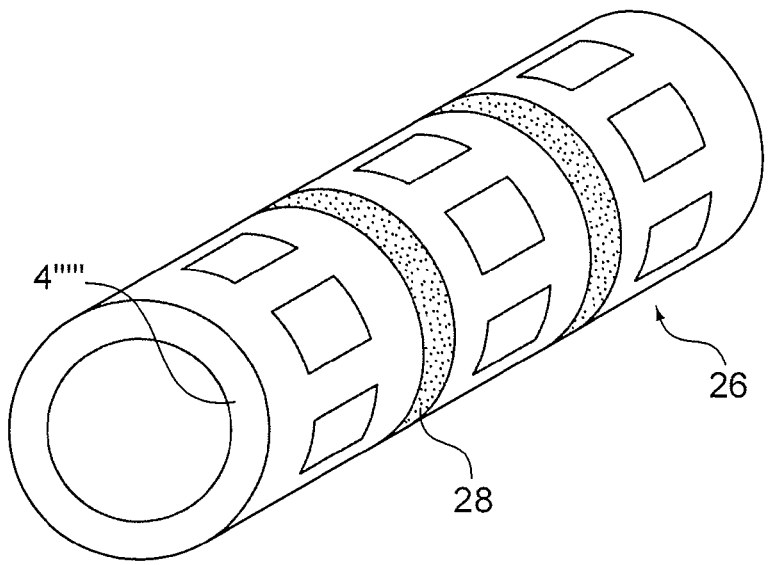
Figure 12:
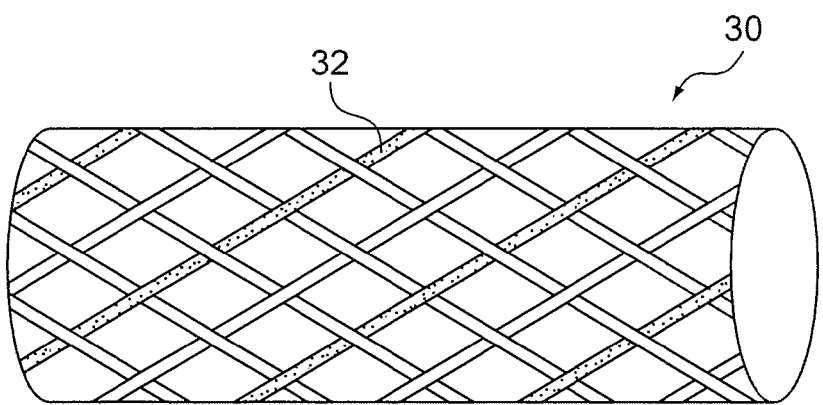
FIG. 12 is a perspective view of an embodiment of an endoprosthesis.

Referring to FIGS. 10 and 11, the antioxidant layer be on selected portion(s) of the bioerodible layer, for example, to tune the release of antioxidant, to treat specific locations in a vessel, or to create a desirable degradation pattern. For example, FIG. 10 shows an endoprosthesis 22 having a bioerodible layer 4'''', and an antioxidant layer 6'''' including an antioxidant 24 located in strips extending along the length of. As another example, FIG. 11 shows an endoprosthesis 26 having a bioerodible layer 4'''', and an antioxidant 28 applied as circular bands on the bioerodible layer. Referring to FIG. 12, an endoprosthesis 30 includes a series of generally circumferential interconnected struts 32, and an antioxidant 34 can be applied to selected struts to reduce the degradation rate of the struts to maintain structural features of the struts compared to struts not including the antioxidant. An antioxidant can have a patterned distribution on the bioerodible layer, and/or along the length of an endoprosthesis Referring to FIG. 13, a method 100 of making an endoprosthesis as described herein is shown. Method 100 includes forming a bioerodible tube (step 102), forming a pre-endoprosthesis from the bioerodible tube (step 104), and applying one or more antioxidants to the pre-endoprosthesis (step 106) to form an endoprosthesis. In other embodiments, one or more antioxidants are applied to the bioerodible tube, and the tube with the applied antioxidant(s) is subsequently formed into an endoprosthesis.

The bioerodible tube can be formed (step 102) by manufacturing a tubular member including (e.g., is formed of) one or more bioerodible materials and capable of supporting a bodily lumen. For example, a mass of bioerodible material can be machined into a rod that is subsequently drilled to form the tubular member. As another example, a sheet of bioerodible material can be rolled to form a tubular member with overlapping portions, or opposing end portions of the rolled sheet can be joined (e.g., welded) together to form a tubular member. A bioerodible material can also be extruded to form a tubular member. The bioerodible or erodible material can be a substantially pure metallic element, or an alloy. The alloy can include metal and non-metal components, for example, the alloy can be a metallic alloy, a ceramic, or a metal matrix composite. Examples of metallic elements include iron and magnesium. Examples of alloys include iron alloys having, by weight, 88-99.8% iron, 0.1-7% chromium, 0-3.5% nickel, and less than 5% of other elements (e.g., magnesium and/or zinc); or 90-96% iron, 3-6% chromium and 0-3% nickel plus 0-5% other metals. Other examples of alloys include magnesium alloys, such as, by weight, 50-98% magnesium, 0-40% lithium, 0-5% iron and less than 5% other metals or rare earths; or 79-97% magnesium, 2-5% aluminum, 0-12% lithium and 1-4% rare earths (such as cerium, lanthanum, neodymium and/or praseodymium); or 85-91% magnesium, 6-12% lithium, 2% aluminum and 1% rare earths; or 86-97% magnesium, 0-8% lithium, 2%-4% aluminum and 1-2% rare earths; or 8.5-9.5% aluminum, 0.15%-0.4% manganese, 0.45-0.9% zinc and the remainder magnesium; or 4.5-5.3% aluminum, 0.28%-0.5% manganese and the remainder magnesium; or 55-65% magnesium, 30-40% lithium and 0-5% other metals and/or rare earths. Magnesium alloys are also available under the names AZ91D, AM50A, and AE42. Other erodible materials are described in Bolz, U.S. Pat. No. 6,287, 332 (e.g., zinc-titanium alloy and sodium-magnesium alloys); Heublein, U.S. Patent Application 2002000406; and Park, *Science and Technology of Advanced Materials,* 2, 73-78 (2001), all of which are hereby incorporated by reference herein in their entirety. In particular, Park describes Mg—X—Ca alloys, e.g., Mg—Al—Si—Ca, Mg—Zn—Ca alloys. The bioerodible tube can include more than one bioerodible material, such as different bioerodible materials physically mixed together, multiple layers of different bioerodible materials, and/or multiple sections of different bioerodible materials along a direction (e.g., length) of the tube. In other embodiments, the bioerodible material is a bioerodible polymer.

Figure 13:
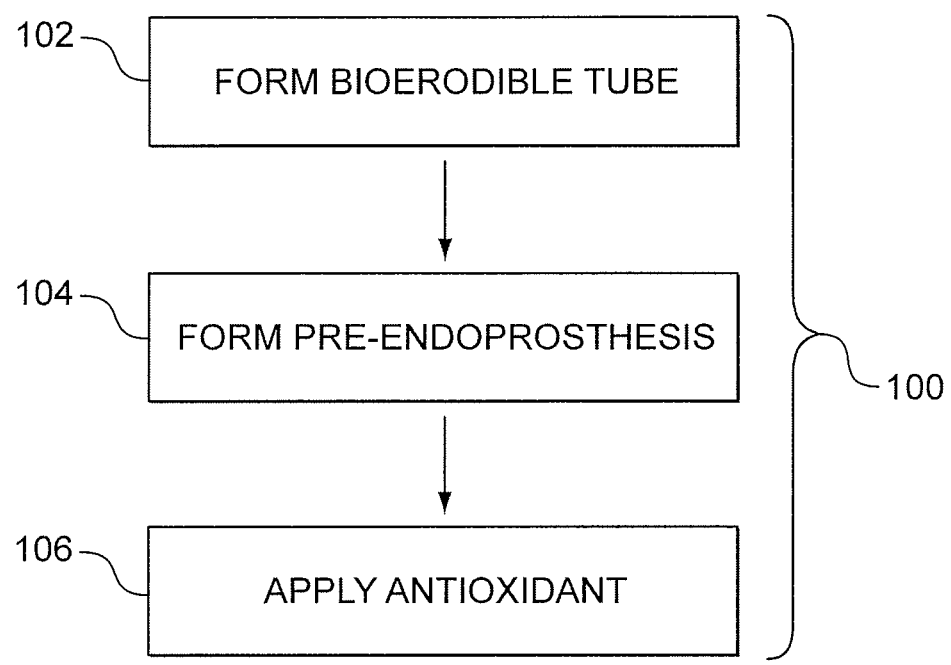
FIG. 13 is a sequence illustrating a method of making an endoprosthesis.

As shown in FIG. 13, after the bioerodible tube is formed, the tube is formed into a pre-endoprosthesis (step 104). For examples, selected portions of the tube can be removed to form bands and connectors by laser cutting, as described in U.S. Pat. No. 5,780,807, hereby incorporated by reference in its entirety. Other methods of removing portions of the tube can be used, such as mechanical machining (e.g., micromachining, grit blasting or honing), electrical discharge machining (EDM), and photoetching (e.g., acid photoetching). The pre-endoprosthesis can be etched and/or electropolished to provide a selected finish. In certain embodiments, such as jelly-roll type endoprostheses, step 104 is omitted.

Prior to apply the antioxidant, selected surfaces (e.g., inner surface) or portions (e.g., portion between the end portions of the endoprosthesis) of the pre-endoprosthesis can be masked so that the antioxidant will not be applied to the masked surfaces or portions.

In some embodiments, prior to applying the antioxidant, pores are formed on/in the pre-endoprosthesis, the bioerodible tube, and/or a coating layer. Pores can be formed by a variety of methods (e.g., micro-arc surface modification, sol-gel templating process, plasma spraying, adding foaming structures into a melt or liquid metal, melting a powder compact containing a gas evolving element or a space holder material, incorporating a removable scaffold (e.g., polyurethane) in a metal powder/slurry prior to sintering, sintering hollow spheres, sintering fibers, combustion synthesis, powder metallurgy, bonded fiber arrays, wire mesh constructions, vapor deposition, three-dimensional printing, and/or electrical discharge compaction). In some embodiments, pores can be formed by incorporating embedded microparticles and/or compounds (e.g., a salt) within the antioxidant layer (e.g., a polymerizable monomer, a polymer, a metal alloy), forming the antioxidant layer, and removing (e.g., dissolving, leaching, burning) the microparticles and/or compounds to form pores at locations where the microparticles and/or compounds were embedded. Removable (e.g., dissolvable) microparticles can be purchased, for example, from Micro-Particles GmbH. In some embodiments, pores are formed by using a gas as a porogen, bonding fibers, and/or phase separation in materials such as polymers, metals, or metal alloys. Methods for forming porous structures are described, for example, in Ryan et al., *Biomaterials,* 2006, 27, 2651; Liao et al., *Journal of Biomedical Materials Research,* 2001, 59(4), 676; Mikos et al., *Electronic Jouirnal of Biotechnology,* 2000, 3(2), 1; Widmer et al., *Biomaterials,* 1998, 19, 1945; and Gomes et al., *Materials Science and Engineering C,* 2002, 20, 19.

Next, the antioxidant(s) can applied to the pre-endoprosthesis (step 106) to form an endoprosthesis. The antioxidant and a polymer (e.g., polylactic acid (PLA), polylactic glycolic acid (PLGA), polyanhydrides (e.g., poly(ester anhydride)s, fatty acid-based polyanhydrides, amino acid-based polyanhydrides), polyesters, polyester-polyanhydride blends, polyearbonate-polyanhydride blends, and/or combinations thereof) can be dissolved in a solvent and applied to the pre-endoprosthesis, the antioxidant and the polymer can be blended together (e.g., in a manner that the antioxidant is mixed, embedded or encapsulated in a polymer matrix) and applied to the pre-endoprosthesis, and/or the antioxidant and the polymer can be formed into a composite in a solvent and applied to the pre-endoprosthesis. In some embodiments, the antioxidant layer is directly deposited onto an endoprosthesis (e.g., by electropolymerization). Methods for depositing an antioxidant is described, for example, in Andidn et al., *Corrosion Science.,* 2002, 44, 2805-2816. The antioxidant can be applied (e.g., adsorbed on the surfaces defining the pores, adsorbed on a substantially pore-free surface, or dispersed within the pores) directly to the pre-endoprosthesis using vapor phase adsorption, solution phase adsorption methods (e.g., solution impregnation). The antioxidant can also be incorporated with (e.g., encapsulated in) particles including a second, different bioerodible material than the bioerodible material in the pre-endoprosthesis, the second bioerodible material with the antioxidant can be applied to the pre-endoprosthesis. The second bioerodible material can also be combined with the bioerodible material and co-extruded with a bioerodible material free of the second bioerodible material. In some embodiments, more than one method of applying an antioxidant to a pre-endoprosthesis can be used. As an example, a pre-endoprosthesis may be coated with an antioxidant in a polymer matrix, and impregnated with a bioerodible material-encapsulated antioxidant. Methods for incorporating one material in another are described, for example, in Jiang, S. B., *Materials Science and Engineering,* 2006, 418, 199.

In certain embodiments, the antioxidant can be applied to a pre-endoprosthesis in one layer, or in multiple layers (e.g., at least two layers, at least three layers, at least four layers, at least five layers) in order, for example, to provide greater control over the amount and variety of the antioxidant. For example, the layers can have different concentrations of one or more antioxidants (e.g., to provide a gradient or other profiles of antioxidants), and/or the layers can have different compositions of antioxidants. Within an antioxidant layer, the concentrations and/or compositions of the antioxidant can be the same or different to provide a selected antioxidant profile. For example, the end portions of the endoprosthesis can have a greater concentration of antioxidant than the intermediate portion of the endoprosthesis to provide reduced restenosis. The antioxidant layers can be applied the same way or in different ways. For example, a first, innermost antioxidant layer can be sorbed to a porous surface of the pre-endoprosthesis, and a second, outer antioxidant layer can include an antioxidant and a polymer that are applied to the first layer.

As indicated above, in some embodiments, the antioxidant(s) is applied to the bioerodible tube prior to forming the bioerodible tube into an endoprosthesis (if necessary). As a result, the endoprosthesis can have its outer and inner surfaces coated with the antioxidant(s), and the side surfaces of the endoprosthesis can be free of the antioxidant(s). Prior to applying the antioxidant(s), the inner surface or the outer surface of the bioerodible tube can be masked to apply the antioxidant(s) to only selected portion(s) of the tube.

The endoprosthesis can be made of a desired shape and size (e.g., coronary stents, aortic stents, peripheral vascular stents, gastrointestinal stents, urology stents, and neurology stents). Depending on the application, the endoprosthesis can have a diameter of between, for example, 1 mm to 46 mm. In certain embodiments, a coronary stent can have an expanded diameter of from about 2 mm to about 6 mm. In some embodiments, a peripheral stent can have an expanded diameter of from about 5 mm to about 24 mm. In certain embodiments, a gastrointestinal and/or urology stent can have an expanded diameter of from about 6 mm to about 30 mm. In some embodiments, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm.

The endoprostheses described herein can be configured for non-vascular lumens. For example, they can be configured for use in the esophagus or the prostate. Other lumens include biliary lumens, hepatic lumens, pancreatic lumens, urethral lumens and ureteral lumens.

In use, the endoprosthesis can be used, e.g., delivered and expanded, using a catheter delivery system, such as a balloon catheter system. Catheter systems are described in, for example, Wang U.S. Pat. No. 5,195,969, Hamlin U.S. Pat. No. 5,270,086, and Raeder-Devens, U.S. Pat. No. 6,726,712. Endoprosthesis delivery, such as stent delivery, are also exemplified by the Radius® or Symbiot® systems, available from Boston Scientific Scimed, Maple Grove, Minn.

The endoprostheses described herein can be a covered stent or a stent-graft. For example, the stent described herein can include and/or be attached to a biocompatible, non-porous or semi-porous polymer matrix including polytetrafluoroethylene (PTFE), expanded PTFE, polyethylene, urethane, or polypropylene.

The endoprostheses can further include a releasable therapeutic agent, drug, or a pharmaceutically active compound, such as described in U.S. Pat. No. 5,674,242, U.S. Ser. No. 09/895,415, filed Jul. 2, 2001, U.S. Ser. No. 11/111,509, filed Apr. 21, 2005, and U.S. Ser. No. 10/232,265, filed Aug. 30, 2002. The therapeutic agents, drugs, or pharmaceutically active compounds can include, for example, anti-thrombogenic agents, antioxidants, anti-inflammatory agents, anesthetic agents, anti-coagulants, and antibiotics. The therapeutic agent, drug, or a pharmaceutically active compound can be dispersed in a polymeric coating carried by the stent. The polymeric coating can include more than a single layer. For example, the coating can include two layers, three layers or more layers, e.g., five layers. The therapeutic agent can be a genetic therapeutic agent, a non-genetic therapeutic agent, or cells. Therapeutic agents can be used singularly, or in combination. Therapeutic agents can be, for example, nonionic, or they may be anionic and/or cationic in nature. An example of a therapeutic agent is one that inhibits restenosis, such as paclitaxel. The therapeutic agent can also be used, e.g., to treat and/or inhibit pain, encrustation of the stent or sclerosing or necrosing of a treated lumen. Any of the above coatings and/or polymeric portions can be dyed or rendered radioopaque.

In other embodiments, an endoprosthesis includes one or more filaments or wires including one or more bioerodible materials and one or more antioxidants applied to the bioerodible material(s) as described above. The filaments or wires can be knitted, woven, or braided to form an endoprosthesis. All the filaments or only selected filaments can include bioerodible material and the antioxidant. The bioerodible material and/or the antioxidant can be the same or different.

All references, such as patent applications, publications, and patents, referred to herein are incorporated by reference in their entirety.

Other embodiments are within the scope of the claims.

What is claimed is:

1. An endoprosthesis, comprising:
    a member comprising a bioerodible material, wherein the bioerodible material is iron or magnesium; and
    an antioxidant carried by the member, wherein the antioxidant is encapsulated by the bioerodible material.

2. An endoprosthesis, comprising:
    a member comprising a bioerodible material, wherein the bioerodible material is iron or magnesium and
    an antioxidant within a matrix of the bioerodible material.

3. The endoprosthesis of claim 1, wherein the antioxidant comprises a phenol.

4. The endoprosthesis of claim 1, wherein the member comprises a tubular member constructed to maintain patency of a body vessel.

5. The endoprosthesis of claim 1, further comprising a drug carried by the member.

6. The endoprosthesis of claim 1, in the form of a stent.

7. A method of making an endoprosthesis, the method comprising incorporating a bioerodible material with an antioxidant to form at least a portion of the endoprosthesis, wherein the bioerodible material is iron or magnesium and the antioxidant is encapsulated by the bioerodible material.

8. The method of claim 7, wherein the bioerodible material is in the form of a tubular member.

9. The method of claim 7, wherein the bioerodible material is in the form of a tubular member, and the antioxidant is incorporated in a select portion of the tubular member.

10. The method of claim 7, wherein the antioxidant is in a particle encapsulated by a bioerodible material.

11. The method of claim 10, wherein the particle comprises zinc oxide.

12. The method of claim 7, wherein the antioxidant comprises a phenol.

13. The method of claim 12, wherein the antioxidant is selected from the group consisting of eugenol, isoeugenol, and acetyl-eugenol.

14. The method of claim 7, wherein the portion is a tubular member constructed to maintain patency of a body vessel.

15. The method of claim 7, further comprising incorporating a drug with the portion.

16. The method of claim 7, wherein the endoprosthesis has the form of a stent.

17. The method of claim 7, wherein the bioerodible material is magnesium.

* * * * *